US011951136B2

(12) United States Patent
Ward et al.

(10) Patent No.: US 11,951,136 B2
(45) Date of Patent: Apr. 9, 2024

(54) PRESERVATION OF PANCREATIC ISLET GRAFTS IN THE EXTRAHEPATIC SPACE

(71) Applicants: THE REGENTS OF THE UNIVERSITY OF CALIFORNIA, Oakland, CA (US); U.S. GOVERNMENT REPRESENTED BY THE DEPARTMENT OF VETERANS AFFAIRS, Washington, DC (US)

(72) Inventors: Casey Ward, San Francisco, CA (US); Qizhi Tang, San Francisco, CA (US); Peter Stock, San Francisco, CA (US); Gaetano Faleo, San Francisco, CA (US); Gopika Nair, San Francisco, CA (US); Matthias Hebrok, San Francisco, CA (US); Wenhan Chang, San Francisco, CA (US); Thuy Vo, San Francisco, CA (US); Jeffrey A. Bluestone, San Francisco, CA (US); Eleonora De Klerk, San Francisco, CA (US)

(73) Assignees: The Regents of the University of California, Oakland, CA (US); The United States Government as Represented by the Department of Veterans Affairs, Washington, DC (US)

( * ) Notice: Subject to any disclaimer, the term of this patent is extended or adjusted under 35 U.S.C. 154(b) by 506 days.

(21) Appl. No.: 16/772,078

(22) PCT Filed: Dec. 12, 2018

(86) PCT No.: PCT/US2018/065279
§ 371 (c)(1),
(2) Date: Jun. 11, 2020

(87) PCT Pub. No.: WO2019/118641
PCT Pub. Date: Jun. 20, 2019

(65) Prior Publication Data
US 2020/0360446 A1    Nov. 19, 2020

Related U.S. Application Data

(60) Provisional application No. 62/597,825, filed on Dec. 12, 2017, provisional application No. 62/721,184, filed on Aug. 22, 2018.

(51) Int. Cl.
| | |
|---|---|
| A61P 3/10 | (2006.01) |
| A61K 9/00 | (2006.01) |
| A61K 35/39 | (2015.01) |
| A61K 35/55 | (2015.01) |
| C12N 5/071 | (2010.01) |

(52) U.S. Cl.
CPC ............ *A61K 35/55* (2013.01); *A61K 9/0019* (2013.01); *A61K 9/0024* (2013.01); *A61K 35/39* (2013.01); *A61P 3/10* (2018.01); *C12N 5/0617* (2013.01); *C12N 5/0676* (2013.01); *A61K 2300/00* (2013.01); *C12N 2506/02* (2013.01); *C12N 2506/078* (2013.01)

(58) Field of Classification Search
CPC .... A61K 35/55; A61K 9/0019; A61K 9/0024; A61K 35/39; A61K 2300/00; A61P 3/10; C12N 5/0617; C12N 5/0676; C12N 2506/02; C12N 2506/078
See application file for complete search history.

(56) References Cited

U.S. PATENT DOCUMENTS

| | | |
|---|---|---|
| 5,011,494 A | 4/1991 | von Recum et al. |
| 5,100,392 A | 3/1992 | Orth et al. |
| 5,219,361 A | 6/1993 | von Recum et al. |
| 5,314,471 A | 5/1994 | Brauker et al. |
| 5,324,518 A | 6/1994 | Orth et al. |
| 5,344,454 A | 9/1994 | Clarke et al. |
| 5,421,923 A | 6/1995 | Clarke et al. |
| 5,453,278 A | 9/1995 | Chan et al. |
| 5,545,223 A | 8/1996 | Neuenfeldt et al. |
| 5,549,675 A | 8/1996 | Neuenfeldt et al. |
| 5,569,462 A | 10/1996 | Martinson et al. |
| 5,593,440 A | 1/1997 | Brauker et al. |
| 5,653,756 A | 8/1997 | Clarke et al. |
| 5,713,888 A | 2/1998 | Neuenfeldt et al. |
| 5,733,336 A | 3/1998 | Neuenfeldt et al. |

(Continued)

FOREIGN PATENT DOCUMENTS

| | | |
|---|---|---|
| WO | 2012/035539 A1 * | 3/2012 |
| WO | WO-2016/141460 A1 | 9/2016 |

(Continued)

OTHER PUBLICATIONS

Oh (American Journal of Transplantation, Published 2013, pp. 1429-1440) (Year: 2013).*
Barczyfiski, M. et al. (Oct. 2017). "Parathyroid transplantation in thyroid surgery," Gland Surg 6(5):530-536.
Chang, R. et al. (Aug. 22, 2017). "Nanoporous Immunoprotective Device for Stem-Cell-Derived β-Cell Replacement Therapy," *ACS Nano* 11(8):7747-7757.
Chang et al. (Sep. 2, 2008). "The Extracellular Calcium-Sensing Receptor (CaSR) Is a Critical Modulator of Skeletal Development," *Sci Signal* 1(35): ra1.

(Continued)

*Primary Examiner* — Alma Pipic
(74) *Attorney, Agent, or Firm* — Mintz Levin Cohn Ferris Glovsky and Popeo, P.C.

(57) ABSTRACT

Provided herein, inter alia, are methods and compositions for treating diabetes mellitus comprising co-transplantation of an insulin-producing cell and a cell derived from a parathyroid gland (PTG), a CD34+ cell derived from a parathyroid gland, a CD34+ cell derived from a stem cell, or other progenitor cell-derived CD34+ cell.

24 Claims, 46 Drawing Sheets

(56) References Cited

U.S. PATENT DOCUMENTS

| | | | |
|---|---|---|---|
| 5,741,330 | A | 4/1998 | Brauker et al. |
| 5,782,912 | A | 7/1998 | Brauker et al. |
| 5,800,529 | A | 9/1998 | Brauker et al. |
| 5,807,406 | A | 9/1998 | Brauker et al. |
| 5,882,354 | A | 3/1999 | Brauker et al. |
| 5,964,261 | A | 10/1999 | Neuenfeldt et al. |
| 5,964,804 | A | 10/1999 | Brauker et al. |
| 6,060,640 | A | 5/2000 | Pauley et al. |
| 6,156,305 | A | 12/2000 | Brauker et al. |
| 6,520,997 | B1 | 2/2003 | Pekkarinen et al. |
| 6,773,458 | B1 | 8/2004 | Brauker et al. |
| 9,526,749 | B2 | 12/2016 | Walker et al. |
| 2009/0053182 | A1* | 2/2009 | Ichim |
| 2012/0295347 | A1 | 11/2012 | Kessler |
| 2013/0034525 | A1* | 2/2013 | Yu |
| 2016/0015756 | A1* | 1/2016 | Broytman |

FOREIGN PATENT DOCUMENTS

| | | |
|---|---|---|
| WO | WO-2017/019702 A1 | 2/2017 |
| WO | WO-2017/177163 A1 | 10/2017 |

OTHER PUBLICATIONS

Cheng, Z. et al. (May 2013). "Sex and age modify biochemical and skeletal manifestations of chronic hyperparathyroidism by altering target organ responses to Ca2+ and parathyroid hormone in mice," *J Bone Miner Res* 28(5):1087-1100.

Corbetta, S. et al. (Sep. 2009, e-published Jul. 30, 2009). "Expression of parathyroid-specific genes in vascular endothelial progenitors of normal and tumoral parathyroid glands," *Am J Pathol* 175(3):1200-1207.

El-Badawy, A. et al. (Apr. 13, 2016). "Clinical Efficacy of Stem Cell Therapy for Diabetes Mellitus: A Meta-Analysis," *PLoS One* 11(4):e0151938.

Evron, Y. et al. (Apr. 25, 2018). "Long-term viability and function of transplanted islets macroencapsulated at high density are achieved by enhanced oxygen supply," *Sci Rep*. 8(1):6508.

Faleo, G. et al. (Sep. 12, 2017). "Mitigating Ischemic Injury of Stem Cell-Derived Insulin-Producing Cells after Transplant," *Stem Cell Reports* 9(3):807-819.

International Search Report dated May 6, 2019, for PCT Application No. PCT/US2018/065279, filed Dec. 12, 2018, 4 pages.

Lewandowski, J. et al. (Oct. 2016, e-published Mar. 3, 2016). "Techniques of Human Embryonic Stem Cell and Induced Pluripotent Stem Cell Derivation," *Arch Immunol Ther Exp (Warsz)*. 64(5): 349-370.

Lo, C-Y. (Dec. 2002). "Parathyroid autotransplantation during thyroidectomy," *ANZ J Surg* 72(12):902-907.

Micallef, S.J. et al. (Mar. 2012). "INS(GFP/w) human embryonic stem cells facilitate isolation of in vitro derived insulin-producing cells," *Diabetologia* 55(3):694-706.

Nyitray, C.E. et al. (Jun. 23, 2015). "Polycaprolactone Thin-Film Micro- and Nanoporous Cell-Encapsulation Devices," *ACS Nano* 9(6):5675-5682.

Oh, B.J. et al. (Jun. 2013, e-published Apr. 18, 2013). "Co-transplantation of bone marrow-derived endothelial progenitor cells improves revascularization and organization in islet grafts," *Am J Transplant* 13(6):1429-1440.

Pagliuca, F.W. et al. (Oct. 9, 2014). "Generation of functional human pancreatic β cells in vitro," *Cell* 159(2):428-439.

Rezania, A. et al. (Nov. 2014, e-published Sep. 11, 2014). "Reversal of diabetes with insulin-producing cells derived in vitro from human pluripotent stem cells," *Nat. Biotechnol*. 32(11):1121-1133.

Russ, H.A. et al. (Jul. 2, 2015). "Controlled induction of human pancreatic progenitors produces functional beta-like cells in vitro," *EMBO J* 34(13):1759-1772.

Szot, G.L. et al. (Sep. 27, 2009). "Successful clinical islet isolation using a GMP-manufactured collagenase and neutral protease," *Transplantation* 88(6):753-756.

Szot, G.L. et al. (2007, e-published Aug. 22, 2007). "Murine pancreatic islet isolation," *J Vis Exp*. (7):255.

Written Opinion dated May 6, 2019, for PCT Application No. PCT/US2018/065279, filed Dec. 12, 2018, 12 pages.

\* cited by examiner

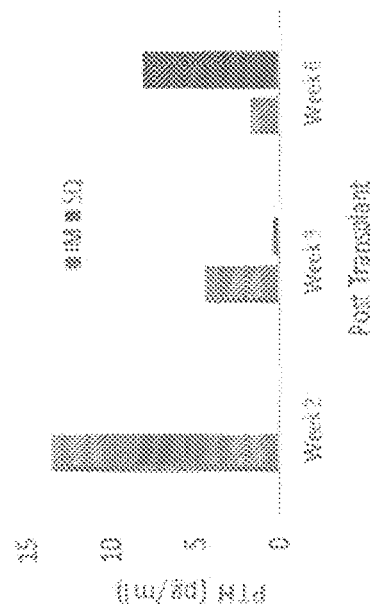
FIG. 2C
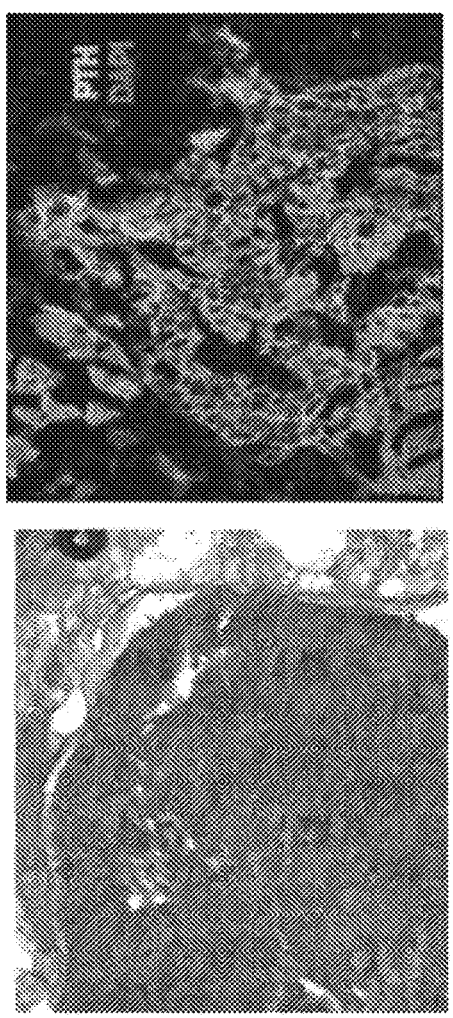
FIG. 2B
FIG. 2A

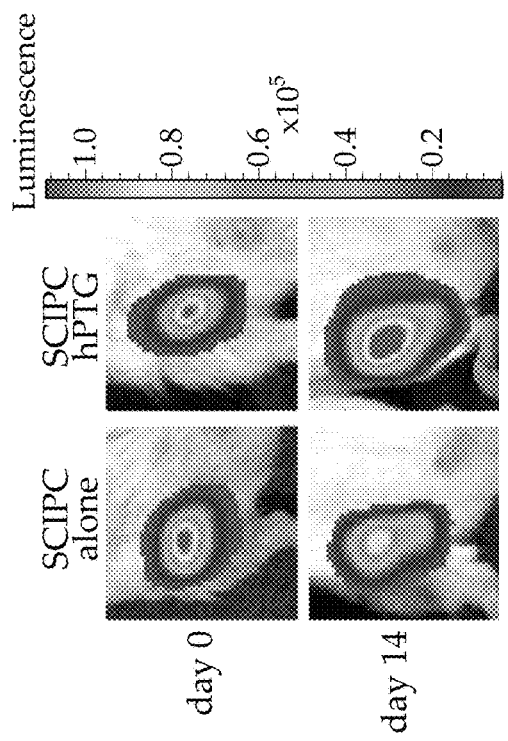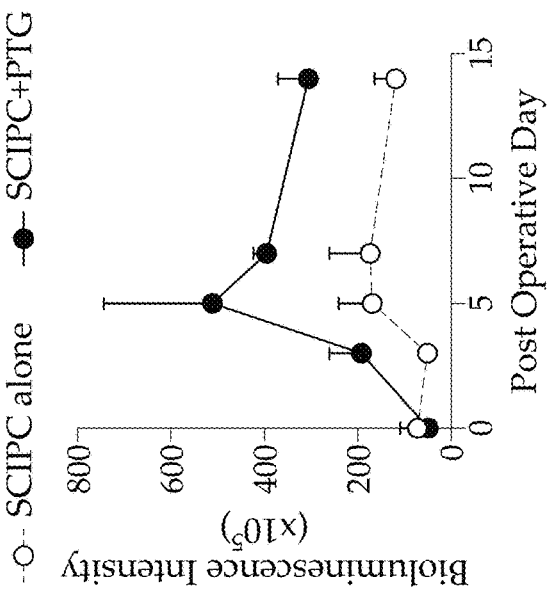
FIG. 3A
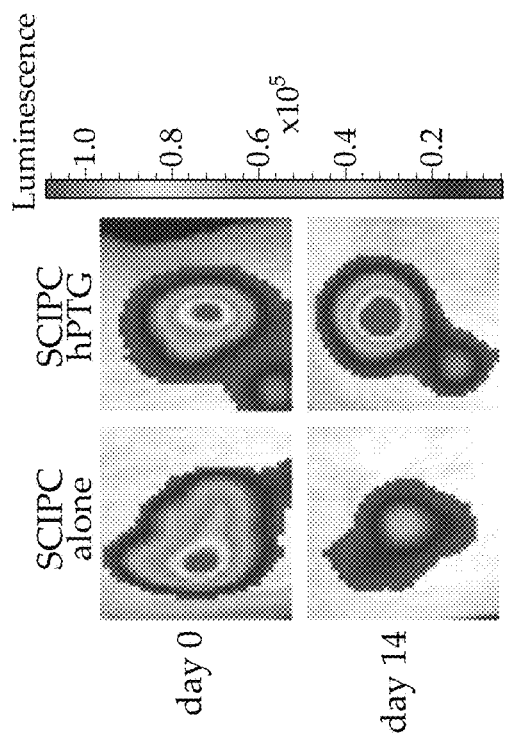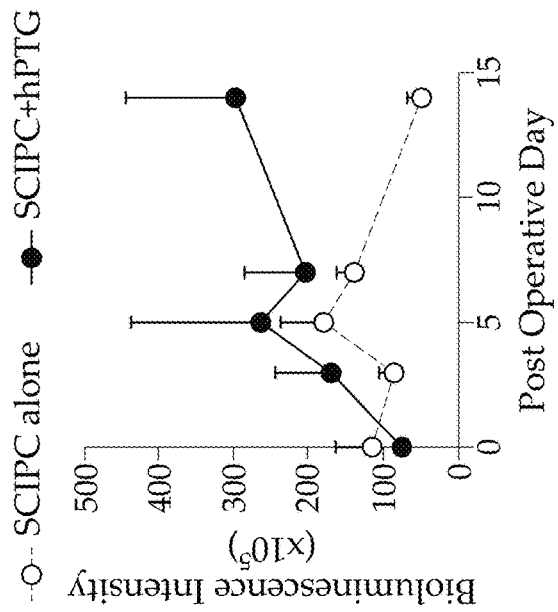
FIG. 3B

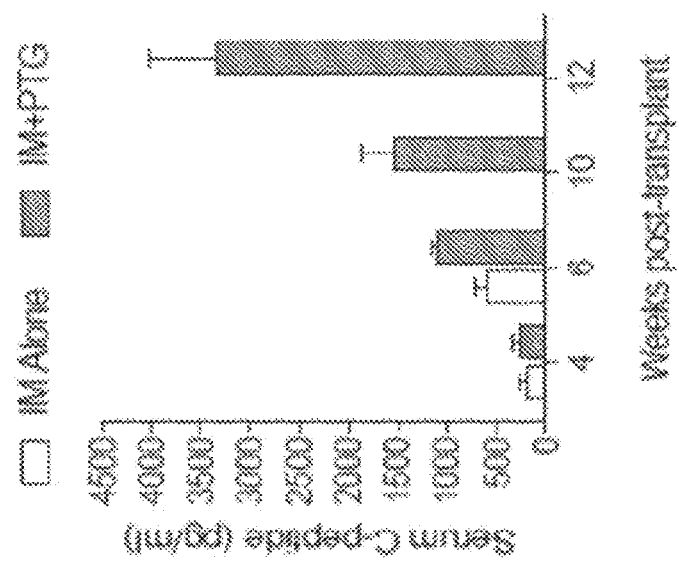

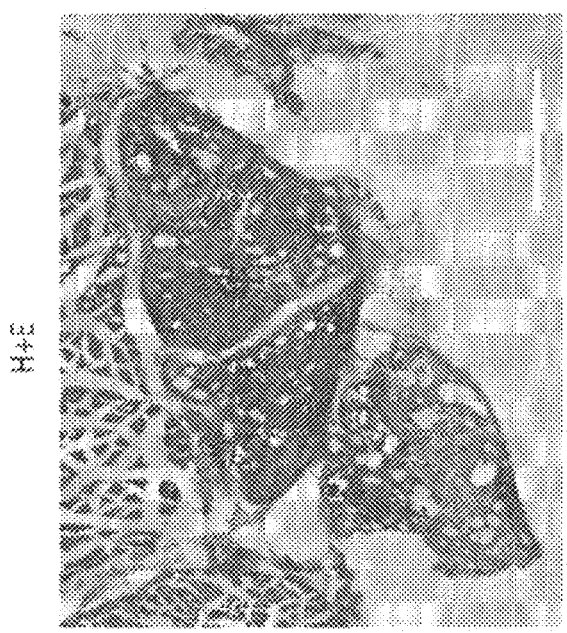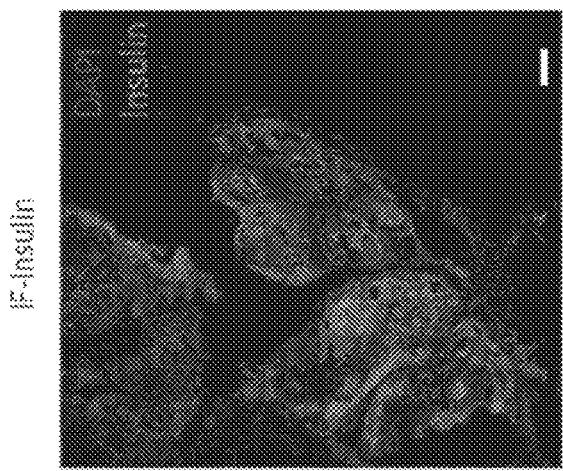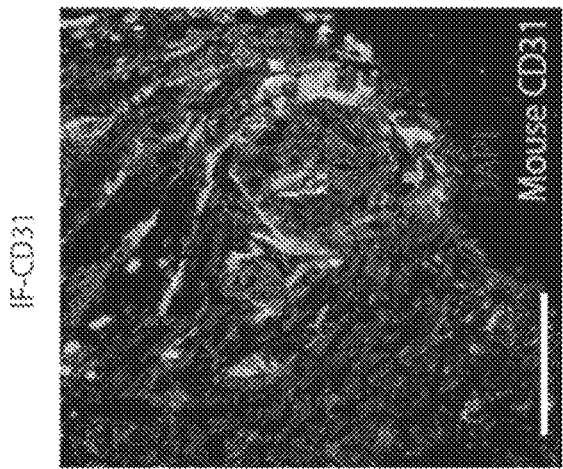

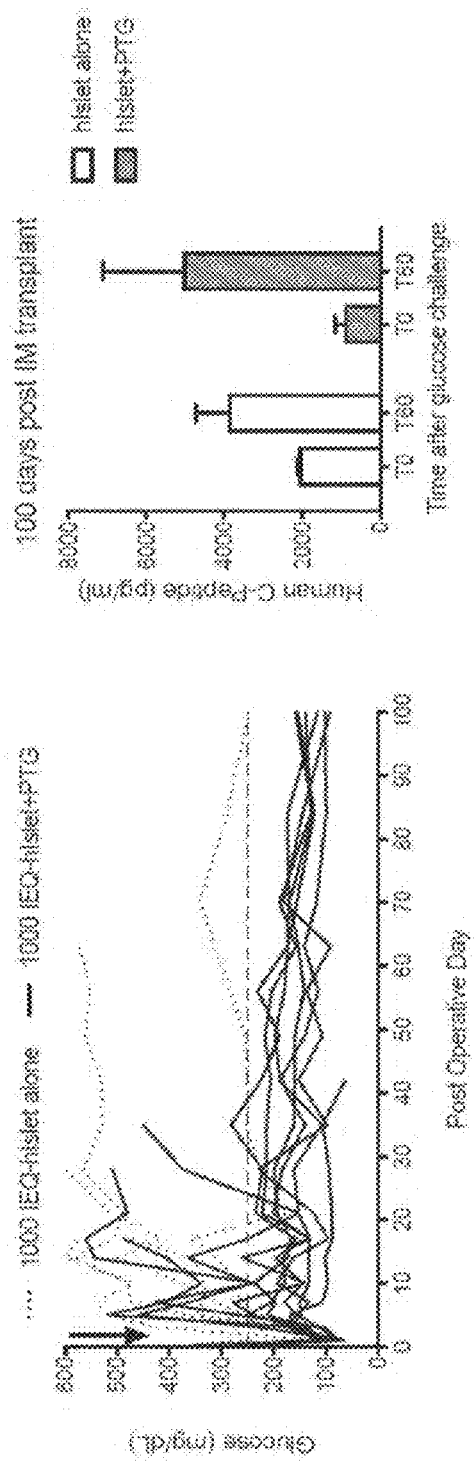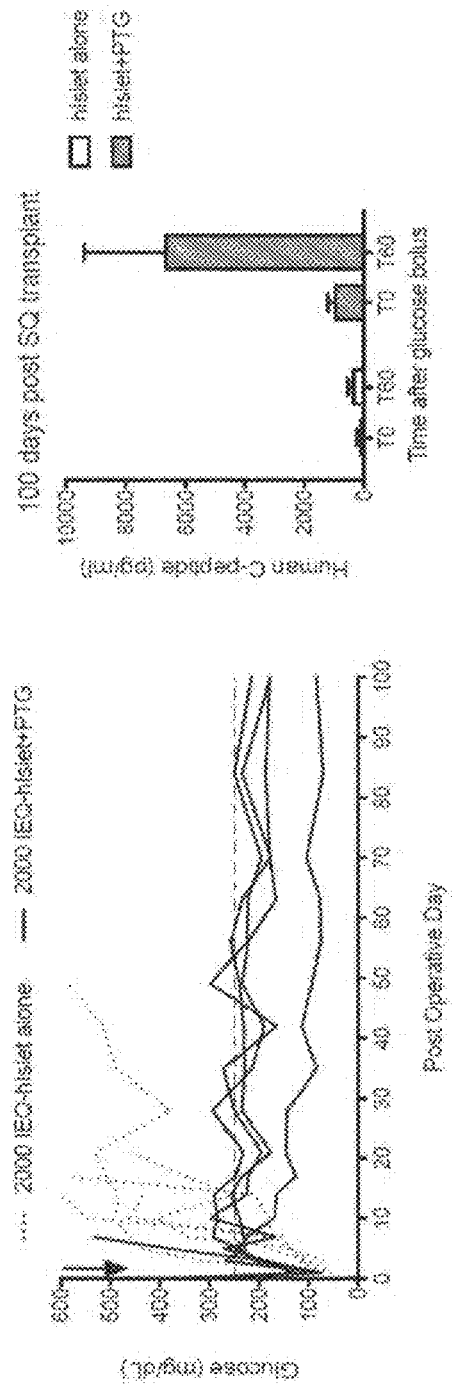

CCL2

CXCL12

Mitochondrial Respiration

GSEA
Go: Oxidative Phosphorylation

Scatter plot

In vivo engraftment
C-PEP/GCG/SST

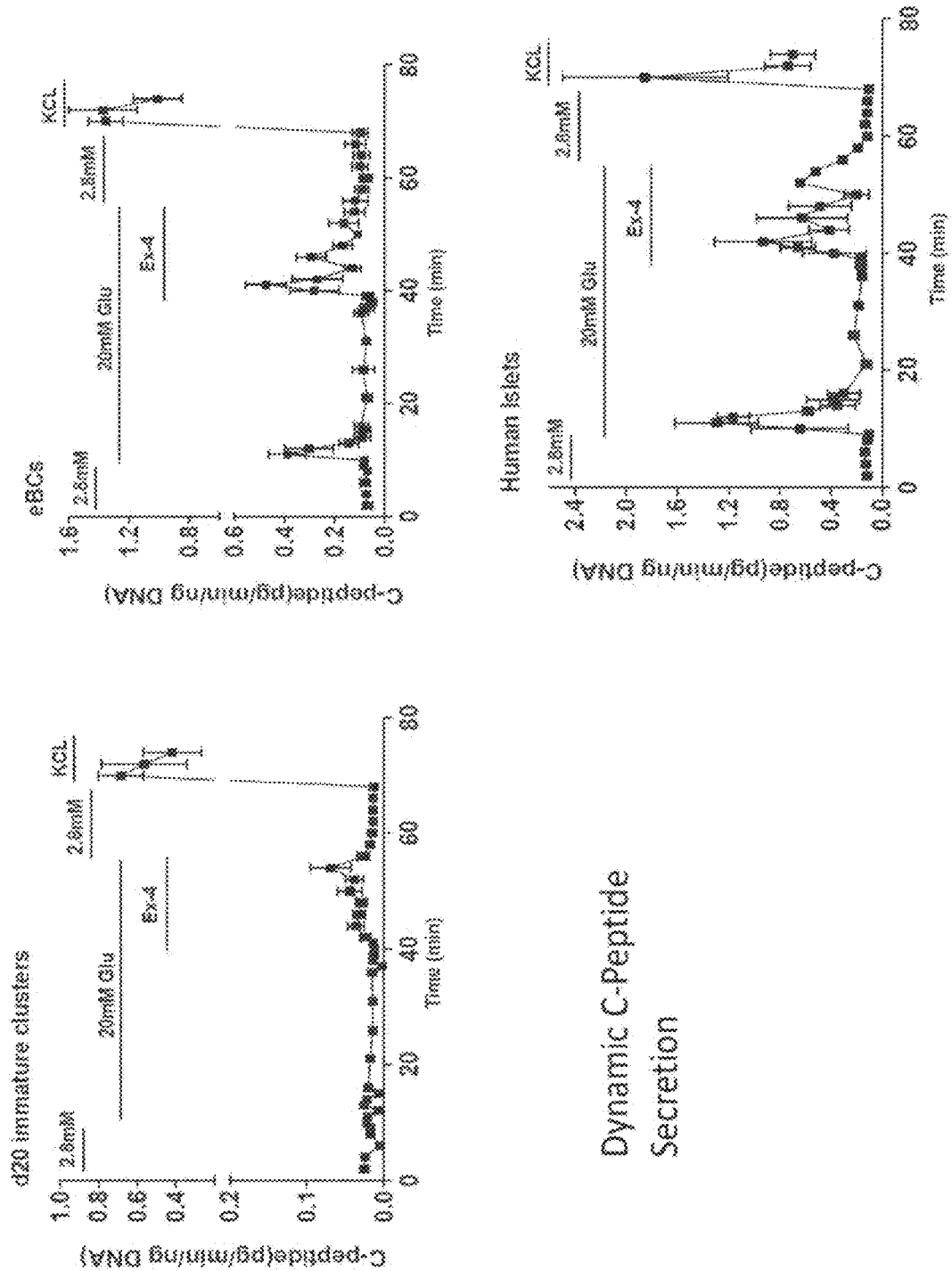

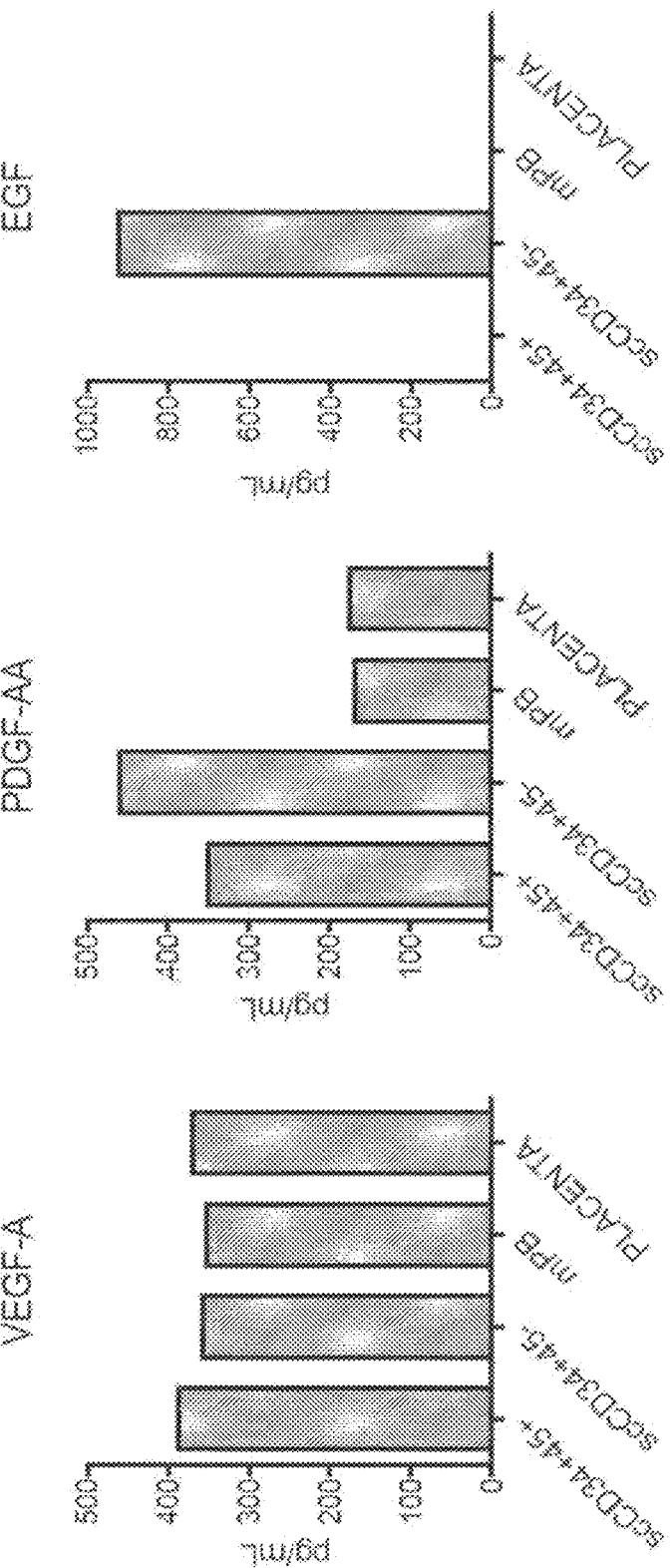

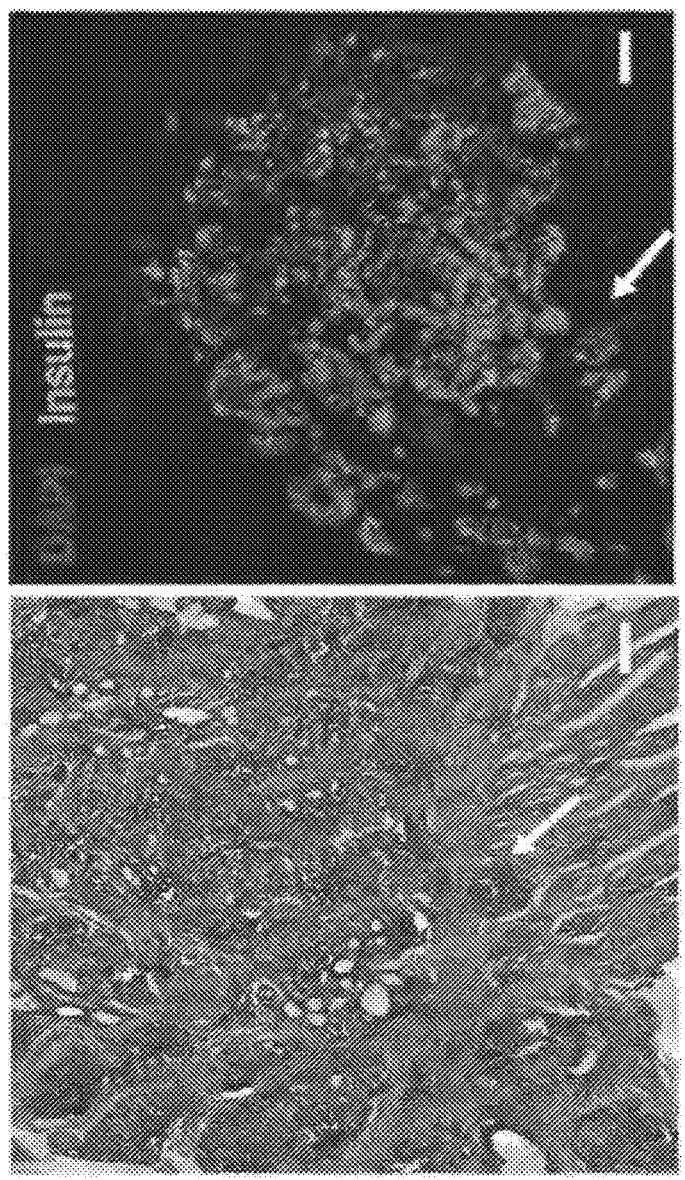

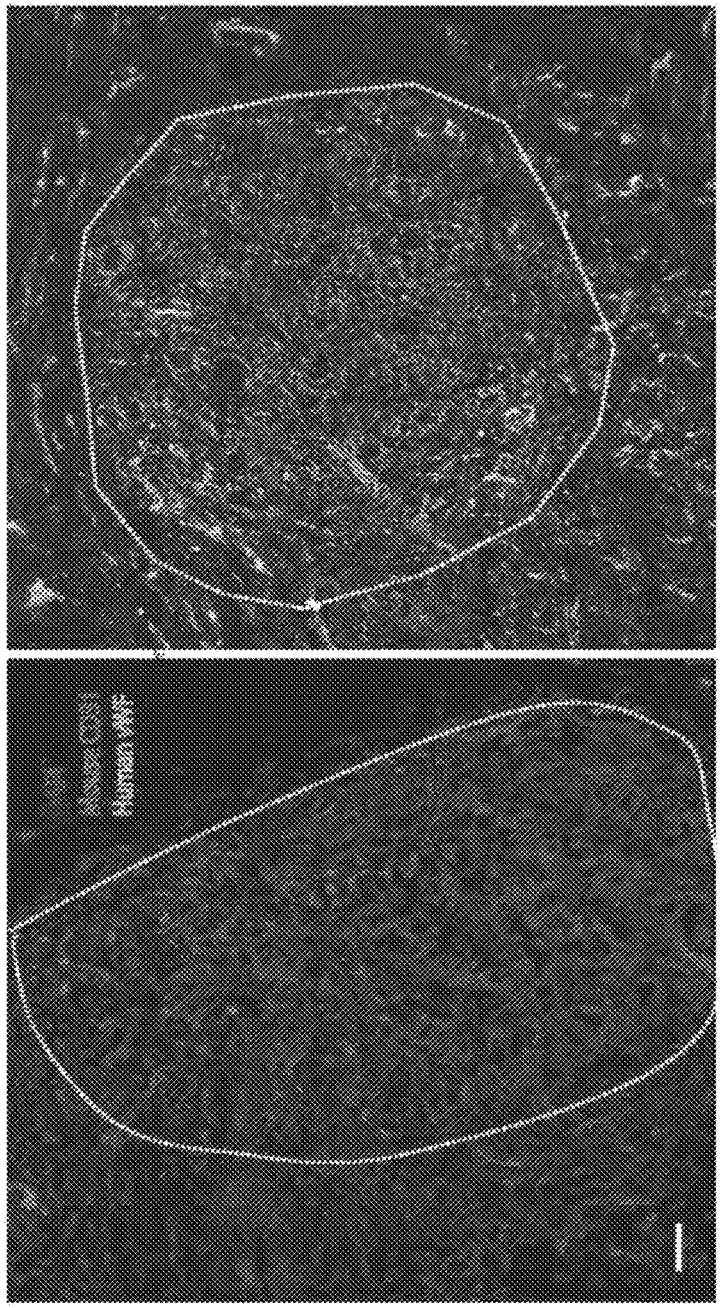

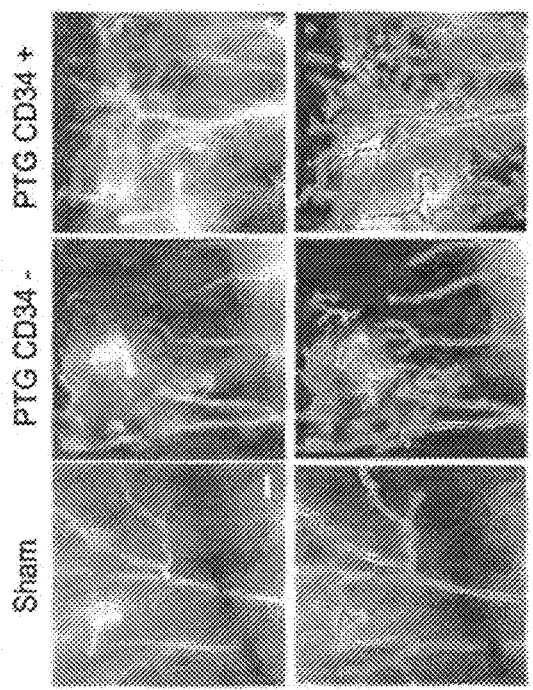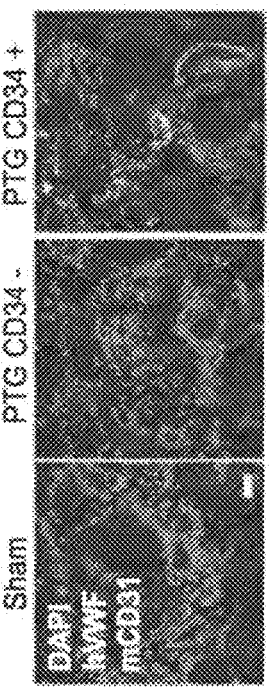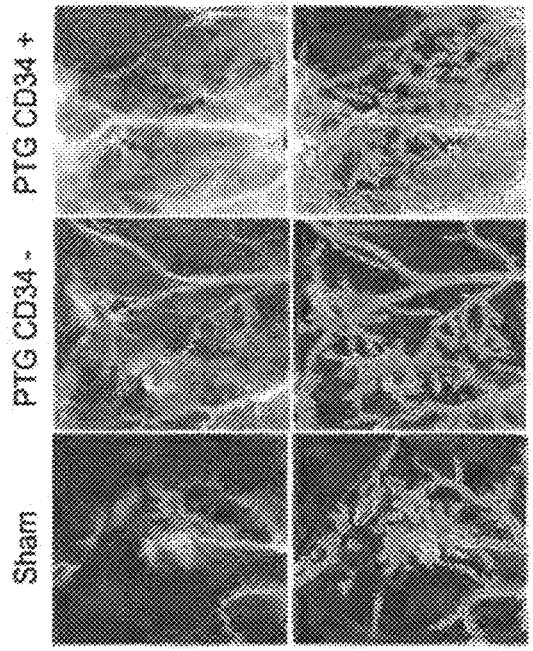

PRESERVATION OF PANCREATIC ISLET GRAFTS IN THE EXTRAHEPATIC SPACE

CROSS-REFERENCE TO RELATED APPLICATIONS

The present application is a U.S. National Phase Application of PCT International Application No. PCT/US2018/065279, filed on Dec. 12, 2018, designating the United States of America, which is an International Application of and claims priority to U.S. Provisional Patent Application Ser. No. 62/597,825, filed on Dec. 12, 2017; and U.S. Provisional Patent Application Ser. No. 62/721,184, filed on Aug. 22, 2018. The contents of the above-referenced applications are herein expressly incorporated by reference in their entireties, including any drawings.

GOVERNMENT INTEREST

This invention was made with government support under grant nos. R01 DK105831, P30 DK063720, and AI25222 awarded by the National Institutes of Health. The government has certain rights in the invention.

FIELD

Disclosed herein, inter alia are methods and compositions for treatment of diabetes mellitus and the preservation of pancreatic islet grafts in the extrahepatic space.

BACKGROUND

Diabetes Mellitus (DM) is a disease defined by elevated fasting glucose levels (otherwise known as hyperglycemia). Hyperglycemia occurs when the body produces low levels of insulin or the insulin produced is deficient. DM can be classified as: (1) Type 1 Diabetes Mellitus (T1DM), where insulin production is reduced or ceased due to immune-mediated damage to the beta cells of the islets of Langerhans in the pancreas; (2) Type 2 Diabetes Mellitus (T2DM), caused by a deficiency in insulin production by the pancreas relative to excessive body weight and/or insulin resistance by cells in the liver, muscles and fat tissue; or (3) other, rarer, forms of DM such as DM resulting from pancreas surgery or congenital defects that affect the development or function of the pancreatic islets.

The most effective site currently used for transplantation of pancreatic islets in individuals with type 1 diabetes is the liver, accessed by infusion into the portal vein of the recipient. Although this site has proven to be the most effective site for transplantation, survival of islets (islet engraftment) following portal vein infusion is compromised and limits the efficacy of this procedure. Despite the limitations of the intrahepatic site, it has been the only site that has resulted in insulin independence following islet transplantation in humans. Survival into other more accessible sites, such as the subcutaneous or intramuscular space, has been more challenging due to poor engraftment and failure to achieve insulin independence. These are the preferred sites for transplanting stem-cell-derived islets or xenogeneic islets, as they are readily accessible for implantation and removal. Encapsulation of stem-cell-derived sources of islets can ensure the safety of the transplant and potentially eliminate the need of immunosuppression. However, islets almost universally fail in various encapsulation devices that further limit the blood supply to the graft after transplant. What is needed, therefore, are improved methods and compositions for increasing the efficiency and effectiveness of pancreatic islet beta cell engraftment following transplantation into individuals with DM, particularly for improving engraftment of these cells in the extra-hepatic space.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY

Provided herein, inter alia, are novel methods and compositions for engrafting insulin-producing cells (such as, pancreatic islet beta cells and/or stem cell-derived beta cells) into individuals to reverse DM in individuals in need thereof. Successful engraftment of insulin-producing cells can be successfully achieved in the extra-hepatic space, such as in the subcutaneous space or intramuscularly.

In a first aspect, there is provided a method for treating diabetes mellitus in an individual in need thereof comprising co-transplanting a therapeutically effective amount of an insulin-producing cell and a cell derived from a parathyroid gland into the individual, thereby treating diabetes mellitus. In another aspect, provided herein is a method for treating diabetes mellitus in an individual in need thereof comprising co-transplanting a therapeutically effective amount of an insulin-producing cell and a $CD34^+$ cell derived from a parathyroid gland into the individual, thereby treating diabetes mellitus. In a further aspect, provided herein is a method for treating diabetes mellitus in an individual in need thereof comprising (a) isolating a $CD34^+$ cell from a parathyroid gland; and (b) co-transplanting a therapeutically effective amount of the isolated $CD34^+$ cell and an insulin-producing cell into the individual, thereby treating diabetes mellitus. In yet another aspect, provided herein is a method for engrafting an insulin-producing cell into an individual comprising co-transplanting an insulin-producing cell and a cell derived from a parathyroid gland into the individual, thereby engrafting the insulin-producing cell into the individual. In some embodiments of any of the embodiments disclosed herein, the insulin-producing cell is a component of a pancreatic islet. In some embodiments of any of the embodiments disclosed herein, the insulin-producing cell is a beta cell, a Stem Cell-Derived Insulin-Producing Cell (SCIPC), and/or an Enhanced Beta Cluster (eBC). In some embodiments of any of the embodiments disclosed herein, the insulin-producing cell is human in origin. In some embodiments of any of the embodiments disclosed herein, the insulin-producing cell is porcine in origin. In some embodiments of any of the embodiments disclosed herein, the cell derived from the parathyroid gland is human in origin. In some embodiments, the insulin-producing cell is derived from the individual or from a donor. In some embodiments, the cell derived from the parathyroid gland is derived from the parathyroid gland of the individual or from a donor. In some embodiments of any of the embodiments disclosed herein, the cell derived from the parathyroid gland produces one or more of proangiogenic factors and/or pro-islet hormones. In some embodiments of any of the embodiments disclosed herein, the proangiogenic factors are one or more factors selected from the group consisting of vascular endothelial growth factor (VEGF), platelet-derived growth factor (PDGF), and angiopoietin. In some embodiments, the pro-islet hormones are one or more hormones selected from the group consisting of GABA, PTH and PTHrP. In some embodiments of any of the embodiments disclosed herein, the insulin-producing cell and the cell derived from parathyroid gland are co-transplanted into a subcutaneous space. In some embodiments of any of the embodiments disclosed herein, the insulin-producing cell and the cell derived from parathyroid gland are co-transplanted intramuscularly. In some embodiments of any of the embodiments disclosed herein, the diabetes mellitus is type 1 diabetes, type 2 diabetes, or surgical diabetes. In some embodiments of any of the embodiments disclosed herein, the individual is human.

In other aspects, provided herein is a catheter comprising (a) an insulin-producing cell and (b) a cell derived from a parathyroid gland and/or a CD34$^+$ cell. In another aspect, provided herein is a cannula comprising (a) an insulin-producing cell and (b) a cell derived from a parathyroid gland and/or a CD34$^+$ cell. Further provided, in yet another aspect, is a syringe comprising (a) an insulin-producing cell and (b) a cell derived from a parathyroid gland and/or a CD34$^+$ cell.

In a further aspect, provided herein is a pharmaceutical composition comprising: (a)(i) a Stem Cell-Derived Insulin-Producing Cell (SCIPC), (ii) an Enhanced Beta Cluster (eBC), and/or (iii) human islets; (b) a cell derived from a parathyroid gland and/or a CD34$^+$ cell; and (c) one or more pharmaceutically acceptable excipients. In some embodiments, the cell derived from the parathyroid gland and/or a CD34$^+$ cell is human in origin. In some embodiments of any of the embodiments disclosed herein, the cell derived from the parathyroid gland and/or a CD34$^+$ cell produces one or more of proangiogenic factors and/or pro-islet hormones. In some embodiments, the proangiogenic factors are one or more factors selected from the group consisting of VEGF, PDGF, and angiopoietin. In some embodiments, the pro-islet hormones are one or more hormones selected from the group consisting of GABA, PTH and PTHrP. In some embodiments of any of the embodiments disclosed herein, the eBC produces insulin within three days post-transplantation. In some embodiments of any of the embodiments disclosed herein, the eBC produces C-peptide.

In other aspects, provided herein is a method for treating diabetes mellitus in an individual in need thereof comprising co-transplanting a therapeutically effective amount of a stem cell-derived pancreatic endocrine progenitor cell and a cell derived from a parathyroid gland into the individual, thereby treating diabetes mellitus. In some embodiments, the stem cell-derived pancreatic endocrine progenitor cell is a Stem Cell-Derived Insulin-Producing Cell (SCIPC). In a further aspect, provided herein is a method for treating diabetes mellitus in an individual in need thereof comprising co-transplanting a therapeutically effective amount of a stem cell-derived pancreatic beta cell and a cell derived from a parathyroid gland into the individual, thereby treating diabetes mellitus. In some embodiments, the stem cell-derived pancreatic beta cell is an Enhanced Beta Cluster (eBC). In some embodiments of any of the embodiments disclosed herein, the stem cell is human in origin. In some embodiments of any of the embodiments disclosed herein, the cell derived from the parathyroid gland is human in origin. In some embodiments, the stem cell is derived from the individual or from a donor. In some embodiments, the cell derived from the parathyroid gland is derived from the parathyroid gland of the individual or from a donor. In some embodiments of any of the embodiments disclosed herein, the cell derived from the parathyroid gland produces one or more of proangiogenic factors and/or pro-islet hormones. In some embodiments, the proangiogenic factors are one or more factors selected from the group consisting of VEGF, PDGF, and angiopoietin. In some embodiments, the pro-islet hormones are one or more hormones selected from the group consisting of GABA, PTH and PTHrP. In some embodiments of any of the embodiments disclosed herein, the stem cell-derived cell and the cell derived from parathyroid gland are co-transplanted into a subcutaneous space. In some embodiments of any of the embodiments disclosed herein, the stem cell-derived cell and the cell derived from parathyroid gland are co-transplanted intramuscularly. In some embodiments of any of the embodiments disclosed herein, the stem cell-derived cell and the cell derived from parathyroid gland are co-transplanted intraomentally. In some embodiments of any of the embodiments disclosed herein, the diabetes mellitus is type 1 diabetes, type 2 diabetes, or surgical diabetes. In some embodiments of any of the embodiments disclosed herein, the individual is human.

In further aspects, provided herein is a method for treating diabetes mellitus in an individual in need thereof comprising co-transplanting a therapeutically effective amount of an insulin-producing cell and a CD34$^+$ cell into the individual thereby treating diabetes mellitus. In some embodiments, the CD34$^+$ cell is a stem cell-derived CD34$^+$ cell. In some embodiments, the stem cell is derived from bone marrow, umbilical cord blood, a pluripotent stem cell (PSC), blood precursor cells, parathyroid gland (PTG) precursors, mesoderm precursors, or endoderm precursors. In some embodiments, the pluripotent stem cell is an induced pluripotent stem cell (iPSC) or an embryonic stem cell (ESC). In some embodiments of any of the embodiments disclosed herein, the stem cell is human in origin. In some embodiments, the CD34$^+$ cell is derived from a PTG. In some embodiments, the PTG is human in origin. In some embodiments, the PTG is from the individual or from a donor. In some embodiments, the insulin-producing cell is a component of a pancreatic islet. In some embodiments, the insulin-producing cell is a beta cell, a Stem Cell-Derived Insulin-Producing Cell (SCIPC), and/or an Enhanced Beta Cluster (eBC). In some embodiments, the insulin-producing cell is human in origin. In some embodiments, the insulin-producing cell is derived from the individual or from a donor. In some embodiments, the insulin-producing cell is porcine in origin.

Each of the aspects and embodiments described herein are capable of being used together, unless excluded either explicitly or clearly from the context of the embodiment or aspect.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 2A depicts mouse parathyroid gland allo-transplantation with confirmed engraftment at 6 weeks in SQ space.

FIG. 2B depicts cryopreserved human PTG after being finely chopped and inserted into the SQ space of immunodeficient mice after 6 weeks confirming xenotransplant engraftment in NSG mouse. FIG. 2C depicts PTH at human physiologic levels (8-65 pg/mL) in both SQ and IM sites of xenotransplantation at selected time points.

FIG. 3A and FIG. 3B depict representative images of SCIPC.LUC grafts with and without cryopreserved human parathyroid gland transplanted into non-diabetic NSG mice subcutaneously (SQ; FIG. 3A; n=4 per group) and intramuscularly (IM; FIG. 3B; n=5 per group). Quantification of SCIPC grafts over time is shown as percentage of day 0. FIG. 3C depicts non-fasting C-peptide levels 4, 6 and 8 weeks after transplantation of SCIPC with or without PTG in the IM space in STZ-treated diabetic mice (IM, n=5 per group; STZ—streptozotocin).

FIG. 4A depicts H+E section of SCIPC at 6 weeks in the IM space. FIG. 4B depicts immunohistochemistry of a subcutaneous SCIPC graft for insulin. FIG. 4C depicts immunohistochemistry of a subcutaneous SCIPC graft for mouse anti-CD31 demonstrating significant neoangiogenesis from the mouse recipient into human SCIPC xenograft at 6 weeks.

FIG. 6A depicts "intramuscular" transplant of eBC.LUC (n=3 per group). FIG. 6B depicts "subcutaneous" transplant of eBC.LUC (n=4 per group). FIG. 6C depicts immunofluorescence staining of an intramuscularly transplanted eBC graft stained with an antibody to insulin, visualized as red fluorescence.

FIG. 8A depicts transplantation of human islets intramuscularly with or without human PTG. STZ-induced diabetic NSG mice (n=4 per group) were transplanted with 1000 IEQ human islets with (n=10) or without PTG (n=5) in the thigh muscle. All mice received insulin pellets subcutaneously at the time of islet transplant. The insulin pellets were removed on day 3 after transplant as indicated by the arrow. Random non-fasting blood glucose was measured and plotted over time for individual mouse in the graph on the left. Diabetes was defined by pre-operative glucose >300 250 mg/dL. Reversal of diabetes was defined by glucose <250 mg/dL as indicated by the dashed line. On day 100 post-transplant, mice were fasted overnight and blood was collected before (T0) the intraperitoneal injection of a bolus of glucose solution (20 mg/Kg). 60 minutes later (T60), blood was collected again. The concentrations of human C-Peptide in the serum were measured using ELISA and results are shown in the graph on the right (FIG. 8B). FIGS. 8C-8D depict subcutaneous transplant of human islets with (n=5) or without (n=5) human PTG. Experimental procedures are the same as described above for FIGS. 8A-8B except the grafts were transplanted to the subcutaneous space of the flank of the mice and 2000 IEQ were transplanted per mouse.

As illustrated in FIG. 17A, pluripotent stem cells (e.g., Ins-GFP hESCs) were differentiated into CD34$^+$ cells using a 14 day embryoid body-based differentiation protocol in the presence of SCF, FLT3-Ligand, IL3, IL6, TPO and BMP4. FIG. 17B illustrates the morphological progression of the pluripotent stem cells during differentiation, where the stem cells were differentiated as single cells or as clumps.

FIG. 19A: Brightfield images of HUVECs and scCD34$^+$ demonstrate that scCD34$^+$ cells have adherent morphology. FIG. 19B: In vitro angiogenesis assay reveal that HUVECs and scCD34+ cells form tube-like networks after 4 hours in culture.

FIGS. 20A-20D summarize the results from glucose-stimulated insulin secretion test (GSIS) on vascular beta clusters (vBCs) prepared in accordance with some embodiments of the disclosure. FIG. 20A: Dynamic C-peptide secretion in response to different glucose concentrations, exendin-4, and KClLof immature clusters of Day 20 (d20) and eBC are compared to human islets. FIGS. 20B-20C: eBCs were co-clustered with PTG CD34+ or PTG CD34− cells to form vascular beta clusters (vBCs). Glucose-stimulated C-peptide levels measured in vEBC (absolute levels and normalized levels) are presented. FIG. 20D: C-peptide levels in vEBC stimulated by KCL.

FIGS. 24A-24C graphically summarize experimental data illustrating that ES-derived CD34$^+$CD45$^-$ and ES-derived CD34$^+$CD45$^+$ are capable of secreting high levels of VEGF-A, PDGF-AA and EGF molecules when maintained in cultures for 24 hours.

FIGS. 31A-31B depicts histological results from experiments performed to demonstrate that PTG enable high density engraftment of human islets intramuscularly. 2000 IEQ of mature human islets and ⅛ of a PTG was co-transplanted in the SQ site, enabling diabetes reversal in ⅘ mice at 100 days compared to 0/5 mice in SQ alone. Consecutive histology sections were prepared from tissue collected at 100 days post-transplant and were stained with H+E (left) and insulin immunofluorescence acquired on a confocal microscope (right). The images show high density engraftment of human islets in the muscle tissue. Corresponding single islet is indicated by arrow. Scale bar 150 μm.

FIGS. 32A-32B pictorially summarize the results from experiments performed to illustrate that parathyroid gland co-transplantation support human pancreatic islet transplant by provision of vascular endothelial cells and by attracting angiogenesis from the host after transplantation in the mouse subcutaneous tissue. Confocal immunofluorescence images of transplanted human pancreatic islets in immunodeficient mice after 5 days. FIG. 32A: An immunofluorescent micrograph of an islets in the human islet alone group showing sparse ingrowth of recipient blood vessels marked by mouse CD31 and an area of ischemic (at bottom) with no blood vessels. FIG. 32B: With PTG co-transplantation, human (green, human vWF) and mouse (red, mouse CD31) blood vessels are seen forming chimeric vascularization. Stained with DAPI (blue), mouse CD31 Alexa-Fluor 647 (red) and human Von Willebrand Factor Alexa Flour 488 (green). 20×, scale bar=100 µm.

FIGS. 34A, 34B, and 34C pictorially summarize the results from in vivo angiogenesis assay of PTG CD34+ vs CD34− single cells transplanted in subcutaneous sites on days 5 and 14. PTG CD34+ vs CD34− single cells were transplanted in subcutaneous space of NSG mice and control mice received sham operations. Skin flaps were prepared from the anesthetized mice 5 (FIG. 34A) and 14 (FIG. 34B) days later. Images of blood vessels on the skin flaps were quantified using AngioTool software showing marked increase in vascular density (measured by vessel area percentages) and number of vascular junctions in PTG CD34+ vs CD34− vs sham. FIG. 3C: Skin tissue from sham and PTG CD34− and PTG CD34+ cell transplanted mice were collected for histological analyses on day 14 after transplant. Confocal immunofluorescence images of the histological sections illustrate unique ability of PTG CD34+ cells to promote human and mouse chimeric vessel formation (human Von Willebrand Factor (hVWF)) with recipient mouse (mouse CD31) vessels after 14 days. Scale bar 25 µm.

DETAILED DESCRIPTION OF THE DISCLOSURE

Figure 1A:
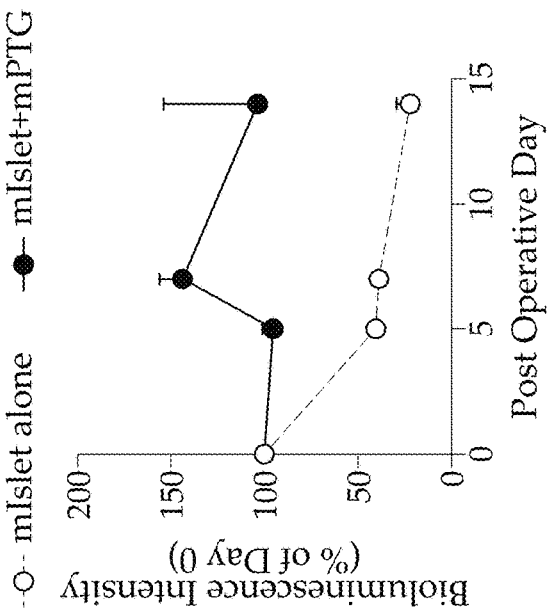
FIG. 1A depicts representative bioluminescence images of B6.MIP.Luc islets with and without B6 parathyroid gland transplanted into non-diabetic B6 albino mice intramuscularly (SQ, n=3 per group). Bioluminescent intensity of islet grafts over time is shown as percentage of day 0.

The present disclosure generally relates to, inter alia, methods and compositions for the treatment of diabetes mellitus. Islet transplantation can cure type 1 diabetes, but multiple donors are needed to achieve insulin independence due to the extensive death of isolated islets away from their native blood supply and tissue microenvironment. Currently, islets are transplanted into the liver by infusion into the portal vein. Intraportal islet transplantation has critical drawbacks. First, it results in excessive islet death due to instant blood-mediated inflammatory reaction and ischemia. This high perioperative loss leads to a need for 3-4 donors per islet transplantation, further exacerbating donor shortage. Second, the inability to monitor and retrieve islets after infusion makes the intraportal transplant approach unsuitable for evaluation of novel therapies using stem cell-derived islets and genetically engineered porcine islets.

As stem cell-derived islets and xenogeneic islets begin to enter early phase clinical trials, there is an urgent need to define optimal extrahepatic transplant sites for islets that permit graft monitoring and retrieval. Unfortunately, islets exhibit even more death in nutrient and oxygen-poor sites such as the subcutaneous (SQ) space, even though sites such as these would be beneficial as they would permit easy monitoring and removal of grafts. Islet death is further exacerbated by the graft encapsulation that is needed to contain potential neoplastic cells that may emerge from stem cell-derived grafts. Thus, islet survival after transplant is a bottleneck that must be addressed to fully realize the benefit of beta cell-replacement therapies regardless of the beta cell source.

As will be discussed more thoroughly herein, the inventors have discovered that co-transplantation of (i) insulin-producing cells or stem cell-derived pancreatic cells with (ii) parathyroid gland (PTG) tissue or cells derived from PTG or a $CD34^+$ cell results in insulin-producing grafts that do not suffer from the same rates of islet cell death observed in hepatic transplantation or the loss of islets that occurs when islets are transplanted into the extra-hepatic space alone. Further, the co-transplanted cells can reverse diabetes in a mouse model of disease. Thus, not only do the methods and compositions disclosed herein result in improved survival of insulin-producing cells following transplantation, but, for the first time, it is shown that these grafts can be established extra-hepatically, such as in the subcutaneous (SC) space or intramuscularly (IM).

Some embodiments of the disclosure relate to the generation of CD34+ vascular endothelial progenitor cells (VEPC) from pluripotent stem cells (PSC), including human embryonic stem cells (ESC) and induced pluripotent stem cells (iPSC), and to their application as a renewable cellular source for promoting engraftment of therapeutic cells and tissues. Some particular embodiments disclosed herein provide a novel strategy for pancreatic endocrine tissue engineering via co-aggregating PTG-derived VEPC or PSC-derived VEPC with beta cells prior to transplantation to improve glucose responsiveness in vitro, as well as engraftment and function in vivo. These strategies have the potential to dramatically change the current clinical landscape for beta cell replacement therapy. In particular, autologous CD34+ cells and insulin-producing cells generated from patient-derived induced pluripotent stem cells (iPSC) cells can potentially overcome immunological barriers while supporting engraftment. Importantly, pluripotent stem cells can be engineered to reduce their immunogenicity and thus enable off-the-shelf use of minimally immunogenic VEPCs for engraftment support of cellular therapies.

I. GENERAL TECHNIQUES

The practice of the present disclosure will employ, unless otherwise indicated, conventional techniques of surgery, molecular biology, microbiology, cell biology, biochemistry, nucleic acid chemistry, and immunology, which are well known to those skilled in the art. Such techniques are explained fully in the literature, such as *Current Protocols in Molecular Biology* (F. M. Ausubel et al., eds., 1987, including supplements through 2014), and *Current Protocols in Immunology* (Horgan K and S. Shaw (1994) (including supplements through 2014). As appropriate, procedures involving the use of commercially available kits and reagents are generally carried out in accordance with manufacturer defined protocols and/or parameters unless otherwise noted.

II. DEFINITIONS

The term "diabetes" or "diabetic disorder" or "diabetes mellitus," as used interchangeably herein, refers to a disease which is marked by elevated levels of sugar (glucose) in the blood. Diabetes can be caused by too little insulin (a protein produced by the pancreas to regulate blood sugar), resistance to insulin, or both. Diabetes mellitus includes, without limitation, type 1 diabetes, type 2 diabetes, or surgical diabetes.

The term "type 1 diabetes," as used herein, refers to a chronic disease that occurs when the pancreas produces too little insulin to regulate blood sugar levels appropriately. Type 1 diabetes is also interchangeably referred to as "insulin-dependent diabetes mellitus," "IDMM," "juvenile onset diabetes," "autoimmune diabetes," and "diabetes—type 1." Type 1 diabetes is the result of a progressive autoimmune destruction of the pancreatic β-cells with subsequent insulin deficiency.

"Type 2 diabetes" (also referred to as "non-insulin-dependent diabetes mellitus" or "adult-onset diabetes") refers to a metabolic disorder in individuals who exhibit insulin resistance and who usually exhibit relative, rather than absolute, insulin deficiency. Illustrative, but non-limiting criteria for determining whether an individual has type 2 diabetes, include one or more of the following: (1) a confirmed fasting plasma glucose value of greater than or equal to 126 milligrams/deciliter (mg/dL), (2) in the presence of symptoms of diabetes, a confirmed non-fasting plasma glucose value of greater than or equal to 200 mg/dL (3) with an oral glucose tolerance test (by administering 75 grams of anhydrous glucose dissolved in water, in accordance with World Health Organization standards, and then measuring the plasma glucose concentration 2 hours later), a confirmed glucose value of greater than or equal to 200 mg/dL.

"Surgically induced diabetes" or "surgical diabetes" refers to diabetes cause by some surgical procedure, such as when surgery on the pancreas impacts its ability to produce insulin either permanently or temporarily.

As used herein, the term "insulin-producing cell" refers to any cell which can produce or has the potential to produce and secrete insulin similar to that produced and secreted by a beta cell of the islets of Langerhans in the pancreas. Preferably, the secretion of insulin by an insulin-producing cell is also regulated in a similar fashion to the regulation of insulin secretion by a beta cell in situ; for example, insulin secretion should be stimulated by an increase in the glucose concentration in the solution surrounding the insulin-producing cell.

As used herein, "a cell derived from a parathyroid gland" means a cell isolated from the tissue of a parathyroid gland. In some embodiments, a cell derived from a parathyroid gland is a $CD34^+$ cell. In other embodiments, the cell derived from parathyroid gland are $CD45^-CD34^+$. In another embodiment, the cell derived from parathyroid gland secrets one or more pre-angiogenic substances such as, but not limited to, VEGF, PDGF, and angiopoietin. In another embodiment, the cell derived from parathyroid gland secrets one or more hormones (such as, but not limited to, GABA, leptin, serotonin, PTH and PTHrP).

As used herein, a "$CD34^+$ cell" refers to a cell that expresses the progenitor cell antigen CD34, also known as CD34 antigen, which is a protein that in humans is encoded by the CD34 gene (OMIM: 142230; NM_001025109; NP_001020280). In some embodiments of the disclosure, the CD34+ cell can be derived from a parathyroid gland. In some embodiments, the CD34+ cell can be derived from a stem cell. In some embodiments, the CD34+ cell can be derived from a pluripotent stem cell (PSC) such as, for example, an induced pluripotent stem cell (iPSC) or an embryonic stem cell (ESC). In some embodiments, the CD34+ cell can be derived from other types of progenitor cells.

As used herein, "pancreatic endocrine progenitor/precursor cells," "pancreatic endocrine progenitor cells," and "endocrine precursor cells" are all intended to refer to cells derived from mammalian stem cells that are capable of differentiating into endocrine cells of the islets of Langerhans, including but not limited to functioning insulin-producing beta cells, glucagon-producing alpha cells, somatostatin producing delta cells and pancreatic polypeptide-producing PP cells. In the cell composition of the present disclosure, the endocrine progenitor cells differentiate at least into functioning beta cells, alpha cells and delta cells when co-transplanted into an individual to treat insulin deficient diabetes or they generate functioning insulin-producing beta cells and other islet endocrine hormone producing cells in vitro upon further differentiation. Such cells can express at least one of the following markers: NGN3, NKX2.2, NEUROD, ISL-1, PAX4, PAX6, or ARX.

The term "pancreatic progenitor", "pancreatic precursor," or "progenitor pancreatic cell" are used interchangeably herein and refer to a stem cell which are less differentiated than pancreatic endocrine progenitor cells, and are capable of forming all cell types of the pancreatic lineage, including pancreatic endocrine cells, pancreatic exocrine cells or pancreatic duct cells. Under the right conditions, they can form the subset of pancreatic endocrine cells, e.g., beta cells that produce insulin; alpha cells that produce glucagon; delta cells (or D cells) that produce somatostatin; and/or PP cells that produce pancreatic polypeptide.

Two or more cells (such as, but not limited to, an insulin-producing cell, a stem cell-derived mature or progenitor pancreatic cell, a parathyroid gland-derived cell) or tissues (such as pancreatic tissue, such as a beta islet or parathyroid gland tissue) are "co-transplanted" or "co-introduced" into an individual when they transferred from a culture vessel or a donor (such as, a living donor or a cadaver) into an individual. Co-transplantation, as used herein, can further include the steps of isolating a stem cell, partially or completely differentiating the stem cell (such as into an insulin-producing cell) and transferring the stem cell into an individual. Co-transplantation can involve transferring an insulin-producing cell, a stem cell-derived mature or progenitor pancreatic cell, a parathyroid gland-derived cell, and/or a $CD34^+$ cell into an individual by injection of a cell suspension into an individual, surgical implantation of a cell mass into a tissue or organ (such as, for example, subcutaneously or intramuscularly) of the individual, or perfusion of a tissue or organ with a cell suspension. The route of co-transplantation will be determined by the need for the cell to reside in a particular tissue or organ and by the ability of the cell to find and be retained by the desired target tissue or organ. In the case where a transplanted cell is to reside in a particular location, it can be surgically placed into a tissue or organ or simply injected into the bloodstream if the cell has the capability to migrate to the desired target organ.

As used herein, "therapeutically effective amount" refers to the material or amount of material which is effective to prevent, alleviate, or ameliorate one or more symptoms or signs of a disease or medical condition (such as, diabetes mellitus), produce clinical improvement, delay clinical deterioration, and/or prolong survival of the individual being treated for the disease or medical condition.

As used herein, a "subject" or an "individual" or a "patient" includes animals, such as human (e.g., human subjects) and non-human animals. The term "non-human animals" includes all vertebrates, e.g., birds, e.g., mammals, e.g., rodents, e.g., mice, such as non-human primates (e.g., simians), e.g., sheep, dogs, cats, horses, cows, etc.

As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions. In some embodiments, the pharmaceutically acceptable carrier is a non-naturally occurring substance. In other embodiments, the pharmaceutically acceptable carrier is a sterile isotonic saline solution.

As used herein, the term "protein" includes polypeptides, peptides, fragments of polypeptides, and fusion polypeptides.

As used herein, a "nucleic acid" refers to two or more deoxyribonucleotides and/or ribonucleotides covalently joined together in either single or double-stranded form.

Unless specifically stated or obvious from context, as used herein, the term "or" is understood to be inclusive.

Unless specifically stated or obvious from context, as used herein, the terms "a", "an", and "the" are understood to be singular or plural.

It is understood that aspects and embodiments of the present disclosure include "comprising," "consisting," and "consisting essentially of" aspects and embodiments.

Unless defined otherwise herein, all technical and scientific terms used herein have the same meaning as commonly understood by one of ordinary skill in the art to which this disclosure pertains.

III. COMPOSITIONS

The compositions disclosed herein can include 1) an insulin-producing cell or a stem-cell derived mature or progenitor pancreatic cell and 2) a cell derived from a parathyroid gland (PTG) or a $CD34^+$ cell (such as, but not limited to, a stem cell-derived $CD34^+$ cell). The compositions can be used in the treatment of diabetes mellitus (such as, but not limited to, type 1, type 2, or surgical diabetes mellitus).

A. Insulin-Producing Cells

In some embodiments, the insulin-producing cell is a component of a pancreatic islet. Pancreatic islets or islets of Langerhans are the regions of the pancreas that contain its endocrine (e.g., hormone-producing, such as, but not limited to, insulin-producing) cells. The pancreatic islets constitute 1 to 2% of the pancreas volume and receive 10-15% of its blood flow. There are about 3 million islets distributed in the form of density routes throughout the pancreas of a healthy adult human, each of which measures an average of about 0.1 mm in diameter. Each is separated from the surrounding pancreatic tissue by a thin fibrous connective tissue capsule which is continuous with the fibrous connective tissue that is interwoven throughout the rest of the pancreas. The combined mass of the islets is 2 grams. Islets of Langerhans can also form superstructures called islet clusters surrounding large blood vessels. The roundness of islets along the pancreas has also been quantified as an index of sphericity. Islets closest to the spherical form are mainly found in the tail of the pancreas, whereas the least-spherical islets are found in the neck of the pancreas. Islet cells can include one or more of alpha cells (which produce glucagon), beta cells (which produce insulin and amylin), delta cells (which produce somatostatin), PP cells (gamma cells or F cells which produce pancreatic polypeptide) and/or epsilon cells (which produce ghrelin).

Pancreatic islets for use in the compositions and methods disclosed herein can be isolated via a number of ways known in the art. For example, islets can be isolated from donor pancreata by a mechanically-enhanced enzymatic digestion using commercially available enzymes such as collagenase. The pancreas used for islet isolation can be human (such as from one or more donor cadaver(s) to provide for allotransplantation of islets) or non-human (such as, without limitation, porcine pancreata to provide for xenotransplantation of islets).

In other embodiments, the insulin-producing cells can be beta cells, which make up 65-80% of the cells in the islets. The primary function of a beta cell is to produce, store, and release insulin upon glucose stimulation. Beta cells can respond quickly to spikes in blood glucose concentrations by secreting some of their stored insulin while simultaneously producing more. Isolation of beta cells is routine in the art and can be accomplished, for example, by fluorescence-activated cell sorting (FACS) using fluorescently labeled probes which bind to markers expressed on the surface of beta cells (see, e.g., U.S. Pat. No. 9,526,749, the disclosure of which is incorporated by reference in its entirety). As with the case with isolated islets, the source of beta cells used in the methods and compositions disclosed herein can be human or non-human (e.g., porcine).

In further embodiments, the insulin-producing cells for use in the methods and compositions disclosed herein can be derived from a stem cell. Committed lineages of stem cells for use in the present disclosure refer to the step in differentiation of stem cells (such as a pluripotent stem cell or a stem cell with a committed pancreatic cell fate) into pancreatic beta cells which involves the sequential commitment of an initially more pluripotent cell to a functional insulin-producing cell. For example, initially, pluripotent stem cells differentiate via mesendoderm into definitive endoderm. The definitive endoderm then commits towards a foregut cell fate, then to a pancreatic cell fate, and these cells, in turn, differentiate towards an endocrine pancreatic cell fate, after which they form immature beta cells and finally mature beta cells.

Figure 16:
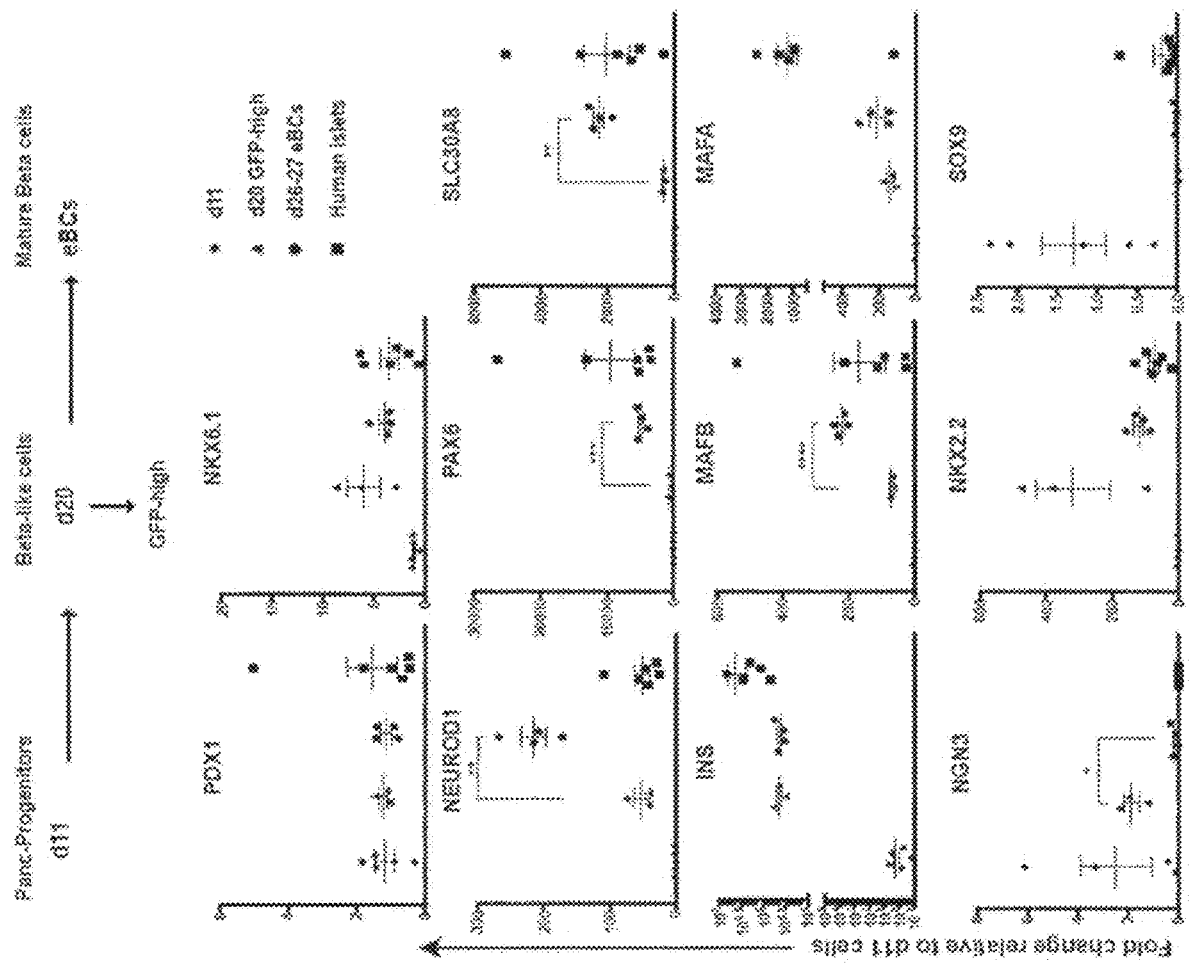
FIG. 16 depicts gene expression in insulin-producing cells from human islets, from cells sorted from SCIPCs (d20 GFP-high), and from eBCs.

The stem cell-derived insulin-producing cells contemplated for use in the methods and compositions disclosed herein include beta cells at various stage of differentiation from progenitors, to immature beta cells, to mature fully differentiated beta cells (e.g., islets from mouse, adult porcine and human donors). Accordingly, in some embodiments, the insulin-producing cell is a Stem-Cell-derived Insulin-Producing Cell (SCIPC). SCIPCs are human pluripotent stem cells (hPSC)-derived β-like cells that are monohormonal NKX6.1+/C-peptide+ double positive cells that also express certain markers found in mature β cells and package insulin into secretory granules. They are partially functional. They show modest response to glucose challenges in vitro in static assays but fail to rapidly secrete insulin in dynamic perifusion assays, indicative of an absent first phase insulin secretion. They also do not show robust calcium flux responses to glucose. These cells secrete human insulin into the serum of mice two weeks after transplantation in a glucose-regulated manner. These cells can be generated without genetic modification and in large numbers (billions of cells). Insulin-producing cells sorted from SCIPCs express similar levels of transcription factors, such as PDX1 and NKX6.1, in comparison to human islets. However, they express lower levels of critical maturation factors, including PAX6, MAFB and MAFA, and higher levels of progenitor markers NGN3 and NKX2.2, compared to human islets (FIG. 16). SCIPCs also express significantly lower levels of the Zinc transporter, SLC30A8, critical for insulin packaging within granules. Moreover, levels of insulin transcripts are lower in SCIPCs than in human islets. While SCIPCs include insulin-producing beta cells, SCIPCs can also contain, without limitation, mesenchymal/endothelial cells and neural cells. SCIPCs contemplated for use in the methods and compositions disclosed herein are human in origin. Further information regarding the characterization and culturing of SCIPCs can be found in Pagliuca et al., *Cell.* 2014; 159:428-439; Rezania et al., *Nat. Biotechnol.* 2014; 32:1121-1133; Russ et al., *EMBO J.* 2015; 34:1759-1772, and International Patent Application Publication No. WO2017019702, the disclosures of which are incorporated by reference herein in their entireties.

SCIPSs, however, possess limited functionality. The insurmountable challenge in the field so far has been to induce maturation of stem cell derived beta-like cells in vitro. Ideally these mature beta cells will secrete insulin in response to dynamic changes in glucose concentrations in addition to various physiological features of human islets. Recently, mature beta cells have been generated that are 92% identical to native human beta cells (see FIG. 14 and discussion in Example 7). These cells are generated by isolating and aggregating immature beta-like cells into 100 μm sized islet-like clusters called enriched Beta-clusters (eBCs). The coalesced eBCs display superior functional properties in vitro in all assays analyzed, including dynamic glucose stimulated insulin secretion (GSIS), $Ca^{2+}$ signaling, response to sulfonylurea secretagogues, and mitochondrial activity, when compared with SCIPCs. Also, these functional and mature eBC can be generated purely under in vitro cell culture conditions. Further, eBCs are functional as early as three days post-transplantation in mice as are adult human islets, a feat that has not been reported of cells generated using prior protocols. Most importantly, and in contrast to SCIPCs, eBC-grafts examined eight months post-transplant release large amounts of C-peptide and lack tumorous or cystic structures, tissues that can arise from progenitors/uncommitted stem cells that are present in SCIPCs. Consequently, in other embodiments, the insulin-producing cell is an eBC. While eBCs include insulin-producing beta cells, they also contain, without limitation, glucagon-expressing progenitors to alpha cells, somatostatin-expressing progenitors to delta cells, supporting cell types including mesenchymal/endothelial cells and neural cells. In summary, eBCs contain pancreatic endocrine committed cells that can further mature into all islet cell types upon transplantation. eBCs contemplated for use in the methods and compositions disclosed herein can be human or non-human (e.g., porcine or murine) in origin. Further information regarding eBCs can be found in International Patent Application Publication No. WO2017177163, the disclosure of which is incorporated by reference herein in its entirety.

In other embodiments, the insulin-producing cells for use in the methods and compositions disclosed herein can be one or more of a mature beta cell, an immature beta cell, and/or stem cell/progenitor-derived pancreas or endocrine progenitor cell.

B. Parathyroid Gland Cells and Tissue

The cell derived from a parathyroid gland (PTG) for use in the compositions and methods disclosed herein can include whole PTG tissue or individual cells derived from PTG tissue (for example, cells obtained following enzymatic digestion of PTG tissue). PTG removal and autotransplantation or allotransplantation is a well-known technique in the art and is commonly used to treat hypoparathyroidism following bilateral thyroid surgery with high transplant success rates (~93%; see Barczyński et al., 2017, *Gland Surg.* 6(5): 530-536). PTG cells and PTG-derived tissue can be implanted extrahepatically, such as subcutaneously or intramuscularly, form successful grafts, and continue to produce parathryroid hormones and other secreted substances.

In some embodiments, the cell derived from a PTG for use in the compositions and methods disclosed herein is derived from the parathyroid gland of an individual being treated for diabetes mellitus (e.g., the transplantation is an autotransplantation). Parathyroid autografts can be placed heterotopically in the subcutaneous (SQ) space or in a muscle. Different methods of parathyroid autotransplantation have been described including the techniques of slicing, mincing, and injecting a solution of suspended parathyroid tissue in saline into the muscle (see Barczyński et al., 2017, *Gland Surg.* 6(5): 530-536 and Lo, *ANZ J Surg* 2002; 72:902-7, incorporated by reference herein). In some embodiments, the cell derived from a PTG is obtained from cryopreserved tissue from the individual being treated for diabetes mellitus while in other embodiments the cell derived from a PTG is from freshly removed PTG tissue. Autotransplanted PTG has the added benefit of not causing the adverse immune reactions that can be associated with allotransplantation or xenotransplantation of tissue.

In other embodiments, the cell derived from a PTG for use in the compositions and methods disclosed herein is derived from sources of PTG that are not derived from the individual being treated for diabetes mellitus (e.g., the transplantation is an allotransplantation) Parathyroid allotransplantation is common in the art and is typically performed in patients with permanent hypoparathyroidism when cryopreserved parathyroid tissue is not available for grafting. Currently, allotransplantation of cultured parathyroid cells without immunosuppression is available in selected patients as an alternative to treatment with calcium and vitamin D3 in the management of permanent hypoparathyroidism (see Barczyński et al., 2017, *Gland Surg.* 6(5): 530-536). In some embodiments, the PTG cells or tissue used in conjunction with the compositions and methods disclosed herein is human or non-human (e.g., porcine) in origin.

C. $CD34^+$ Cells

In some embodiments, the cell derived from a PTG is a $CD34^+$ cell. CD34 (also known as CD34 antigen) is a protein that in humans is encoded by the CD34 gene and is a cell surface glycoprotein which functions as a cell-cell adhesion molecule. It may also mediate the attachment of stem cells to bone marrow extracellular matrix or directly to stromal cells. The CD34 protein is a member of a family of single-pass transmembrane sialomucin proteins that show expression on early hematopoietic and vascular-associated tissue. However, little is known about its exact function. PTG contains a small population of $CD34^+$ cells that promote angiogenesis and hormone secretion after transplantation. These cells produce proangiogenic factors including, without limitation, VEGF, PDGF, and angiopoietin within hours after heterotopic placement. $CD34^+$ cells also become mature endothelial cells that support neovascularization within days. Parathyroid hormone (PTH) has the ability to recruit vascular progenitor cells via the CXCL12 mediated pathway. As such, and without being bound to theory, these proangiogenic properties of PTG can be harnessed to support islet grafts by accelerating revascularization in extrahepatic sites. Moreover, hormones such as (without limitation) PTH, PTH related peptide (PTHrP) and GABA, produced by CD34⁺ cells, have pro-survival effects on islets.

Other sources of CD34⁺ cells contemplated for use in the methods and compositions disclosed herein include, without limitation, bone marrow, umbilical cord blood, placenta, embryonic stem cells (ESC), pluripotent stem cells (PSCs), blood precursor cells, parathyroid gland (PTG) precursors, mesoderm precursors, or endoderm precursors.

Accordingly, in some particular embodiments of the present disclosure, the CD34⁺ cells of the disclosed methods are derived from stem cells, including CD34⁺ cells derived from embryonic stem cells (ESC), and/or CD34⁺ cells derived from pluripotent stem cells (PSC). As used herein, the term "pluripotent stem cell" or "PSC" refers to a cell that has the ability to reproduce itself and can be differentiated into two or more differentiated cell types. The pluripotent stem cells suitable for the methods disclosed herein generally can be any pluripotent stem cells known in the art. Both embryonic stem cells and non-embryonic stem cells are useful. In some embodiments, the CD34⁺ cells are derived from embryonic stem cells (ESCs). As used herein, the term "embryonic stem cell" or "ESC" refers to a cell isolated from a five to seven day-old embryo. In some embodiments, CD34⁺ cells are derived from induced pluripotent stem cells (iPSCs). As used herein, the term "induced pluripotent stem cell" or "iPSC" refers to an ESC-like cell derived from adult somatic cells. iPSCs have very similar characteristics to ESCs, but avoid the ethical concerns associated with ESCs, since iPSCs are not derived from embryos. Instead, iPSCs are typically derived from fully differentiated adult cells that have been "reprogrammed" back into a pluripotent state. Since iPSCs can be derived directly from adult tissues, they not only bypass the need for embryos, but can be made in a patient-matched manner, which means that each individual could have their own pluripotent stem cell line. These unlimited supplies of autologous cells could be used to generate transplants without the risk of immune rejection. Several strategies, techniques, and procedures for generating pluripotent stem cells are known in the art. More information in this regard can be found in, for example, Lewandowski J. and Kurpisz M. Review: *Techniques of Human Embryonic Stem Cell and Induced Pluripotent Stem Cell Derivation*; Arch Immunol Ther Exp (Warsz). 2016; 64(5): 349-370. CD34⁺ cells can be identified and isolated by any means known in the art such as, but not limited to, techniques such as FACS and immuno-magnetic cell sorting. In some embodiments, CD34⁺ cells do not express pericyte markers (such as, ALP and NG2CSP) and mesenchymal markers (such as, CD105 and CD90). In other embodiments, CD34⁺ cells express markers associated with endothelial progenitors (such as, CD146, laminin, isolectin and vWFVIII).

Stem cell technology holds the promise of providing a renewable novel class of therapeutics for regenerative medicine. Currently, while there have been major advances in the in vitro differentiation of various cells and tissue types from pluripotent stem cells (PSC), engraftment often poses significant barriers to realizing the full potential of stem cell-based therapies. This challenge is exemplified in the efforts of applying PSC-derived insulin-producing cells for the treatment of type 1 diabetes, where the majority of the islets die shortly after transplantation in preclinical models and in patients. As described in greater detail below, the present disclosure demonstrates the generation of PSC-derived CD34+ cells, from both human embryonic and induced pluripotent stem cells, and its application as a renewable cellular source for promoting engraftment of therapeutic cells and tissues (e.g., Examples 23 and 29). In particular, these PSC-derived CD34+ cells were found to resemble the PTG-derived VEPC in that they have similar cell surface phenotype (e.g., CD45⁻CD34⁺CD146⁺CD31⁻) as PTG-VEPC and capable of preserving beta cell mass after co-transplantation and they rapidly form tubules in an in vitro angiogenesis assay (see, e.g., Example 23). In addition, co-transplantation of stem-cell-derived VEPC (scVEPC) promotes engraftment of PSC-derived pancreatic beta cells (see, e.g., Example 29). Furthermore, in an effort to simulate islet organogenesis during embryonic development, where pancreatic endocrine cells coalesce with blood vessels to form islets, PTG-derived CD34+ VEPC were co-clustered with PSC-derived insulin-producing cells. The resulting vascular beta and islet clusters (vBCs) showed increased basal C-peptide production and improved dynamic glucose response in vitro to the level similar to that of human islets. Moreover, vBCs produced with scVEPC and PTG-VEPC also showed immediate and persistent enhanced survival after transplantation when compared to beta cell clusters formed without VEPC. Notably, the enhanced survival was found to be associated with robust neovascularization of the grafts. Lastly, vBCs showed enhanced in vivo function in diabetes protection in a mouse model.

Taken together, some embodiments and aspects of the present disclosure provide a process to produce PSC-derived VEPC and further demonstrate their application in enhancing stem-cell-derived beta cell replacement therapy in preclinical models. One of ordinary skill in the art upon reading the disclosure will readily appreciate that the scVEPC and their use in co-transplantation or formation of composite tissue as disclosed herein may be applied to other regenerative therapies. Without being bound to any particular theory, it is believed that the approaches disclosed herein are particularly suitable for supporting engraftment of highly vascularized tissue such as pancreatic islets. The islets can generally be from any suitable sources and may be, for example, from allogeneic deceased donors, autologous islets removed during pancreatectomy, PSC-derived beta and islet cells and clusters, or islets from xenogeneic source. As will be discussed in greater detail below, these scVEPC may be co-transplanted or co-aggregated with pancreatic beta cells before transplantation.

As will be further discussed in the Examples section and for purposes of the methods disclosed herein, co-transplantation of intact PTG tissue, PTG-derived cells, PTG-derived CD34⁺ progenitor cells, or a stem cell-derived CD34⁺ cell can be used to support extrahepatic engraftment of human islets and stem cell derived beta cells for the treatment of diabetes mellitus.

D. Pharmaceutical Compositions

Also provided herein are pharmaceutical compositions that contain an insulin-producing cell (such as, but not limited to a SCIPC or eBC), a cell derived from a parathyroid gland (such as any PTG cell described herein, including stem cell-derived PTG cells) and/or a CD34⁺ cell and one or more pharmaceutically acceptable excipients.

A pharmaceutical composition is formulated to be compatible with its intended route of administration. The co-transplanted insulin-producing cells and PTG-derived cells and/or CD34⁺ cells disclosed herein may be administered through a parenteral route. Examples of parenteral routes of administration include, for example, intramuscular, intravenous, intradermal, subcutaneous, transdermal (topical), transmucosal, intra-peritoneal and intraomental administration. Solutions or suspensions used for parenteral application can include the following components: a sterile diluent such as water for injection, saline solution, tissue preservation solution, heparin containing isotonic fluid (Plasma-LyteA, normal saline), CMRL 1066, +50 mL 25% human serum albumin containing heparin, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). Agents that increases viscosity, such as sodium carboxymethyl cellulose, sorbitol, dextran, hydrogel, or fibrin, may be included to facilitate cell aggregation. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. Suitable carriers include physiological saline, bacteriostatic water, Cremophor EL™. (BASF, Parsippany, N.J.), or phosphate buffered saline (PBS). In all cases, the composition should be sterile and should be fluid to the extent that easy syringability exists. It should be stable under the conditions of preparation and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, isotonic agents can be included, for example, sugars, polyalcohols such as mannitol, sorbitol, sodium chloride in the composition.

Pharmaceutical formulations for parenteral administration include aqueous solutions of active compounds. For injection, the pharmaceutical compositions of the present disclosure may be formulated in aqueous solutions, preferably in physiologically compatible buffers such as Hank's solution, Ringer' solution, Wisconsin Solution, Plasma-LyteA, or physiologically buffered saline. Aqueous injection suspensions may contain substances which increase the viscosity of the suspension, such as sodium carboxymethyl cellulose, sorbitol, dextran, hydrogel, or fibrin. Human serum albumin may be included to support cell viability. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

After the pharmaceutical compositions disclosed herein have been prepared and are formulated in an acceptable carder, they can be placed in an appropriate container and labeled for treatment of an indicated condition with information including amount, frequency and method of administration. In some embodiments, any of the pharmaceutical compositions disclosed herein are loaded into a syringe (such as a pre-filled syringe), a catheter, or a cannula prior to administration into an individual.

The data obtained from the cell culture assays and animal studies can be used in formulating a range of dosage for use in humans. The dosage of such therapy can be estimated initially from preclinical data comparing the relative potency of the new formulation with the standard formulation in animal studies. A minimal cell dose to achieve diabetes remission in animal studies can be compared between old and new formulations. In these dose-finding studies, C-peptide (a non-metabolized byproduct of insulin production) concentration at baseline and after administration of glucose can also be measured and compared between the old and new formulation. Such information can be used to more accurately determine useful doses in humans. Levels of C-peptide in plasma may be measured, for example, using enzyme-linked immunosorbent assay.

The dosages administered will vary from individual to individual; a therapeutically effective dose in humans can be estimated, for example but not limited to, by the level of enhancement of function (e.g., C-peptide concentration or minimal cell dose required for diabetes remission). Monitoring levels of co-transplanted cell introduction, the level of expression of certain genes affected by such transfer, and/or the presence or levels of the encoded product will also enable one skilled in the art to select and adjust the dosages administered. Generally, a composition including co-transplanted cells will be administered in a single dose in the range of $10^5$-$10^8$ cells per kg body weight, preferably in the range of $10^6$-$10^7$ cells per kg body weight. This dosage may be repeated as considered appropriate by the treating physician.

E. Delivery Devices

In additional aspects, the co-transplanted insulin-producing cells (such as any of the insulin-producing cells disclosed herein) and PTG-derived and/or $CD34^+$ cells (such as any of the PTG-derived and/or $CD34^+$ cells disclosed herein) can be co-transplanted using a delivery device, such as, for example, a retrievable net-like delivery device, a 3D scaffold-based delivery device, or by encapsulation (with limited permeability for cells and macromolecules) of the co-transplanted cells or tissue. Use of delivery devices in the methods and compositions disclosed herein facilitates easy monitoring and removal of insulin-producing grafts transplanted into the individual either subcutaneously, intramuscularly, or by any other method known in the art Preferred devices may have certain characteristics which are desirable but are not limited to one or a combination of the following: i) comprised of a biologically derived or synthetic biocompatible material that functions under physiologic conditions, including pH and temperature; ii) releases no toxic compounds harming the co-transplanted cells delivered with the device; iii) promotes secretion or release of a biologically active agent or macromolecule (e.g., insulin, PTH, VEGF, GABA) across the device; iv) promotes long-term stability of the delivered cells or tissues; v) promotes vascularization; vi) comprised of membranes or housing structure that is chemically inert; vii) provides stable mechanical properties; viii) maintains structure/housing integrity (e.g., prevents unintended leakage of toxic or harmful agents and/or cells (such as neoplastic cells); ix) is refillable and/or flushable; x) is mechanically expandable; xi) provides a means for retrieving and/or monitoring the co-transplanted cells or tissue from the host tissue; xi) is easy to fabricate and manufacture; and xii) can be sterilized.

In some embodiments, the delivery device can be made of biologically derived or synthetic polymers and adopts a mesh or lattice-like configuration in which the co-transplanted cells are placed. This configuration permits newly formed blood vessels to reach the co-transplanted cells, thereby improving the likelihood of survival in nutrient and oxygen poor transplantation sites (such as the SQ space or IM). Additionally, the mesh or lattice configuration of the delivery device permits removal or monitoring of the co-transplanted cells or tissue following co-transplantation. Some exemplary, non-limiting examples of biologic derived materials that can be used in conjunction with the disclosures provided for herein include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized cellulose, mussel-based adhesive, poly (amino acid), agarose, polyetheretherketones, amylose, hyaluronan, hyaluronic acid, whey protein, cellulose gum, starch, gelatin, silk, or other material suitable to be mixed with biological material and introduced into a transplantation site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals. Synthetic materials can be any synthetic material that can be useful in an implantable surgical device, such as a biocompatible polymeric material or a biocompatible non-polymeric synthetic material. Non-limiting examples of useful synthetic polymeric materials include thermoplastic polymeric materials such as polyolefins (e.g., polypropylenes), polyurethanes, acetel materials, Teflon® materials, and the like; thermoset materials such as silicones; and materials that are otherwise curable, e.g., that can be cured by ultraviolet radiation or chemical reactions, including curable materials such as curable urethanes, epoxies, acrylates, cyanoacrylates, and the like. Any of these materials may be homopolymers, copolymers, or a blend or other combination of homopolymers, copolymers, or both. Other suitable synthetic materials include, without limitation, metals (e.g., silver filigree, tantalum gauze mesh, and stainless steel mesh).

In another embodiment, the delivery device can be made of biologically derived or synthetic polymers and adopts a three dimensional scaffold support structure in which to embed the co-transplanted cells. This device also permits newly formed blood vessels to reach the co-transplanted cells, thereby improving the likelihood of survival in nutrient and oxygen poor transplantation sites (such as the SQ space or IM). Additionally, the scaffold support configuration of the delivery device permits removal or monitoring of the co-transplanted cells or tissue following co-transplantation. In some embodiments, the scaffold is gel-like in nature. Examples of gel-like scaffolds for use in the methods and compositions disclosed herein include, without limitation, fibrin, collagen, alginate, matrigel, and gelatin. In other embodiments, the scaffold is fibrous in nature and each fiber of the scaffold comprises a biocompatible material. Optionally, the biocompatible material comprises a material selected from the group including, but not limited to, an absorbable material, a non-absorbable material and combinations thereof. Further, the three-dimensional matrices can be formed of a biodegradable, non-degradable, or combination of biodegradable and non-degradable materials which have been configured to produce high cell densities by allowing adequate diffusion of nutrients, hormones, growth factors, insulin, and waste as well as gas exchange, while in vitro or in vivo.

Absorbable material for use in the fiber scaffold can be selected from the group including, but not limited to, polyglycolic acid (PGA), polylactic acid (PLA), polyglycolide-lactide, polycaprolactone, polydioxanone, polyoxalate, a polyanhydride, a poly(phosphoester), catgut suture, collagen, silk, chitin, chitosan, hydroxyapatite, bioabsorbable calcium phosphate, hyaluronic acid, elastin, and combinations thereof. Non-absorbable material for use in 3-D fiber scaffolds can be selected from the group including, but not limited to, polypropylene, polyester, polytetrafluoroethylene (PTFE), expanded PTFE (ePTFE), polyethylene, polyurethane, polyamide, nylon, polyetheretherketone (PEEK), polysulfone, a cellulosic, fiberglass, an acrylic, tantalum, polyvinyl alcohol, carbon, ceramic, a metal, and combinations thereof. The fiber scaffold can be made from biocompatible fibers, including textured fibers that provide a much lower bulk density filling than non-texturized fiber. The low bulk density of textured fibers can provide for implantation of a significant numbers of cells.

In yet another embodiment, the co-transplanted cells or tissue are encapsulated prior to transplantation into the individual. For example, such devices can house therapeutically effective quantities of cells within a semi-permeable membrane having a pore size such that oxygen and other molecules important to cell survival and function can move through the semi-permeable membrane but the cells of the immune system cannot permeate or traverse through the pores. Similarly, such devices can contain therapeutically effective quantities of a biologically active agent, e.g., insulin, an angiogenic factor, a growth factor, a hormone and the like. Ideally, the co-transplanted cells are wholly encapsulated or enclosed in at least one internal space or are encapsulation chambers, which are bounded by at least one or more semi-permeable membranes. Such a semi-permeable membrane should allow the encapsulated biologically active substance of interest to pass (e.g., insulin, glucagon, pancreatic polypeptide and the like), making the active substance available to the target cells outside the device and in the patient's body. In some embodiments, the semi-permeable membrane allows nutrients naturally present in the subject to pass through the membrane to provide essential nutrients to the encapsulated cells. At the same time, such a semi-permeable membrane prohibits or prevents the patient's cells, more particularly the immune system cells, from passing through and into the device and harming the encapsulated cells in the device as well as prevents any potentially neoplastic cell originating in the co-transplanted cells or tissue from passing into the patient's body. For example, in the case of diabetes, this approach can allow glucose and oxygen to stimulate insulin-producing cells to release insulin as required by the body in real time while preventing immune system cells from recognizing and destroying the implanted cells. In some embodiments, the semi-permeable membrane prohibits the implanted cells from escaping encapsulation. In a further embodiment, insulin-producing cells can be encapsulated within the device while all or some of the cells derived from PTG and/or $CD34^+$ cells are co-transplanted outside of the device.

Cell permeable and impermeable membranes comprising of have been described in the art including those patents previously described above by Baxter or otherwise previously referred to as TheraCyte cell encapsulation devices including, U.S. Pat. Nos. 6,773,458; 6,520,997; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518;

5,219,361; 5,100,392; and 5,011,494, which are herein incorporated by reference in their entireties.

In some embodiments, the encapsulating devices are comprised of a biocompatible material including, but are not limited to, anisotropic materials, polysulfone (PSF), nano-fiber mats, polyimide, tetrafluoroethylene/polytetrafluoroethylene (PTFE; also known as Teflon®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes. These and substantially similar membrane types and components are manufactured by at least Gore®, Phillips Scientific®, Zeus®, Pall® and Dewal® to name a few. Further information regarding encapsulation of insulin-producing cells can be found in Nyitray et al. (*ACS Nano.*, 2015 May 14; 9(6):5675-82) and Chang et al. (*ACS Nano.* 2017 Aug. 7; 11(8):7747-57) the disclosures of which are incorporated by reference herein.

IV. METHODS

A. Methods for Treating Diabetes Mellitus

Provided herein are methods for treating diabetes mellitus (such as, but not limited to, type 1, type 2, or surgical diabetes mellitus) in an individual in need thereof. The method includes co-transplanting a therapeutically effective amount of an insulin-producing cell (such as any of the insulin-producing cells described herein) and a cell derived from a parathyroid gland (such as any of the PTG-derived cells described herein) into the individual. The insulin-producing cell can be a mature or immature stem cell-derived cell (such as an SCIPC or an eBC) or can be a pancreatic progenitor cell. The cells can be co-transplanted extra-hepatically, such as, but not limited to, subcutaneously (SQ) or intramuscularly (IM) In some embodiments, the method results in insulin production within three days (such as any of 1, 2, or 3 days or any of about 6, 12, 18, 24, 30, 36, 42, 48, 54, 60, 66, or 72 hours, inclusive of times falling in between these values) of co-transplantation. The co-transplanted insulin-producing cells can exhibit about a 10% to about an 8000%, such as about a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in survival relative to insulin-producing cells that are not co-transplanted with a cell derived from a PTG. In other embodiments, the co-transplanted insulin-producing cell and cell derived from a PTG exhibit about a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in angiogenesis at the site of co-transplantation relative to insulin-producing cells that are not co-transplanted with a cell derived from a PTG.

In some embodiments, grafts resulting from co-transplanted insulin-producing cells and cells derived from a PTG exhibit higher glucose- or mixed meal-stimulated C-peptide expression in comparison to grafts derived from transplantation of insulin-producing cells alone. C-peptide (PubChem CID: 16132309) is a short 31-amino-acid polypeptide that connects insulin's A-chain to its B-chain in the proinsulin molecule. In diabetes and other diseases, a measurement of stimulated C-peptide blood serum levels can be used to distinguish between certain diseases with similar clinical features. The co-transplanted insulin-producing cell and cell derived from a PTG can exhibit a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in stimulated C-peptide expression relative to the expression of this polypeptide when insulin-producing cells are transplanted alone. The expression levels of stimulated C-peptide produced by the graft that results from co-transplantation of insulin-producing cells and cells derived from a PTG can increase from within 3 days post-co-transplantation. Circulating stimulated C-peptide levels can range from 50-100 ng/L, 75-150 ng/L, 100-200 ng/L, 150-250 ng/L, 200-300 ng/L, or 250-350 ng/L, 500-1500 ng/L, 1000-2000 ng/L, 1500-2500 ng/L, 2000-3000 ng/L, 2500-3500 ng/L, such as any of about 50 ng/L, 60 ng/L, 70 ng/L, 80 ng/L, 90 ng/L, 100 ng/L, 110 ng/L, 120 ng/L, 130 ng/L, 140 ng/L, 150 ng/L, 160 ng/L, 170 ng/L, 180 ng/L, 190 ng/L, 200 ng/L, 210 ng/L, 220 ng/L, 230 ng/L, 240 ng/L, 250 ng/L, 260 ng/L, 270 ng/L, 280 ng/L, 290 ng/L, 300 ng/L, 310 ng/L, 320 ng/L, 330 ng/L, 340 ng/L, 350 ng/L, 400 ng/L, 450 ng/L, 500 ng/L, 550 ng/L, 600 ng/L, 650 ng/L, 700 ng/Lt, 750 ng/L, 800 ng/L, 850 ng/L, 900 ng/L, 950 ng/L, 1000 ng/L, 1500 ng/L, 2000 ng/L, 2500 ng/L, 3000 ng/L, or more, inclusive of all values falling in between these concentrations.

In further embodiments, the insulin-producing cell and cell derived from a PTG can reduced insulin needs and/or achieve insulin independence in an individual with diabetes mellitus (such as, but not limited to, type 1, type 2, or surgical diabetes mellitus) following co-transplantation. In further embodiments, 50-100%, such as 50-90%, 60-90%, 70-90%, 65-85%, or 75-100%, such as any of about 50%, 55%, 60%, 65%, 70%, 75%, 80%, 85%, 90%, 95%, or 100% (including values falling in between these percentages) of individuals achieve insulin independence, ex., has no need for exogenous insulin, following co-transplantation. In further embodiments, the individual is insulin independent 1, 2, 3, 4, 5 or more years following co-transplantation.

Also provided herein are methods for treating diabetes mellitus (such as, but not limited to, type 1, type 2, or surgical diabetes mellitus) in an individual in need thereof by co-transplantation of an insulin-producing cell and a CD34+ cell. The method can optionally include the step of isolating or deriving a CD34+ cell. CD34+ cells can be isolated or derived from PTG or a number of other sources, such as, without limitation, bone marrow, umbilical cord blood, pluripotent stem cells (PSC), blood precursor cells, parathyroid gland (PTG) precursors, mesoderm precursors, or endoderm precursors using cell isolation and separation methods that are well known in the art. The cells can be co-transplanted extra-hepatically, such as, but not limited to, subcutaneously (SQ) or intramuscularly (IM). In some embodiments, the method results in insulin production within three days (such as any of 1, 2, or 3 days or any of about 6, 12, 18, 24, 30, 36, 42, 48, 54, 60, 66, or 72 hours, inclusive of times falling in between these values) of co-transplantation. The co-transplanted insulin-producing cells can exhibit about a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in survival relative to insulin-producing cells that are not co-transplanted with a CD34$^+$ cell. In other embodiments, the co-transplanted insulin-producing cell and a CD34$^+$ cell exhibit about a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in angiogenesis at the site of co-transplantation relative to insulin-producing cells that are not co-transplanted with a CD34$^+$ cell.

In some embodiments, grafts resulting from co-transplanted insulin-producing cells and CD34$^+$ cells exhibit higher stimulated C-peptide expression in comparison to grafts derived from transplantation of insulin-producing cells alone. The co-transplanted insulin-producing cell and CD34$^+$ cell can exhibit a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%. 900%, 1000%, 1500%, 2000%, 2500%, 3000%, 3500%, 4000%, 4500%, 5000%, 6000%, 7000%, 8000% or more (including values falling in between these percentages) increase in stimulated C-peptide expression relative to the expression of this polypeptide when insulin-producing cells are transplanted alone ('e.g., in the absence of a CD34$^+$ cell). The expression levels of stimulated C-peptide produced by the graft that results from co-transplantation of insulin-producing cells and CD34$^+$ cells can increase within 3 days post-co-transplantation. Circulating stimulated C-peptide levels can range from 50-100 ng/L, 75-150 ng/L, 100-200 ng/L, 150-250 ng/L, 200-300 ng/L, or 250-350 ng/L, 500-1500 ng/L, 1000-2000 ng/L, 1500-2500 ng/L, 2000-3000 ng/L, 2500-3500 ng/L, such as any of about 50 ng/L, 60 ng/L, 70 ng/L, 80 ng/L, 90 ng/L, 100 ng/L, 110 ng/L, 120 ng/L, 130 ng/L, 140 ng/L, 150 ng/L, 160 ng/L, 170 ng/L, 180 ng/L, 190 ng/L, 200 ng/L, 210 ng/L, 220 ng/L, 230 ng/L, 240 ng/L, 250 ng/L, 260 ng/L, 270 ng/L, 280 ng/L, 290 ng/L, 300 ng/L, 310 ng/L, 320 ng/L, 330 ng/L, 340 ng/L, 350 ng/L, 400 ng/L, 450 ng/L, 500 ng/L, 550 ng/L, 600 ng/L, 650 ng/L, 700 ng/L, 750 ng/L, 800 ng/L, 850 ng/L, 900 ng/L, 950 ng/L, 1000 ng/L, 1500 ng/L, 2000 ng/L, 2500 ng/L, 3000 ng/L, or more, inclusive of all values falling in between these concentrations.

In further embodiments, the insulin-producing cell and cell derived from a PTG and/or CD34$^+$ cell can reduced insulin needs and/or achieve insulin independence in an individual with diabetes mellitus (such as, but not limited to, type 1, type 2, or surgical diabetes mellitus) following co-transplantation. In further embodiments, 50-100%, such as 50-90%. 60-90%, 70-90%, 65-85%, or 75-100%, such as any of about 50%, 55%, 60%, 65%, 70%, 75%, 80%, 85%, 90%, 95%, or 100% (including values falling in between these percentages) of individuals achieve insulin independence, e.g., has no need for exogenous insulin, following co-transplantation. in further embodiments, the individual is insulin independent 1, 2, 3, 4, 5 or more years following co-transplantation.

The cell derived from a parathyroid gland or a CD34$^+$ cell for use in the methods and compositions disclosed herein can additionally secret one or more factors that support the engraftment of the insulin-producing cells (such as any of the insulin-producing cells described herein), For example, PTG secreted factors parathyroid hormone (PTH), parathyroid hormone-related protein (PTHrP), and GABA can protect survival and differentiation of co-transplanted insulin-producing grafts, for example, under the oxygen and nutrient poor conditions found in the SQ space. Additionally, cells derived from a parathyroid gland, a stem cell or a CD34$^+$ cell for use in the methods and compositions disclosed herein can also secrete one or more pro-angiogenic factors to promote blood and nutrient delivery to co-transplanted insulin-producing grafts. These proangiogenic factors can include, without limitation, VEGF-A, and PDGF-AA. Further, cells derived from a parathyroid gland, a stem cell or a CD34$^+$ cell for use in the methods and compositions disclosed herein can also secrete one or more chemokines for stem cells and endothelial cells. These factors can include, without limitation, CCL2 and CXCL12. Lastly, cells derived from a parathyroid gland, a stem cell or a CD34$^+$ cell for use in the methods and compositions disclosed herein can differentiate into vascular endothelial cells to directly contribute revascularization of the co-transplanted insulin-producing and/or pancreatic progenitor cells grafts.

B. Methods for Engrafting an Insulin Producing Cell

Further provided herein are methods for engrafting an insulin-producing cell into an individual comprising co-transplanting an insulin-producing cell (such as any of the insulin-producing cells disclosed herein) and a cell derived from a parathyroid gland and/or a CD34+ cell (such as any of the PTG-derived or stem cell-derived CD34$^+$ cells disclosed herein) into the individual, thereby engrafting the insulin-producing cell into the individual. The insulin-producing cell can be a mature or immature stem cell-derived cell (such as an SCIPC or an eBC) or can be a pancreatic progenitor cell. The cells can be co-transplanted extrahepatically, such as, but not limited to, subcutaneously (SQ) or intramuscularly (IM). In some embodiments, the method results in insulin production within three days (such as any of 1, 2, or 3 days or any of about 6, 12, 18, 24, 30, 36, 42, 48, 54, 60, 66, or 72 hours, inclusive of times falling in between these values) of co-transplantation. The co-transplanted insulin-producing cells can exhibit about a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in survival relative to insulin-producing cells that are not co-transplanted with a cell derived from a PTG and/or a CD34$^+$ cell. In other embodiments, the graft exhibits about a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in angiogenesis at the site of co-transplantation relative to grafts that are not co-transplanted with a cell derived from a PTG and/or a CD34$^+$ cell.

In some embodiments, grafts resulting from co-transplanted insulin-producing cells and cells derived from a PTG and/or a CD34$^+$ cell exhibit higher stimulated C-peptide expression in comparison to grafts derived from transplantation of insulin-producing cells alone. The grafts resulting from a co-transplanted insulin-producing cell and cell derived from a PTG and/or a CD34$^+$ cell can exhibit a 10%, 15%, 20%, 25%, 30%, 35%, 40%, 45%, 50%, 55%, 60%, 65%, 70%, 75%, 80%, 85%, 90%, 100%, 200%, 300%, 400%, 500%, 600%, 700%, 800%, 900%, 1000%, 1500%, 2000%, 2500%, 3000%, 3500%, 4000%, 4500%, 5000%, 6000%, 7000%, 8000% or more (including values falling in between these percentages) increase in stimulated C-peptide expression relative to the expression of this polypeptide when insulin-producing cells are transplanted alone. The expression levels of stimulated C-peptide produced by the graft that results from co-transplantation of insulin-producing cells and cells derived from a PTG and/or a CD34+ cell can within 3 days post-co-transplantation. Circulating stimulated C-peptide levels can range from 50-100 ng/L, 75-150 ng/L, 100-200 ng/L, 150-250 ng/L, 200-300 ng/L, or 250-350 ng/L, 500-1500 ng/L, 1000-2000 ng/L, 1500-2500 ng/L, 2000-3000 ng/L, 2500-3500 ng/L, such as any of about 50 ng/L, 60 ng/L, 70 ng/L, 80 ng/L, 90 ng/L, 100 ng/L, 110 ng/L, 120 ng/L, 130 ng/L, 140 ng/L, 150 ng/L, 160 ng/L, 170 ng/L, 180 ng/L, 190 ng/L, 200 ng/L, 210 ng/L, 220 ng/L, 230 ng/L, 240 ng/L, 250 ng/L, 260 ng/L, 270 ng/L, 280 ng/L, 290 ng/L, 300 ng/L, 310 ng/L, 320 ng/L, 330 ng/L, 340 ng/L, 350 ng/L, 400 ng/L, 450 ng/L, 500 ng/L, 550 ng/L, 600 ng/L, 650 ng/L, 700 ng/L, 750 ng/L, 800 ng/L, 850 ng/L, 900 ng/L, 950 ng/L, 1000 ng/L, 1500 ng/L, 2000 ng/L, 2500 ng/L, 3000 ng/L, or more, inclusive of all values falling in between these concentrations.

In further embodiments, grafts resulting from co-transplantation of the insulin-producing cell and cell derived from a PTG and/or a CD34+ cell can reduced insulin needs and/or achieve insulin independence in an individual with diabetes mellitus (such as, but not limited to, type 1, type 2, or surgical diabetes mellitus) following co-transplantation. In further embodiments, 50-100%, such as 50-90%, 60-90%, 70-90%, 65-85%, or 75-100%, such as any of about 50%, 55%, 60%, 65%, 70%, 75%, 80%, 85%, 90%, 95%, or 100% (including values falling in between these percentages) of individuals achieve insulin independence, e.g., has no need for exogenous insulin, following co-transplantation. In further embodiments, the individual is insulin independent 1, 2, 3, 4, 5 or more years following co-transplantation.

In some embodiments of any of the methods disclosed herein, the insulin-producing cells (such as mature or immature stem cell-derived insulin-producing cells) are cultured under conditions and supplemented with nutrients to improve survival rates. It has been shown in vitro that nutrient deprivation and hypoxia can independently kill mature insulin producing cells such as human islets. Combination of nutrient deprivation and hypoxia that occurs during ischemia act additively to kill mature insulin producing cells. Stem cell derived pancreatic precursor cells and immature insulin producing cells are more resistant to nutrient deprivation and hypoxia alone, but these two factors act synergistically to kill pancreatic precursor cells and immature insulin producing cells in vitro. However, generating pancreatic precursor cells and immature insulin producing cells under physiological oxygen tension of 5% can confer hypoxia resistance without affecting differentiation or function. As such, in some embodiments, insulin-producing cells are cultured prior to co-transplantation in an atmosphere having any of 1%, 2%, 3%, 4%, 5%, 6%, 7%, 8%, 9%, or 10% oxygen concentration. In another embodiment, the co-transplanted insulin-producing cells are supplemented during and/or after transplantation with one or more amino acids. In some non-limiting embodiments, the amino acids are alanine and glutamine. Further information regarding pre-culturing insulin-producing cells under low oxygen conditions prior to transplant and nutritional supplementation of these cells can be found in Faleo, et al., *Stem Cell Reports*, 2017, 9(3):807-19, the disclosure of which is incorporated by reference herein in its entirety.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The discussion of the general methods and compositions given herein is intended for illustrative purposes only. Other alternative methods, compositions, and alternatives will be apparent to those of skill in the art upon review of this disclosure, and are to be included within the spirit and purview of this application.

EXAMPLES

Example 1

Co-Transplantation of Isolated Mature Mouse Islets with Syngeneic Mouse Parathyroid Gland This Example shows that co-transplantation of isolated mouse islets with syngeneic mouse parathyroid gland increases the survival of islet graft compared to islets alone in the SQ and IM site in syngeneic recipients.

Materials and Methods

Mice: C57BL/6 (B6), B6.MIP-Luc, and NOD.Cg-Prkdcscid Il2rgtm1Wj1/SzJ (NSG) mice were housed and bred at the University of California, San Francisco Animal Barrier Facility. All animal procedures were performed under approved protocols and in accordance with ethical guidelines by the Institutional Animal Care and Use Committee (IACUC) at the University of California, San Francisco.

Parathyroid gland isolation: Mouse parathyroid glands (PTGs) were surgically removed from syngeneic B6 mice or allogeneic BALB/C mice. Mice were anesthetized under standard isoflurane anesthesia. Mideline sternotomy was performed and full blood volume (~2 mL) was aspirated via right ventriculotomy. Via midline neck incision, sternocleidomastoid muscle and salivary glands were reflected laterally exposing thyroid and parathyroid. Parathyroid tissue was identified via retention of blood in capillary rich PTG. PTG was isolated and removed and washed in PBS. PTG was placed in same islet medium (RPMI base) and used for transplant within 4-6 hours after removal.

Co-transplantation technique: Hand-picked islets were carefully aspirated off the bottom of a 6 well culture plate. Hand-picked mouse parathyroid glands were carefully aspirated next using same pipette tip. A length of PE50 tubing was attached to the pipette tip using a small silicone adapter tubing. Recipient mice were anesthetized, shaved, and cleaned. For subcutaneous transplants a small (5 mm) incision is made in flank and carried bluntly down to subcutaneous tissue. The pipette and cannula was inserted into the subcutaneous tissue and islets are pipetted into the pocket. For intramuscular transplants, a 5 mm incision on anterior side of hind limb medial to femoral vascular pedicle was performed. Using sharp and blunt dissection, a space was created between anterior and posterior muscle groups extending medial to origin of iliopsoas muscle. Islets or stem cells plus parathyroid gland cells were pipetted into space and stitch was used to re-approximate anterior and posterior muscle groups. Skin was closed with running silk suture.

Bioluminescent Imaging: Mice transplanted with luciferase-expressing cells were injected IP with 15 mg/Kg D-luciferin solution (Goldbio Biotechnology, St. Louis, MO) 8 minutes before imaging on a Xenogen IVIS 200 imaging system (Perkin Elmer, Waltham, MA). Signals were acquired with 5-minute exposure and analyzed using the Living Image analysis software (Xenogen Corp., Alameda, CA). Circular regions of interests (ROI) were manually drawn to encircle all the signals and same sized circles were used for the analysis of all data points within the same experiment to ensure consistency in signal quantification. Photons emitted over the time of exposure within the ROI were quantified. Identical protocol was strictly followed for sequential imaging of the same mice over a period of up to one month to ensure comparability of assay performance over time. Background signals in an area distal to the transplants were similarly analyzed and found to be consistent over time.

Results

Figure 1B:
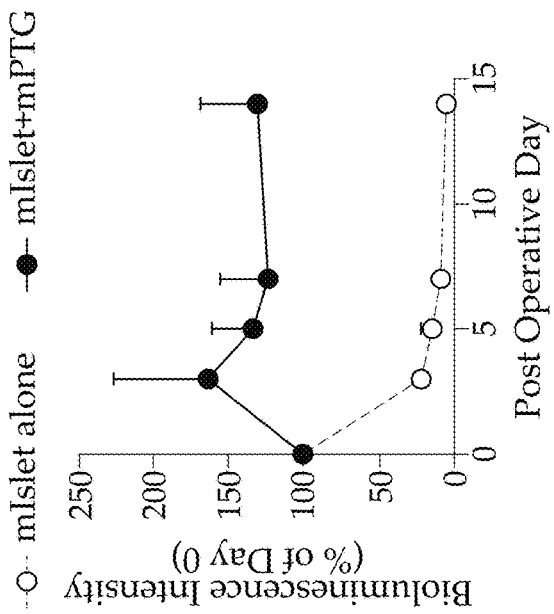
FIG. 1B depicts representative bioluminescence images of B6.MIP.Luc islets with and without B6 parathyroid gland transplanted into non-diabetic B6 albino mice subcutaneously (IM, n=3 per group). Bioluminescent intensity of islet grafts over time is shown as percentage of day 0.

B6 albino MIP.Luc islets were isolated and either cotransplanted with syngeneic B6 mouse parathyroid glands or alone in B6 albino mice. Viability, defined as percent of bioluminescence compared to day 0 bioluminescence, was significantly increased in PTG co-transplanted mice compared to control. Both subcutaneous (SQ; FIG. 1A) and intramuscular (IM; FIG. 1B) PTG co-transplanted mice groups demonstrated ~150% of Day 0 bioluminescence compared to ~25% in IM and 10% in SQ. Notably, after day 5 bioluminescence began to significantly increase until day 14 in both co-transplanted groups. Without being bound to theory, the increase in signal is likely not due to increased islet mass because adult mouse islets have limited proliferative potential. In bioluminescence imaging, luciferase substrate, luciferin, is transported to the transplanted beta cells via blood and diffusion in the extravascular space. On Day 0, the islets are stripped of vascular connections in the graftbed, thus the luciferin substrate relies more on the less efficient diffusion process to reach only some of the islet grafts. Thus, day 0 signal is likely an underestimation of the graft mass. Again, without being bound to theory, bioluminescence intensity greater than 100% from day 5 to day 14 in PTG co-transplanted groups is thus likely an effect of neoangiogenesis allowing luciferin to reach the beta cells more efficiently to reveal islets not previously seen on Day 0. Light emission catalyzed by luciferase requires ATP that is only present intracellularly in live cells. Thus the robust luciferase signal seen in PTG co-transplant groups also demonstrate preserved islet viability likely due to the efficient neovascularization. In the islet alone groups, neovascularization is less efficient, which not only prevent the visualization of the graft using luciferase imaging, but also starve the islets leading to their death. Thus, even when the graft is vascularized at later time, there are much less viable cells left.

Example 2

Autotransplantation, Allotransplantation and Xenotransplantation of Parathyroid Gland in the SQ and IM Site This Example demonstrates successful autotransplantation, allotransplantation and xenotransplantation of PTG both subcutaneously and intramuscularly in mice.

Materials and Methods

Parathyroid gland isolation was performed as above.

Immunohistochemistry: Tissue-bearing islets and stem-cell-derived beta cell grafts were fixed in paraformaldehyde (Sigma), incubated overnight in 30% sucrose (Sigma), before being embedded in tissue-Tek® OCT (Sakura Finetek, Torrance, CA). A polyclonal rabbit anti-PTH antibody (1:100, AB40630, Cambridge, MA) was applied overnight and Alexa Fluor® 488 goat anti-rabbit IgG (1:200, Invitrogen) was incubated for 1 hour. Images were taken using Leica SP5 upright confocal (Leica Microsystem, Buffalo Grove, IL) and processed with Imaris software (Bitplane, Concord, MA).

Blood PTH measurement: human PTH analyses were performed by measuring an aliquot of mouse serum with commercially available ELISA kits (human PTH ELISA, Quidel).

Results

Currently in the literature, human parathyroid gland has been transplanted into immunodeficient mice in the muscle of a mouse with confirmed engraftment but never in a SQ site. Further, no literature has described autotransplantation or allotransplantation of mouse parathyroid gland in SQ or IM sites. In order to establish this novel co-transplantation model, proof-of-concept experiments were performed and demonstrated engraftment of mouse parathyroid gland in IM and SQ sites with stable vascularity and engraftment by histology at 6 weeks (FIG. 2A). It was further confirmed that engraftment of human PTG xenotransplantation into the SQ space of immunodeficient mice after 6 weeks by histology as well as by near human physiologic levels of human parathyroid hormone (PTH) in the blood of the transplanted mice at selected time points in both SQ and IM groups (FIG. 2B and FIG. 2C).

Example 3

Co-Transplantation of Immature Stem-Cell-Derived Insulin-Producing Cells (SCIPC) with Cryopreserved hPTG Increases Survival of Graft Compared to SCIPC Alone in SQ and IM Sites in NSG Mice The advent of large-scale in vitro differentiation of human stem cell-derived insulin-producing cells (SCIPC) has brought us closer to treating diabetes using stem cell technology. However, decades of experiences from islet transplantation show that ischemia-induced islet cell death after transplant severely limits the efficacy of the therapy. Recent publications, show that more than half of SCIPC die shortly after transplantation. Nutrient deprivation and hypoxia acted synergistically to kill SCIPC in vitro and in vivo. This Example demonstrates that co-transplantation of PTG with SCIPC in the SQ and IM resulted in preservation of transplanted grafts in comparison to significant islet loss with SCIPC alone grafts.

Materials and Methods

Parathyroid gland isolation, co-transplantation technique, and bioluminescent imaging were performed as above. After receiving whole parathyroid gland from operative surgeon in sterile cryovial, the tissue is brought back to lab for sterile processing. Under sterile conditions, parathyroid tissue from tube is placed in Petri dish. With sterile blade, PTG tissue is minced with blade until 1 mm×1 mm or smaller pieces is obtained. Add 4 mL RPMI, 0.5 ml DMSO, 0.5 ml patient sera from centrifuged blood from intra-op draw into cryovial with minced tissue. Tissue is place in −80° C. freezer. Samples can be used for cry allo-transplantation within two years of cryopreservation. After that time, tissue can be used for research purposes only.

SCIPC generation: Human embryonic stem cell line containing a GFP gene knocked into the endogenous insulin locus, MEL1$^{INS-GFP/wt}$ (Micallef et al., 2012; PMID:

22120512), was maintained as described (Russ et al., 2015; PMID: 25908839). Suspension-based differentiations were carried out as described previously (Russ et al., 2015) with modification of the last differentiation stages. Cultures were incubated in DMEM (Gibco) containing 25 mM glucose, 1:100 B27 (StemCell Technologies), 50 ng/ml EGF (RnD Systems), and 50 ng/ml KGF (RnD Systems) for days 9 and 10. Thereafter, clusters were incubated in DMEM (Gibco) containing 25 mM Glucose supplemented with 1:100 B27 (StemCell Technologies), 1:100 non-essential amino acids (Gibco), 1 mM N-Acetyl-L-Cysteine (Sigma), 10 µg/ml Heparin Sodium Sulfate (Sigma), 10 µM Zinc Sulfate heptahydrate (Sigma), 10 µM ALK inhibitor 2 (Axxora), 2 µM T3 (3,3',5-Triiodo-L-thyronine sodium salt) (Sigma), 500 nM LDN-193189 (Stemgent), 1 µM Gamma-Secretase inhibitor (XXi) (Millipore), 2 µM Bay K 8644 (Tocris), and 0.5 mM 2-Phospho-L-ascorbic acid (Sigma). Medium was changed daily by aspirating approximately 5 ml followed by addition of 5 ml fresh media.

Results

Co-transplantation of PTG with SCIPC in the SQ and IM space resulted in preservation of transplanted grafts (~150%-SQ, ~200%-IM; FIG. 3A and FIG. 3B) in comparison to significant islet loss with SCIPC alone grafts (~40%-SQ, ~50%-IM; FIG. 3A and FIG. 3B) after 14 days (p<0.05). As explained in Example 1 above and without being bound to theory, the increase in signal is thought not to be due to increased SCIPC mass but instead to neoangiogenesis.

Example 4

Co-Transplantation of SCIPC with Cryopreserved hPTG Increases Graft Function In Vivo Compared to SCIPC Alone in SQ and IM Sites This Example demonstrates that co-transplantation of stem cell-derived insulin-producing cells with human parathyroid gland (hPTG) increases the insulin-producing graft function in mice.

Materials and Methods

Parathyroid gland isolation, SCIP derivation, co-transplantation technique, and immunohistochemistry were performed as above.

Human C-peptide measurement: human C-peptide analyses were performed by measuring an aliquot of mouse serum with commercially available ELISA kits (human C-peptide cat. Alpco).

Results

SCIPC+PTG co-transplanted grafts demonstrated significantly higher C-peptide, a surrogate of insulin, production when compared to SCIPC alone grafts at all time points in SQ and IM sites. A repeating phenomenon in IM and SQ sites was an initial surge in C-peptide after week 1 followed by a steady drop in weeks 2 and 3 (data not shown). By week 4, C-peptide levels began to rise, possibly due to beta cell differentiation from surviving progenitors and this trend continued to week 10. At week 10, the highest C-peptide levels near 300 pg/L were obtained in the IM site (FIG. 3C). The IM site had higher absolute values for C-peptide than SQ at all timed points.

Example 5

Co-Transplantation of SCIPC with Cryopreserved hPTG Increases Angiogenesis of Graft Compared to SCIPC Alone PTG is known to induce prompt revascularization of the graft after auto and allo-transplantation in the IM and SQ sites with early vessel formation seen at 5 days and full neovascularization of graft by 12 days. As such, it was hypothesized that co-transplantation of PTG would help support the prompt vascularization of the SCIPC graft. This Example demonstrates that co-transplantation of stem cell-derived insulin-producing cells with human parathyroid gland (hPTG) results in increased blood supply to the graft compared to grafts generated with stem cell-derived insulin-producing cells alone.

Materials and Methods

Islet isolation: Mouse islets were isolated as previously (Szot et al., *J Vis Exp.* 2007; (7):255). Purified islets were rested in RPMI medium overnight and healthy islets were handpicked for experiments. Human research islets provided by the UCSF DRC Islet Production Core following current standard protocols on research consented pancreas donors (Szot et al., 2009; PMID: 19920770). All human studies were approved by local ethics committees. Pancreata were procured from multiorgan cadaveric donors using cold perfusion with University of Wisconsin solution (ViaSpan, DuPont Pharmaceuticals Ltd.).

Co-transplantation technique: Settled stem-cell-derived beta cell clusters were carefully aspirated off the bottom of a 6 well culture plate. Finely chopped human parathyroid gland were carefully aspirated next using same pipette tip. A length of PE50 tubing was attached to the pipette tip using a small silicone adapter tubing. Recipient mice were anesthetized, shaved, and cleaned. For subcutaneous transplants a small (5 mm) incision is made in flank and carried bluntly down to subcutaneous tissue. The pipette and cannula was inserted into the subcutaneous tissue and islets are pipetted into the pocket. For intramuscular transplants, a 5 mm incision on anterior side of hind limb medial to femoral vascular pedicle was performed. Using sharp and blunt dissection, a space was created between anterior and posterior muscle groups extending medial to origin of iliopsoas muscle. Islets or stem cells plus parathyroid gland cells were pipetted into space and stitch was used to re-approximate anterior and posterior muscle groups. Skin was closed with running silk suture.

Immunohistochemistry analysis of grafts: Tissue-bearing grafts were fixed in paraformaldehyde (Sigma), incubated overnight in 30% sucrose (Sigma), before being embedded in tissue-Tek® OCT (Sakura Finetek, Torrance, CA). A polyclonal guinea pig anti-insulin antibody (1:100, Dako, Glostrup, Denmark), rat anti-mouse CD31 Alexa-647 (clone 390) were applied overnight and Alexa Fluor® 568 goat anti-guinea pig IgG (1:200, Invitrogen, Carlsbad, CA) was incubated for 1 hour. Images were taken using Leica SP5 upright confocal microscope (Leica Microsystem, Buffalo Grove, IL) and processed with Imaris software (Bitplane, Concord, MA).

Parathyroid gland isolation and SCIPC derivation were performed as above.

Results

As shown in FIG. 4C, six week histology sections of co-transplanted SCIPC grafts embedded near peri-fascicle neurovascular structures present evidence of mouse recipient endothelialization of the human xenograft. This is an important finding because, along with the >100% luciferase signal data described in Example 3 after 5 days, this provides further evidence of the ability of human PTG to induce robust revascularization of a SCIPC graft. A proposed mechanism of PTG's rich neoangiogenic capabilities is discussed in Examples 10, 13 and 14 in more detail below.

Example 6

Reversal of STZ-Induced Diabetes with SCIPC and Cryopreserved hPTG Co-Transplantation in IM Site This Example demonstrates that co-transplantation of stem cell-derived insulin-producing cells with human parathyroid gland (hPTG) results in reversal of diabetes in a mouse model of disease.

Materials and Methods

Parathyroid gland isolation, SCIP derivation, and the co-transplantation technique were performed as above.

Diabetes induction: A subset of mice was treated with streptozocin (STZ) to destroy endogenous mouse β-cells pre-transplant or 6 weeks after transplantation as indicated. STZ (20 mg kg$^{-1}$) was delivered by intra-peritoneal injection 5 days prior to transplant. Diabetes was defined by blood glucose >400 mg/dL, and diabetes reversal was defined by blood glucose <250 mg/dL. Blood glucose levels was periodically measured for mice fasted 2-4 h and for mice injected with 2 g kg$^{-1}$ glucose.

Results

Figure 5:
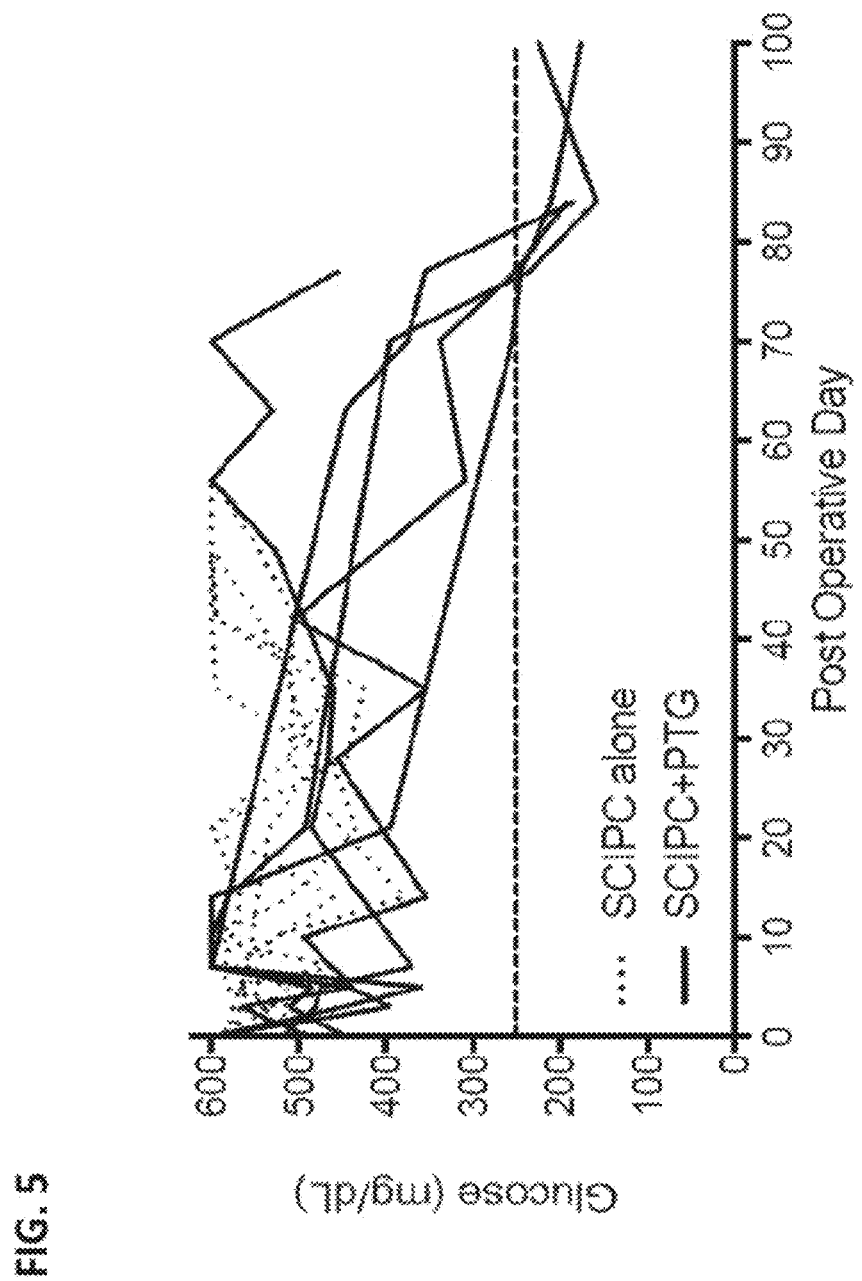
FIG. 5 depicts co-transplantation of SCIPC with human PTG leads to diabetes reversal in IM site after four weeks. STZ-induced diabetic NSG mice were transplanted with 800 SCIPC clusters with or without PTG in IM site. Diabetes was defined by pre-operative glucose >300 mg/dL. Reversal of diabetes was defined by glucose <250 mg/dL.

NSG mice were treated with STZ and diabetes was induced 3 days prior to transplant. Diabetes was confirmed by blood glucose levels >500 mg/dL in all mice. Two mice were co-transplanted with 800 clusters of SCIPCs and ¼ human PTG in the IM site as described previously. Two control mice were transplanted with 800 clusters of SCIPC alone using equivalent volume in IM site. Blood glucoses were checked twice weekly for 6 weeks. Both mice in experimental group achieved reversal of diabetes after 4-6 weeks while neither mouse in control group achieved diabetes independence (FIG. 5).

Reports of reversal of diabetes with equivalent stem cells have been published with either prevascularization or scaffold technology but never in the muscle or in stem cells without previous intervention to induce prevascularization. This is an important finding because this shows the ability of the graft to become vascularized and properly differentiate in the muscular site only with parathyroid co-transplantation.

Example 7

Figure 14A:
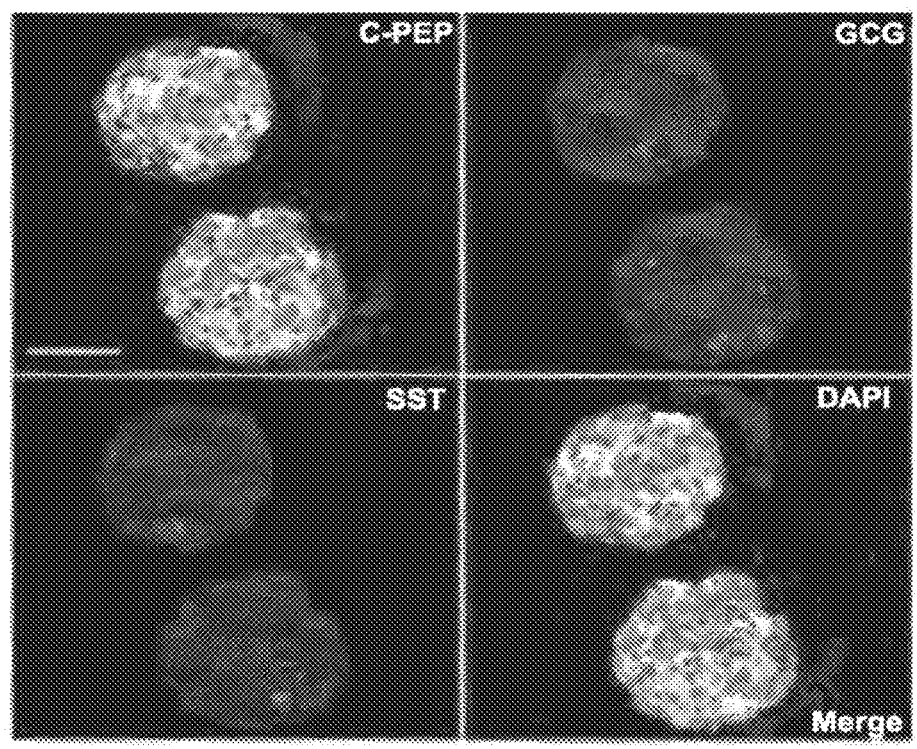
FIG. 14A depicts enriched Beta-clusters (eBC) following endocrine cell clustering and coalescence of immature β like cells derived from hESCs. The vast majority (>90%) of the cells are C-peptide+ with occasional cells double positive for glucagon or somatostatin.
Figure 14B:
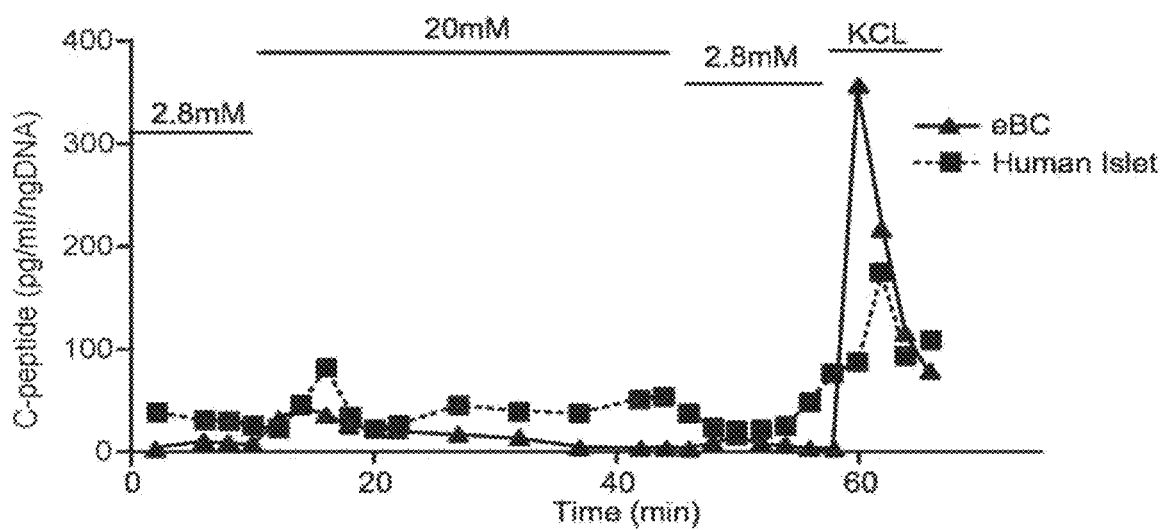
FIG. 14B depict that eBCs secrete C-peptide in response to varying levels of glucose and KCL in a similar fashion to human islets in dynamic perifusion assay.
Figure 14C:
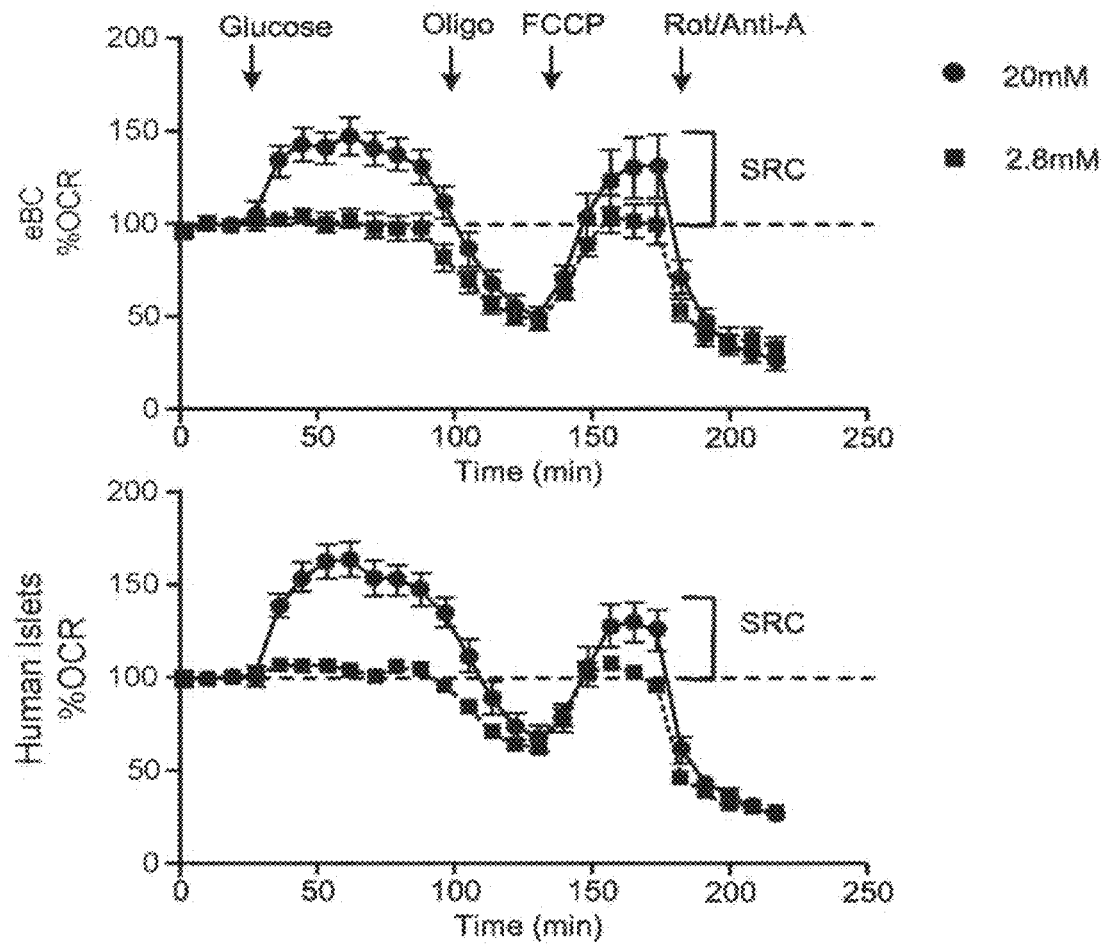
FIG. 14C depicts mitochondria of eBCs are functionally mature and increase their oxygen consumption upon glucose stimulation identically to human islets.
Figure 14D:
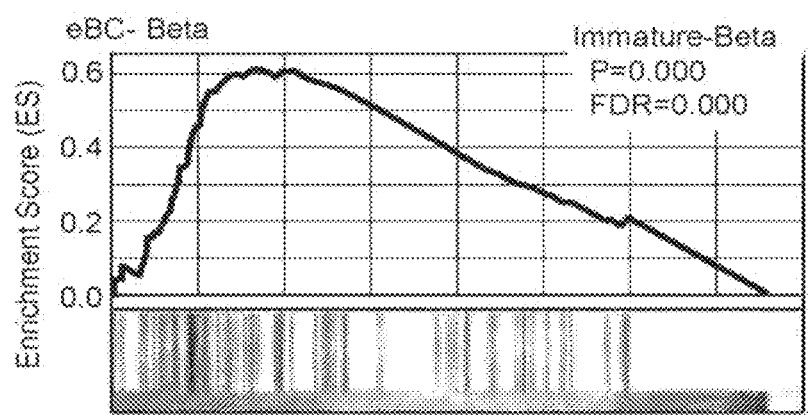
FIG. 14D depicts gene set enrichment analysis (GSEA) indicates that oxidative phosphorylation, a readout for mitochondrial function, is significantly upregulated in eBC-β cells when compared with immature β-like cells.
Figure 14E:
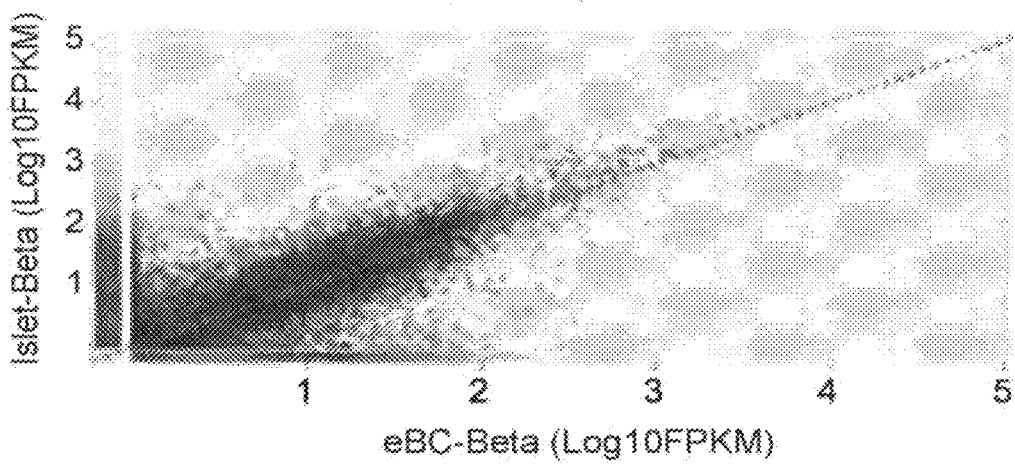
FIG. 14E depicts a scatter plot of all coding transcripts of β cells of eBC and primary β cells from human islets illustrating a high degree of correlation (Pearson correlation coefficient=0.9253, p<2.2e$^{-16}$).
Figure 14F:
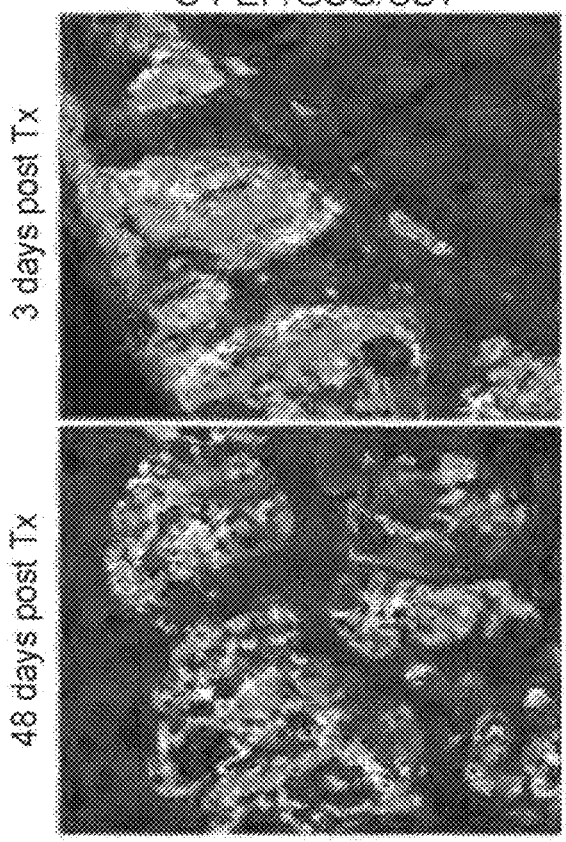
FIG. 14F depicts grafts of eBCs transplanted under the kidney capsule of NSG mice reveal robust C-peptide expression and formation of islet-like structures with intercalating glucagon and somatostatin expressing cells over time.

Co-Transplantation of Enhanced Beta Cells (eBC) with hPTG Increases Survival when Compared to eBC Alone in SQ and IM Site This Example demonstrates that enhanced beta cells exhibit increased survival when co-transplanted with hPTG. A number of groups have previously described differentiation protocols (Pagliuca et al., 2014 (PMID: 25303535); Rezania et al., 2014 (PMID: 25211370); Russ et al., 2015 (PMID: 25908839)), that allow for the reliable production of human Stem-Cell-derived Insulin-Producing Cells (SCIPCs). These insulin-producing cells, however, possess limited functionality. The insurmountable challenge in the field so far has been to induce maturation of stem-cell-derived beta-like cells in vitro. Ideally these mature beta cells will secrete insulin in response to dynamic changes in glucose concentrations in addition to various physiological features of human islets. Recently, a new protocol inspired by in vivo islet organogenesis has been developed that permits the generation of mature beta cells 92% identical to native human beta cells (FIG. 14E). The protocol includes isolation and aggregation of immature beta-like cells into 100 μm sized islet-like clusters called enriched Beta-clusters (eBCs) (FIG. 14A). The coalesced eBC display superior functional properties in vitro in all assays analyzed, including dynamic glucose stimulated insulin secretion (GSIS), Ca$^{2+}$ signaling, response to sulfonylurea secretagogues, and mitochondrial activity, when compared with SCIPCs generated with previously published protocols. Also, these functional and mature eBC can be generated purely under in vitro cell culture conditions. Further, eBCs are functional as early as three days post-transplantation in mice as would adult human islets, a feat that has not been reported of cells generated using prior protocols. Most importantly, and in contrast to SCIPCs, eBC-grafts examined eight months post-transplant release large amounts of C-peptide and lack tumorous or cystic structures, tissues that can arise from progenitors/uncommitted stem cells. The biggest long-term challenge of translating stem cell-derived cell types into therapeutic applications is to ensure efficient differentiation into only the desired cell type and to guarantee absence of cells with tumorigenic potential. Thus, eBCs stand as a safe and efficient alternative to human islets for cell therapy. Additionally, more differentiated and mature cells are more vulnerable to ischemia injury and cell death. Although eBC are more mature and functional, higher percentage of the graft die shortly after transplant, severely limiting their therapeutic potential.

Materials and Methods

Parathyroid gland isolation, co-transplantation technique, and bioluminescent imaging were performed as above.

Results

Figures 6A, 6B:
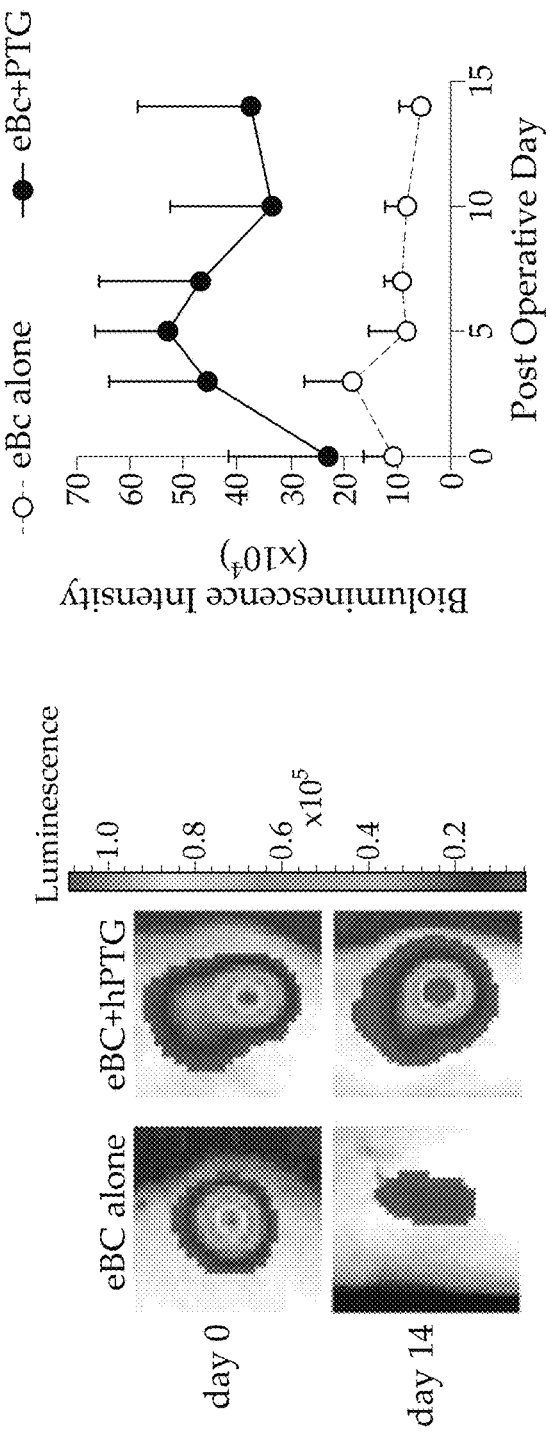
FIGS. 6A-6C depict representative images of eBC.LUC grafts with and without cryopreserved human parathyroid gland transplanted into non-diabetic NSG mice. Quantification of eBC graft mass over time using luciferase imaging. Raw bioluminescence signals are shown.
Figure 6C:

Non-diabetic immunodeficient NSG mice were co-transplanted with 200 clusters of eBC (enhanced beta clusters) and ¼ cryopreserved human PTG or 200 clusters of eBC alone in the IM and SQ in equivalent transplant volumes. Co-transplantation of eBC with PTG in the IM and SQ resulted in much improved preservation of transplanted graft in comparison to eBC alone grafts, especially in the subcutaneous space (SQ; FIG. 6B after 14 days (p<0.05). As the eBC's are closer in differentiation to mature islets, without being bound to theory, they are thought to have less ability to withstand nutrient deprivation and hypoxia in vivo leading to more severe graft loss than SCIPC and near equivalent to mature islet models (e.g., a mature mouse luciferase model). As discussed in previous Examples and without being bound to theory, the increase in signal in the co-transplant model from baseline is thought to be due to neoangiogenesis and not increased islet mass. This is same phenomenon seen in mature mouse islet and SCIPC models described above. The much improved vascularization supports high density engraftment of the eBC (FIG. 6C).

Example 8

Reversal of STZ-Induced Diabetes with eBC and Cryopreserved hPTG Co-Transplantation in IM Site This Example demonstrates that co-transplantation of eBC's with human parathyroid gland (hPTG) results in the reversal of diabetes in a mouse model of disease.

Materials and Methods

Parathyroid gland isolation, co-transplantation technique, diabetes induction, and eBC generation were performed as described above.

Results

Figure 7:
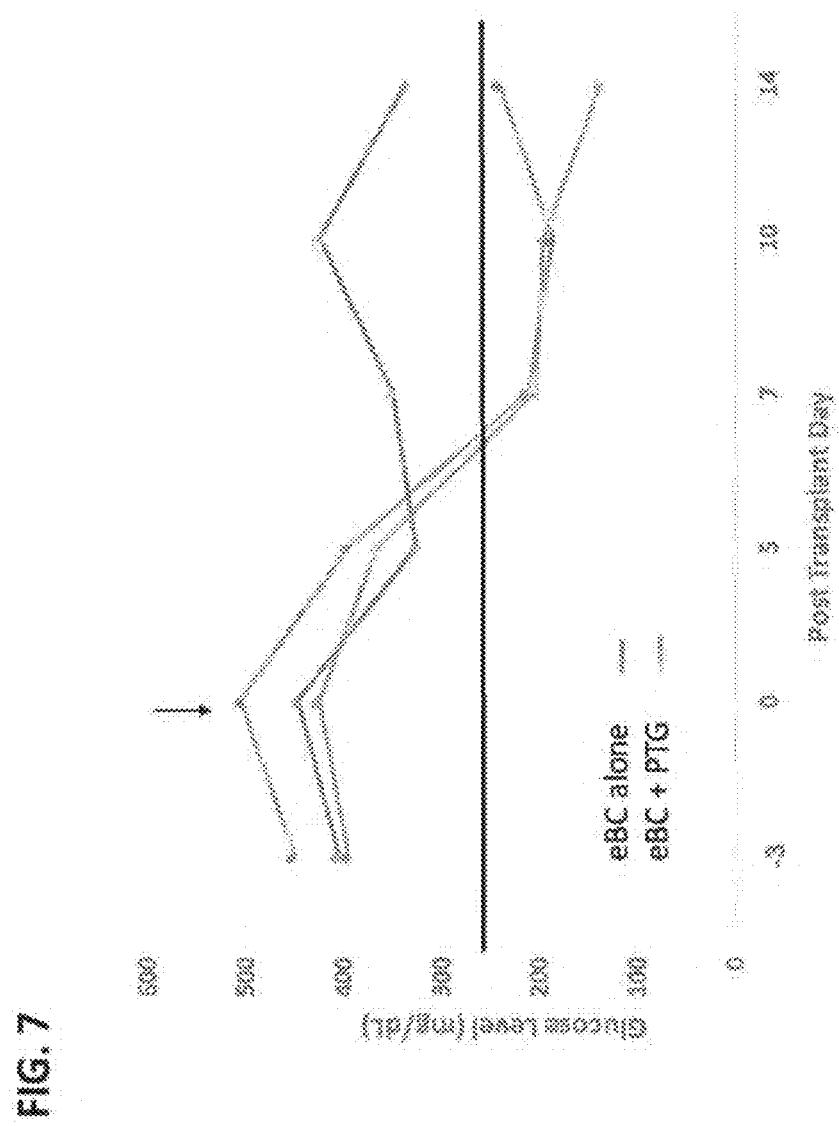
FIG. 7 depicts co-transplantation of eBC with human PTG leads to diabetes reversal in the IM site after one week. STZ-induced diabetic NSG mice were transplanted with 600 eBC clusters with or without PTG in the IM site. Diabetes was defined by pre-operative glucose >300 mg/dL. Reversal of diabetes was defined by glucose <250 mg/dL.

NSG mice were treated with STZ and diabetes was induced 3 days prior to transplant. Diabetes was confirmed by blood glucose levels >400 mg/dL in all mice. Two mice were co-transplanted with 200 clusters of eBCs and ¼ human PTG in the IM site as described previously. One control mouse was transplanted with 200 clusters of eBC alone using equivalent volume in IM site. Blood glucose levels were checked twice weekly for 2 weeks. Both mice in the experimental group achieved reversal of diabetes after 1 week while the mouse in the control group remained diabetic (FIG. 7). This is an important finding because this shows the ability of the graft to become vascularized and maintain proper differentiation in the muscular site along with parathyroid co-transplantation. This is also a critical finding because eBC's are thought to be closer to mature islets than SCIPC in differentiation and have substantial perioperative loss as seen previously in the luciferase viability model. Thus, the PTG affords peri-operative protection of the eBC graft and maintains beta cell differentiation leading to more rapid diabetes reversal than SCIPC and only slightly delayed compared to mature human islets.

Example 9

Reversal of STZ-Induced Diabetes with Isolated Human Mature Islets and Cryopreserved hPTG Co-Transplantation in SQ Site This Example demonstrates that co-transplantation of eBC's with isolated human mature islets results in the reversal of diabetes in a mouse model of disease.
Materials and Methods
Parathyroid gland isolation, co-transplantation technique, diabetes induction, and islet isolation were performed as described above.
Results
Normally humans need 1 U/kg of insulin a day to maintain normoglycemic levels. In comparison, using human insulin in a mouse (STZ diabetes induction in NSG model) requires 10 U-80 U/kg insulin due to the inefficiency of human insulin compared to mouse insulin in regulating blood glucose in mice. Because of this species mismatch in insulin potency, there has been no reported successful reversal of diabetes with human islets in the SQ site of a mouse without prior pre-vascularization or scaffolding/encapsulation manipulation. Without being bound to theory, this is likely multi-factorial with low islet survival in the SQ space subsequently further exacerbated by poor efficiency of human insulin in mouse.

Thus, as a proof of principle using one of the most difficult models for islet transplantation, PTG's peri-operative islet protection phenomenon with reversal of diabetes was further demonstrated using a suboptimal mature human islet mass, 1000 islet equivalent (IEQ), in PTG co-transplanted diabetic mice in the IM space (FIG. 8A) or 2000 IEQ in the SQ space (FIG. 8B). Co-transplantation of PTG led to long-term stable diabetes reversal in 70% of the mice in comparison to suboptimal diabetes control in 20% of mice receiving islets alone in IM site. Similarly, co-transplantation of PTG led to long-term stable diabetes reversal in 80% of the mice in comparison to 100% graft loss after SQ transplant of 2000 IEQ (FIG. 8B). A complete dose titration was performed with 250, 500, 1000 and 2000 IEQ in order to determine minimal islet mass (data not shown). Moreover, mice that received islets with PTG showed low fasting release of insulin as indicated by T0 serum C-peptide concentration before glucose challenge and high T60 serum C-peptide concentration 60 min after glucose challenge at 100 days after transplant in both IM and SQ sites. These C-peptide concentrations are in the same range of normal human levels, consistent with the data of engraftment of functional islet mass with PTG co-transplantation. This is the first demonstration of diabetes reversal in the IM and SQ space with mature human islets without pre-vascularization or scaffolding/encapsulation technologies. The importance of this finding is that the PTG affords peri-operative protection of mature human islets, which are known to be more susceptible to ischemic insults, in the nutrient poor environment of the SQ space. This result further shows the ability of the PTG to protect differentiation and viability of mature islets.

Example 10

PTG Derived $CD34^+$ Cell Isolation and Co-Transplantation with SCIPC

This Example shows that $CD34^+$ cells isolated from PTG recapitulates the phenomenon seen with whole PTG by increasing viability of SCIPC graft and increasing C-peptide production in vivo in the SQ site while the CD34− fraction affords minor protection compared to SCIPC alone in the SQ site.
Materials and Methods
Parathyroid gland isolation, SCIP derivation, bioluminescent imaging, and the co-transplantation technique were performed as above.

Figure 9A:
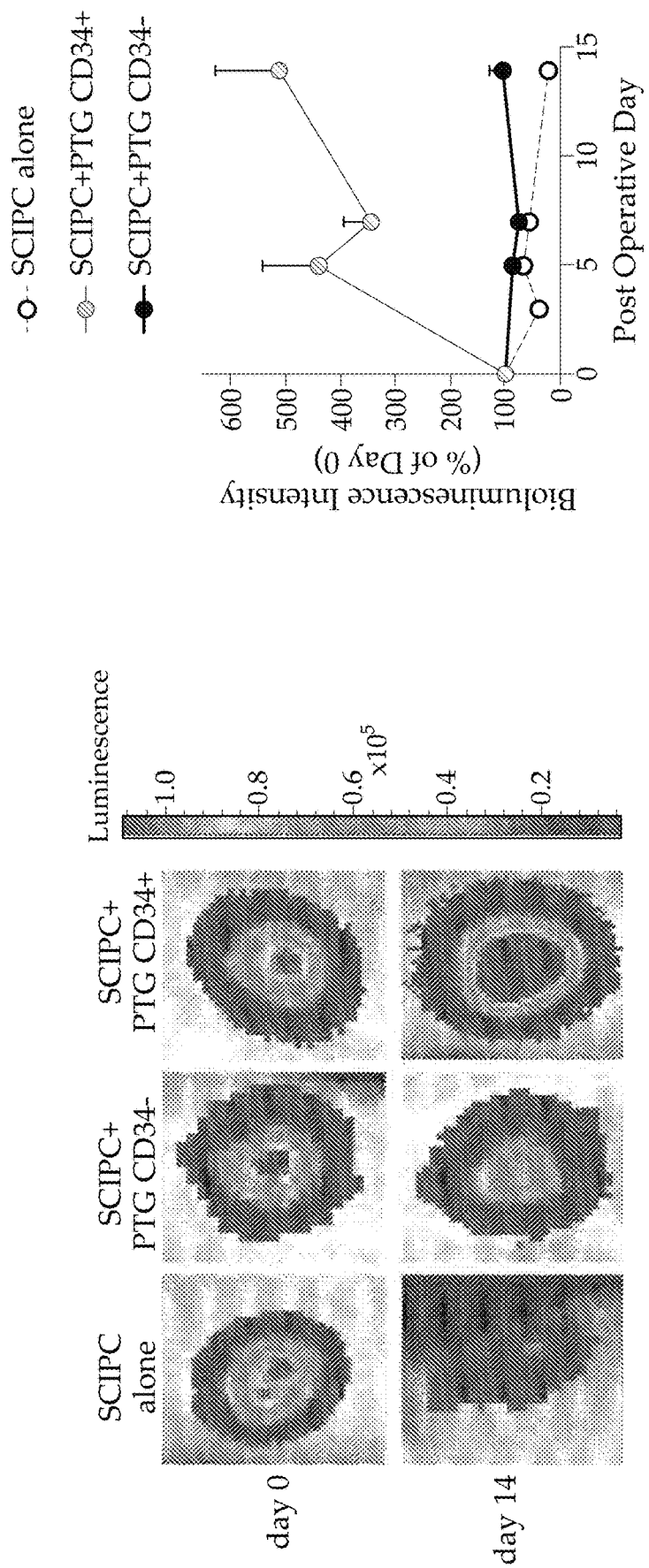
FIG. 9A depicts representative bioluminescent images of SCIPC.LUC grafts alone or with PTG derived CD34+ or CD34− sorted cells into non-diabetic NSG mice subcutaneously (SQ, n=5 per group). Quantification of SCIPC graft mass measured by luciferase bioluminescence over time is shown as percentage of day 0.
Figure 9B:
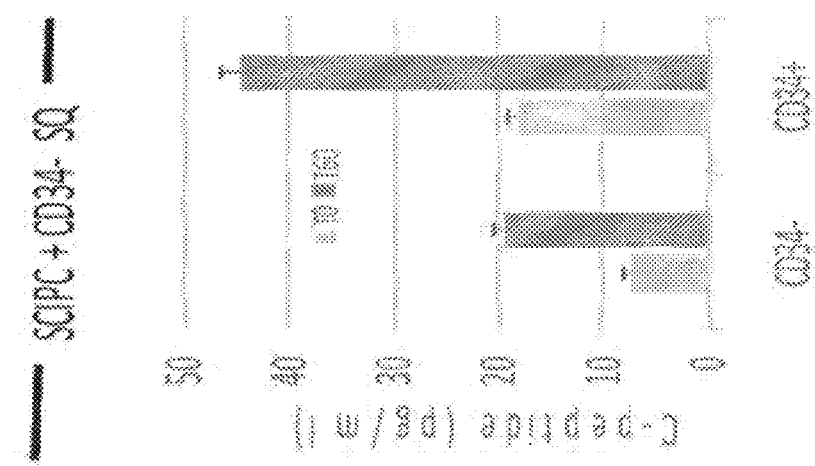
FIG. 9B depicts the levels of human C-Peptides in the serum before and after an intraperitoneal glucose bolus challenge 3 weeks after transplantation of PTG derived CD34+ and CD34− with SCIPC in the SQ space (SQ, n=3 per group; T0=Time 0 min, T60=Time 60 min relative to the time of glucose injection).
Figure 10A:
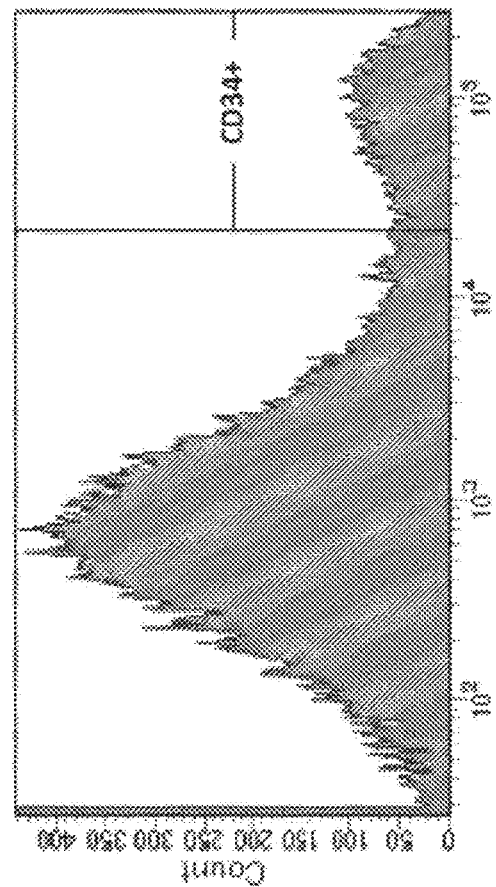
FIG. 10A depicts a representative flow cytometry profile of CD34+ cell population within PTG. Experiment replicated three times with >3% live-CD34+ cells obtained.
Figure 10B:
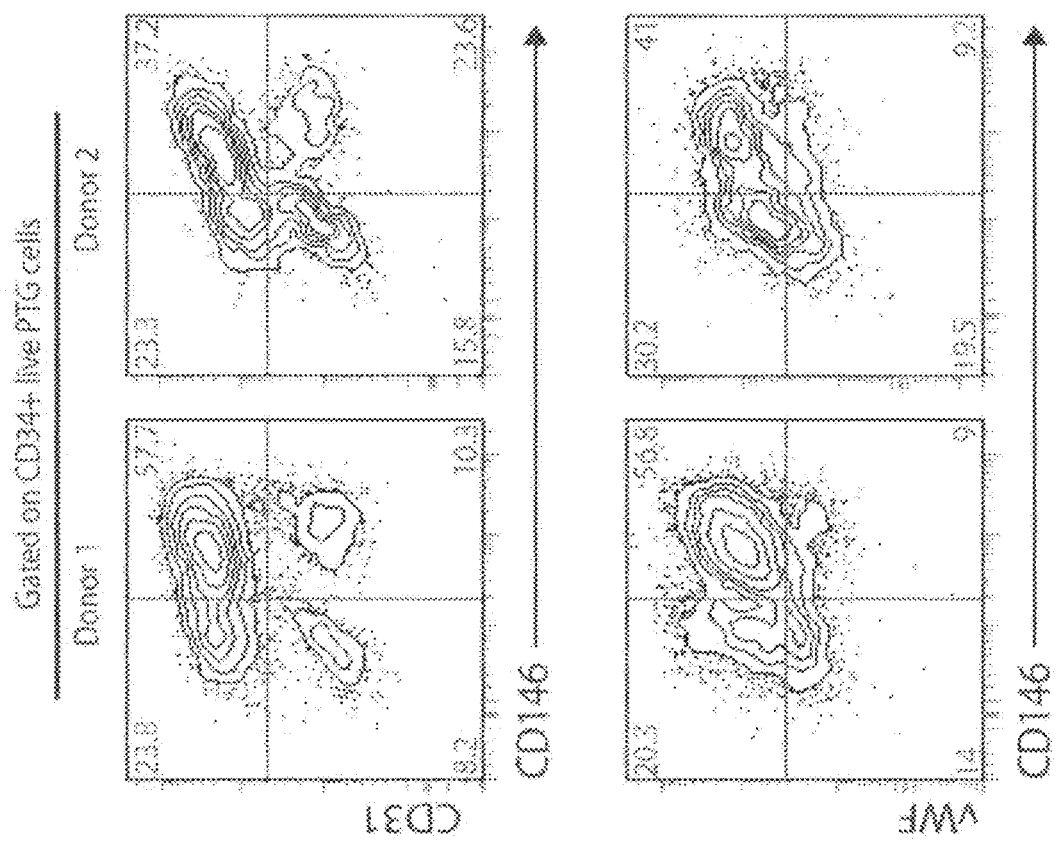
FIG. 10B depicts the expression of vascular endothelial markers on the PTG CD34+ cells. Freshly collected PTG tissue were dissociated into single cells using enzymatic digestion and labeled with fluorochrome-conjugated antibodies to human CD34, CD31, von Willebrand Factor (vWF) and CD146. Co-expression patterns of CD146 with CD31 (top panels) and CD146 with vWF (bottom panels) are shown. Results from two unrelated donors are shown.

$CD34^+$ cell isolation: Using Liberase™ (Sigma) commercial digestion protocol, PTG is made into single cell suspension. Briefly, parathyroid glands from −80 degrees C. freezer are allowed to thaw on ice. Glands are placed in 50 ml Falcon tube and pulse spin down at 1000 RPM for 1 sec. Supernatant is removed and tissue is washed with PBS twice. Digestion Media consists of 10 ml RPMI+liberase™+DNASE into Falcon tube at 37 C. Tissue is incubated for 30 min with gentle tituration with Pasteur pipette every 6 min. After 30 min, pulse spin at 1000 RPM for 1 sec. Cells are reconstituted with 10 ml MACS (PBS and BSA) buffer in 50 ml Falcon tube. 10 ml additional digestion medium to remaining tissue fractions for 30 min (using repeat of protocol outlined above). Combine samples and run over 100 µl nylon filter into 50 ml Falcon tube. Spin down at 2000 RPM for 2 min to pellet cells and resuspended in FACS buffer. Cells are then stained with CD 34-PE antibody (1:300, Miltenyi) for 30 min on ice. Cells are washed in sorting buffer and co-stained with DAPI in FACS tube. Cells are sorted into $CD34^+$ and CD34− fractions in same medium as SCIPC, eBC or islets are being cultured in and are used within 4-6 hours in co-transplantation.
Results To elucidate the mechanism of this phenomenon further, FACS was used to isolate a novel subpopulation of $CD34^+$ progenitor cells within the PTG, making up ~3-5% of the gland (FIG. 10A) To further characterize the PTG CD34+ cells, we determined the expression of CD45, CD31, and von Willebrand Factor (vWF) using flow cytometry on multiple PTG glands from unrelated donors. The CD34+ PTG cells are CD45− (data not shown) demonstrating that they are not of hematopoietic origin. In contrast, most of the cells express CD31+ and vWF demonstrating that they are endothelial cells (FIG. 10B). Importantly, more than 50% of the cells also co-express CD146, a marker of endothelial progenitor cells with the potential to form new blood vessels (vasculogenesis). To determine if a subset of PTG cells can support SCIPC engraftment and function, we performed co-transplantation of SCIPC with PTG $CD34^+$ versus PTG $CD34^-$ cells in non-diabetic NSG mice. The SCIPC+ $CD34^+$ co-transplant was superior to SCIPC+ $CD34^-$ co-transplant in promoting engraftment when compared to SCIPC transplanted alone (FIG. 9A). Furthermore, C-peptide secretion was better with CD34+ cell co-transplant than with CD34− cell co-transplant (FIG. 9B). The lower level of human C-peptide observed in these mice are because the recipient mice are not diabetic and the functioning mouse endogenous islets respond to glucose at higher threshold than human beta cells thus suppressing the human SCIPC C-peptide secretion. The results nonetheless are consistent with the engraftment data to demonstration that the human PTG CD34+ cells have most potent activity is protection pancreatic beta cells.

Previous reports further defining the PTG derived CD34$^+$ cells demonstrate that this unique population is negative for hematopoietic (CD45, CD133 and c-kit), pericyte (ALP and NG2CSP) and mesenchymal markers (CD105 and CD90). While markers of endothelial progenitors (CD146, laminin, isolectin and vWFVIII) are present on PTG derived CD34$^+$ cells.

Example 11

Human PTG-Derived CD34$^+$ Fraction Produce PTH In Vitro and In Vivo

This Example shows the further characterization of the properties and secreted factors of this CD34$^+$ population of cells derived from parathyroid gland. From previous published reports, it was known that the CD34$^+$ cells have two fates during autotransplantation: 1) they turn into mature endothelial cells to support graft revascularization; and 2) they become chief-like cells that secrete PTH and PTHrP. Thus, without being bound to theory, it is believed that the neoangiogenic properties are conserved with the CD34$^+$ population based on their ability to recruit endothelial cells through pro-angiogenic signaling and by their ability to produce pro-survival factors including PTH, PTHrP and GABA.

After FACS isolation of CD34$^+$ and CD34− cell fractions, cells were placed in RPMI based medium for 24 hours and supernatant was analyzed via Human specific PTH ELISA kit (Immutopics, San Clemente, CA). The CD34$^+$ fraction produced PTH at 12.7 pg/mL concentration while chief cell rich CD34− cell fraction produced 240.2 pg/mL on average.

Next, the CD34$^+$ population was further examined to determine if these cells could differentiate in vivo after transplantation and secrete PTH in the SQ space. After 4 weeks, the CD34$^+$ population secreted near physiologic levels of PTH (6 pg/mL) while the CD34− fraction recapitulated secretion pattern seen with whole PTG transplant outlined in Example 2 (11 pg/mL). This is the first evidence of in vivo PTH secretion by a PTG-derived CD34$^+$ only cell fraction substantially consequential for the islet and PTG co-transplantation model disclosed herein as well as for future parathyroid gland allotransplantation models. In summary, this data demonstrates the ability of the CD34$^+$ fraction to produce PTH in vitro and provides the first evidence of the ability of CD34$^+$ cells to make PTH in vivo in mouse.

Example 12

Human PTG Secreted Factors Protect Survival and Differentiation of SCIPC and eBC Grafts In Vitro Under Nutrient Deprivation and Hypoxic Conditions This Example shows that PTH, PTHrP and GABA can protect transplanted SCIPC and eBC under the conditions that mimic those found in the SC space.

Figure 11A:
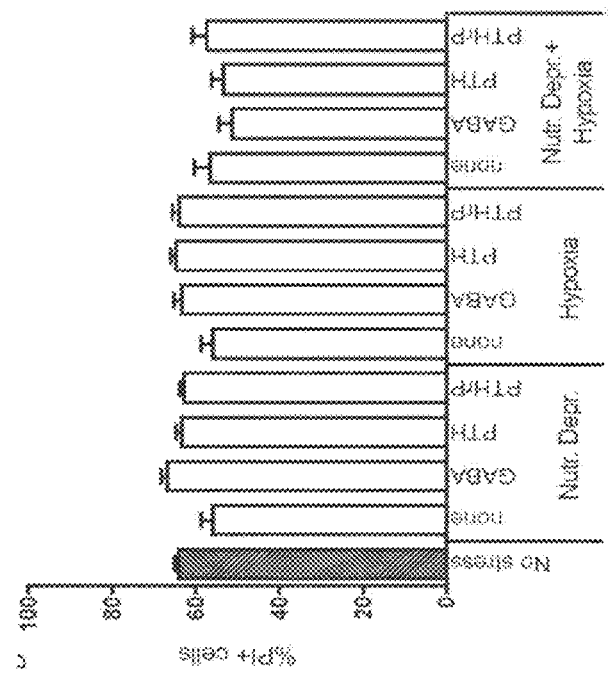
FIG. 11A depicts that addition of GABA, PTH and PTHrP, secreted by PTG, preserve SCIPC survival. SCIPC cultured for 24 hours in nutrient deprived and/or hypoxic conditions with or without GABA, PTH, and PTHrP At the end of the experiment, islet viability was measured using PI staining followed by flow cytometry.
Figure 11B:
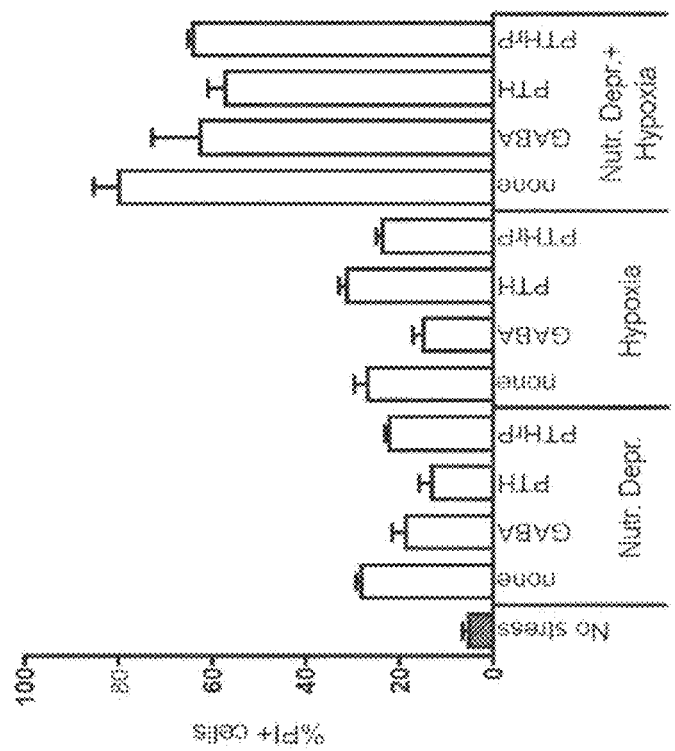
FIG. 11B depicts the effect of GABA, PTH and PTHrP on preserving insulin-producing cells after stress.
Figure 11D:
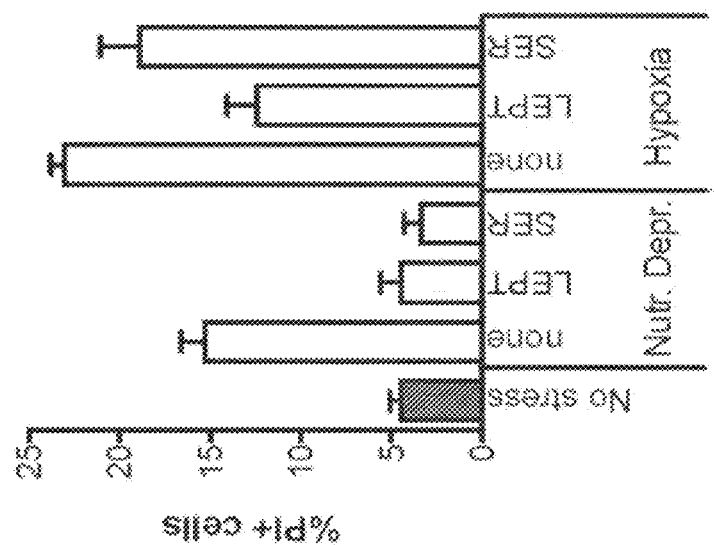
FIG. 11D depicts addition of leptin and serotonin preserves beta cell survival. Quantification of viability of eBC cultured for 24 hours in nutrient deprived and/or hypoxic conditions with or without leptin or serotonin. Islet viability measured using PI staining followed by flow cytometry.
Figure 11C:
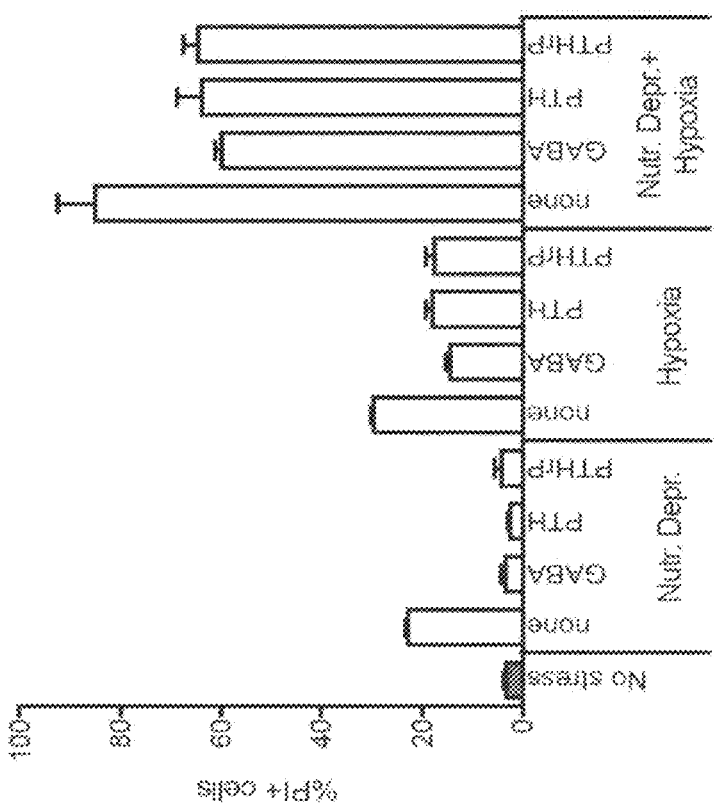
FIG. 11C depicts quantification of viability of eBC cultured for 24 hours in nutrient deprived or hypoxic conditions with or without GABA, PTH, and PTHrP.

In order to understand whether cell survival is due to secreted pro-survival or pro-angiogenic molecules, known PTG-released molecules were added to SCIPC and eBC cultures in vitro. While PTH is the main PTG-secreted hormone, previous publications also show GABA production within the PTG. GABA and PTH improve beta cell survival in nutrient deprived and/or hypoxic environment in vitro (FIG. 11A). Also, GABA, PTH, and PTHrP preferentially preserve insulin-producing cells in SCIPC and eBC (FIG. 11B and FIG. 11C). Moreover, addition of leptin and serotonin, secreted by PTG, preserves beta cell survival (FIG. 11D).

Example 13

Figure 12A:
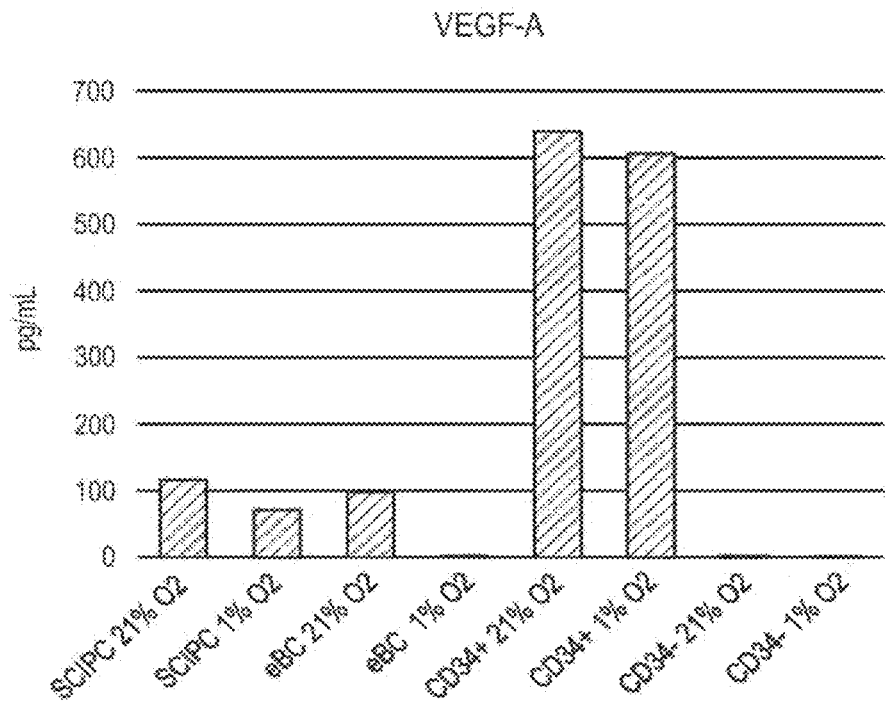
FIG. 12A depicts the release of VEGF-A by SCIPC, eBC, CD34+, and CD34− cells.
Figure 12B:
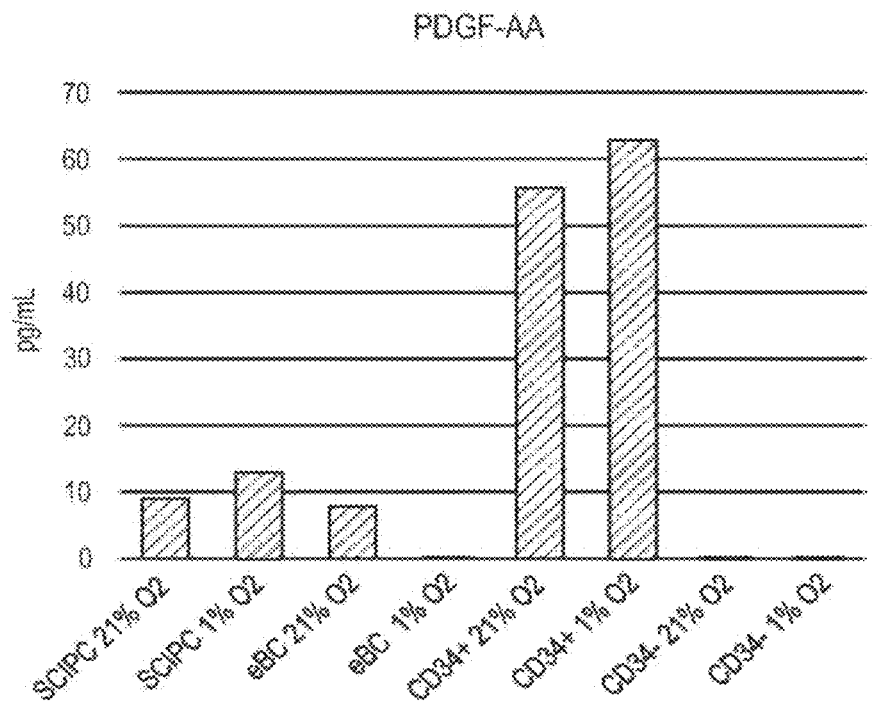
FIG. 12B depicts the release of PDGF-AA by SCIPC, eBC, CD34+, and CD34− cells. SCIPC, eBC, CD34+, and CD34− cells were cultured for 24 hours in 21% oxygen or 1% oxygen. At the end of the experiments, supernatant was collected and analyzed for human cytokines.

Mouse and Human PTG-Derived CD34$^+$ Cells Secrete Pro-Angiogenic Factors Including VEGF, PDGF and Angiopoietin In this Example, in order to understand which cell population is responsible for the protective effect at the transplant site, SCIPC, eBC, CD34$^+$, and CD34− cells were cultured in atmospheric and hypoxic environments. After 24 hours, the production of 65 cytokines was measured using multiplex Luminex assay (Evetechnologies, Calgary, Alberta Canada). VEGF-A, and PDGF-AA were among the highest secreted peptides by SCIPC, eBC, and CD34$^+$ cells but not CD34− cells (FIG. 12A and FIG. 12B). Production of these factors by PTG CD34$^+$ cells were insensitive to oxygen tension in the media and much higher than that by SCIPC and eBCs. These peptides have been associated with neo-vasculogenesis and therefore, without being bound to theory, may be important for cell survival after transplant.

Example 14

Mouse and Human PTG-Derived CD34$^+$ Cells Secrete Chemokines for Stem Cells and Endothelial Cells Including CCL-2 and CXCL-12

Figure 13A:
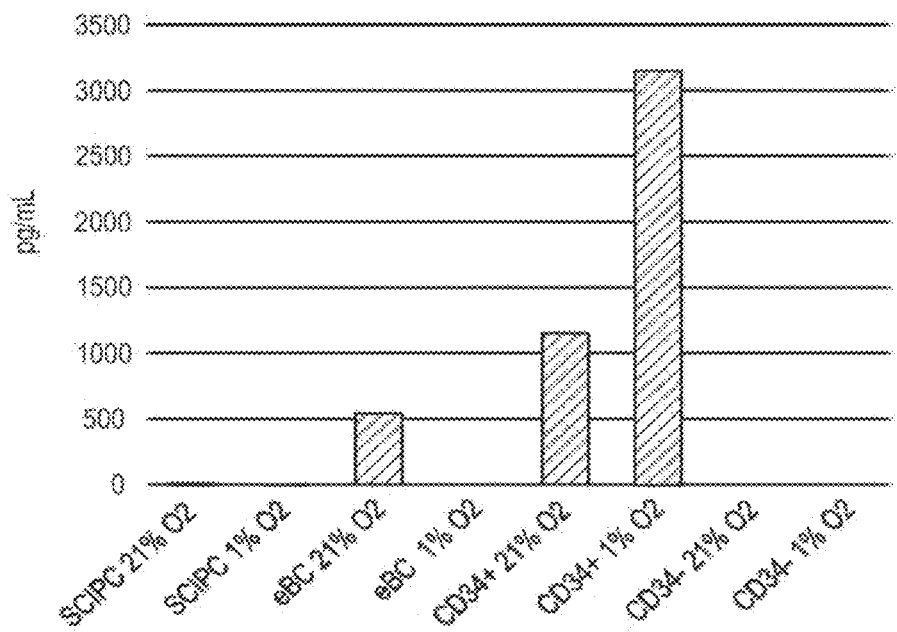
FIG. 13A depicts the release of CCL-2 by SCIPC, eBC, CD34+, and CD34− cells.
Figure 13B:
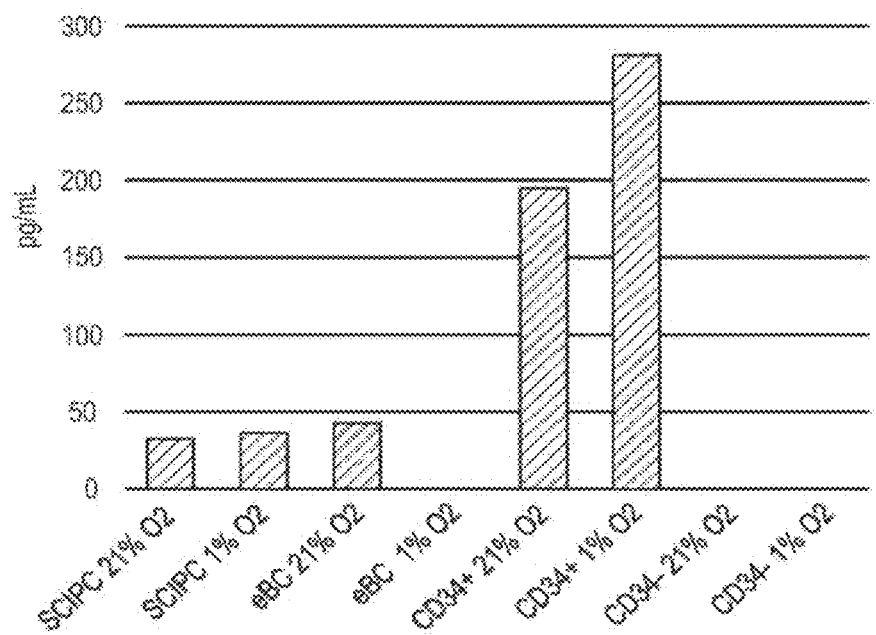
FIG. 13B depicts the release of CXCL-12 by SCIPC, eBC, CD34+, and CD34− cells. SCIPC, eBC, CD34+, and CD34− cells were cultured for 24 hours in 21% oxygen or 1% oxygen. At the end of the experiments, supernatant was collected and analyzed for human cytokines.
Figure 13C:
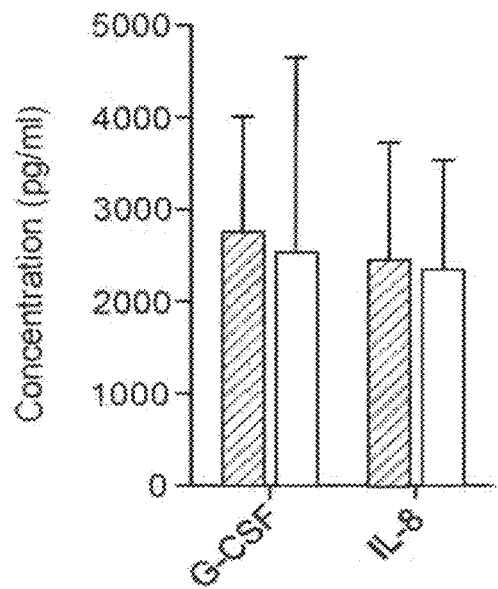
FIGS. 13C-13D depicts angiogenic factors secreted by human parathyroid gland fragments in ex vivo cultures. Freshly procured PTG were cut into small pieces and cultured overnight at atmospheric oxygen concentration of 21% or in a hypoxic chamber at 1% oxygen concentration. The culture supernatant was collected and presence of angiogenic factors were measured using a 17-member angiogenesis Luminex panel. Data presented are a summary of results from three unrelated donors.
Figure 13D:
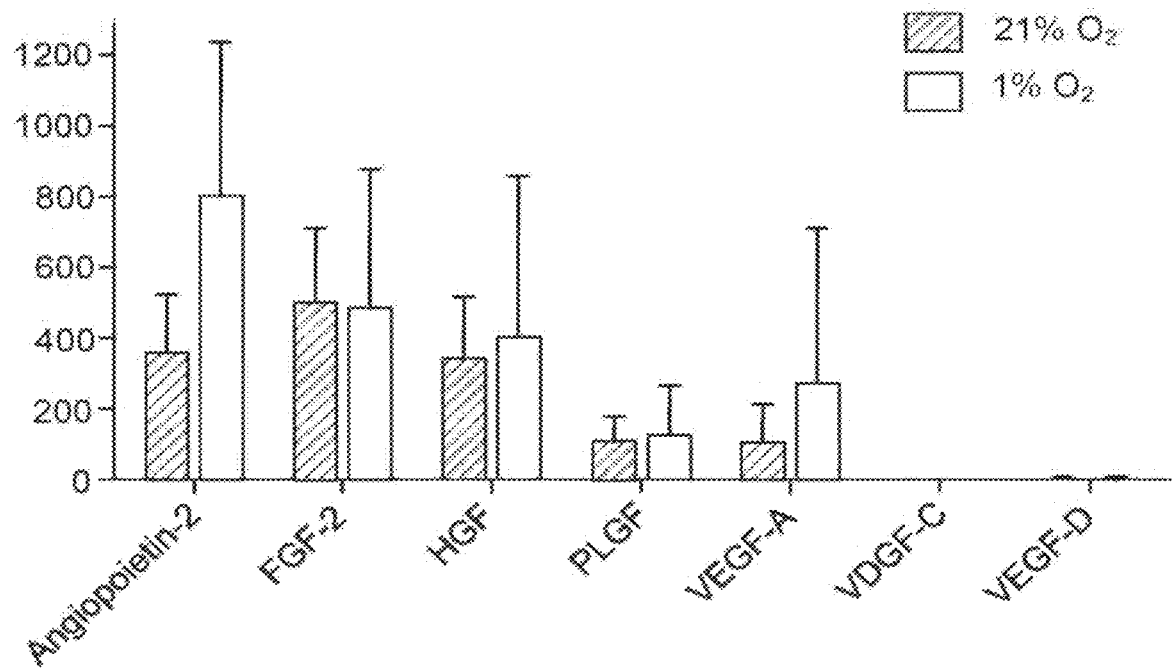

This example shows that CD34$^+$ cells produce chemokines associated with stem cell recruitment. The same in vitro cultures described in Examples 12 and 13 above also exhibited high secretion of CCL2 and CXCL12 among the peptides produced by SCIPC, eBC, and CD34$^+$ cells but not CD34− cells (FIG. 13A and FIG. 13B). When stressed with hypoxia SCIPC and eBC stop producing chemoattractant molecules, however CD34$^+$ cells, but not CD34−, increase secretion of said molecules. These peptides have been associated with chemoattractant activity, and may be important for recruiting and retaining angiogenic cells to the graft after transplant. Numerous angiogenic factors are also secreted by unfractionated human PTG fragments cultured ex vivo overnight. Most islet graft angiogenesis research focus on VEGFs. While PTG secreted VEGF-A, it also produced a wide array of other angiogenic factors including angiopoietin-2, FGF-2, HGF, PLGF, G.CSF and IL8 (FIG. 13C).

Example 15

Factors Expressed by PTG Following Co-Transplantation

Figure 15A:
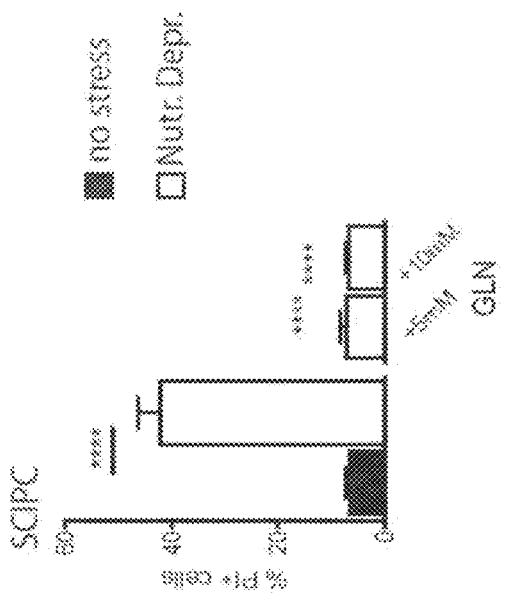
FIG. 15A, FIG. 15B, and FIG. 15C depict the effect of nutrient supplementation on islet cell death in vitro. The effects of cell survival by supplementation of amino acids on mouse islets (FIG. 15A), human islets (FIG. 15B), and SCIPC (FIG. 15C) cultured in low or high density conditions (mouse=1000 islets/mL, human=1000 islets/mL, SCIPC=3000 clusters/mL) in RPMI +5% serum with addition of glucose. GLN: glutamine, TRP: tryptophan. Cell viability is quantified using PI staining via flow cytometry. Data shown are a summary of 3 independent experiments.
Figure 15B:
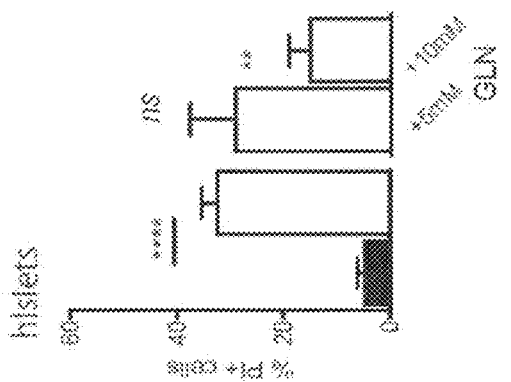
Figure 15C:
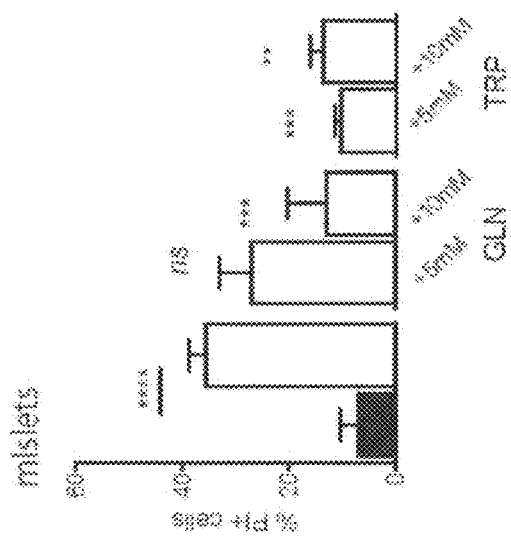

This Example provides microarray data showing gene expression in cells derived from PTG. Four batches (1-4) of mouse parathyroid glands (PTGs) were dissected free of thyroid and the surrounding fibrous tissues and used for RNA extraction with a RNA-Stat 60 kit (Thermo Fisher Scientific, Inc.) as described previously (Chang et al., *Sci Signal.* 2008 Sep. 2; 1(35) and Cheng et al., 2013 *JBMR* 28:1087-1100). The RNA was reversed transcribed into cDNA, which was then subjected to Affymetrix GeneChip Microarray analyses by the Genomic Technologies Core Facility (Faculty of Biology, Medicine and Health, University of Manchester). The gene array data were analyzed using Affymetrix Genechip Operating Software by Dr. Leo Zeef at the Bioinformatics Core Facility, University of Manchester for an intensity value and a Present/Margin/Absent (PMA) value to indicate the likelihood of expression for each given gene in the parathyroid glands. All genes included in Table 1 have a PMA p value<0.05 that indicates significant likelihood of gene expression. The gene expression levels (intensity values) were then normalized and presented as % of the expression level of a mitochondrial microsomal protein L19 (L19) and used for statistical analyses by Microsoft Excel software as shown. The Affymetrix GeneChip Microarray analyses were performed on the same RNA twice and the values were averaged. N=4 batches of RNA with each batch extracted from 20 PTGs dissected from 10 of 6-week-old C57bB6 mice.

mL, SCIPC=3000 clusters/mL) in RPMI +5% serum with addition of glucose. These amino acids preserved viability of isolated mouse islets (FIG. 15A), isolated human islets (FIG. 15B) and SCIPC (FIG. 15C) under nutrient-limiting condition.

Example 17

Human PTG and its Secreted Factors Protection of Survival and Function of Mature Human Islets In Vitro Under Nutrient Deprivation and Hypoxic Conditions In this Example, the ability of one or more factors identified in Example 16 or any other previous Example as being produced by PTG to protect human islets differentiation and viability under nutrient deprived and hypoxic conditions is examined. These PTG secreted factors (such as, but not limited to, PTH, PTHrP and GABA) are added to cultures of isolated human islets.

TABLE 1

Results of array analysis

| Gene Title | Gene Name | 1 | 2 | 3 | 4 | PMA p value |
|---|---|---|---|---|---|---|
| parathyroid hormone | Pth | 46685.8 | 48889.8 | 86768.4 | 70088.7 | 0.002 |
| platelet derived growth factor, alpha | Pdgfa | 929.9 | 602.3 | 829.1 | 873.4 | 0.002 |
| platelet derived growth factor, B polypeptide | Pdgfb | 106.6 | 219.8 | 133.6 | 176.8 | 0.038 |
| platelet-derived growth factor, C polypeptide | Pdgfc | 2135.5 | 765.7 | 983.6 | 700.9 | 0.002 |
| platelet-derived growth factor, D polypeptide | Pdgfd | 290.7 | 86.6 | 71.5 | 99.3 | 0.002 |
| angiopoietin 1 | Angpt1 | 238.9 | 230.1 | 292.9 | 265.9 | 0.004 |
| angiopoietin 4 | Angpt4 | 109.0 | 75.0 | 55.5 | 19.7 | 0.003 |
| vascular endothelial growth factor A | Vegfa | 1507.2 | 2668.5 | 2053.2 | 2310.6 | 0.002 |
| vascular endothelial growth factor C | Vegfc | 1065.5 | 1100.6 | 1017.9 | 1103.0 | 0.002 |
| chromogranin A | Chga | 49287.6 | 50327.4 | 85181.4 | 71315.2 | 0.002 |
| glutamate decarboxylase 1 | Gad1 | 13.0 | 54.0 | 60.4 | 125.3 | 0.004 |
| glutamic acid decarboxylase 2 | Gad2 | 42.7 | 80.7 | 32.9 | 107.2 | 0.025 |
| tryptophan hydroxylase 1 | Tph1 | 57.5 | 56.0 | 74.5 | 42.7 | 0.006 |
| dopa decarboxylase | Ddc | 222.6 | 268.6 | 74.8 | 111.2 | 0.002 |
| 5-hydroxytryptamine (serotonin) receptor 2C | Htr2c | 46.7 | 60.8 | 19.7 | 38.4 | 0.006 |
| leptin receptor | Lepr | 202.9 | 108.5 | 77.5 | 128.4 | 0.005 |
| CD34 antigen | Cd34 | 8984.5 | 6233.8 | 5257.1 | 6541.3 | 0.002 |
| tryptophan hydroxylase 1 | Tph1 | 57.5 | 56.0 | 74.5 | 42.7 | 0.006 |

Example 16

Tryptophan and Glutamine Help Islet and SCIPC Survival Under Nutrient Deprivation In Vitro This Example shows that tryptophan (a precursor to serotonin via the tryptophan hydroxylase and dopa decarboxylase pathway) and glutamine (a precursor to GABA via glutamate decarboxylase pathway) help SCIPC survival in vitro. Various insulin-producing cells cultured in low (nutrient replete; mouse=200 islets/mL, human=200 islets/mL, SCIPC=200 clusters/mL) or high density conditions (nutrient limiting; mouse=1000 islets/mL, human=1000 islets/

Example 18

PTG Protection of Survival and Function of Juvenile and Adult Porcine Islets In Vivo after Transplant Since preliminary experiments have highlighted a consistent phenomenon across mouse and human species, it is anticipated that porcine islets will also benefit from PTG co-transplantation. The advent of gene editing technology has greatly accelerated the pace of engineering porcine donors to reduce their immunogenicity and risk of transmitting zoonotic diseases. It has becoming increasingly plau-

Example 19

Human PTG Induction of Protective Immunomodulatory Effect Via PTH, GABA Paracrine Effects Human PTG can survive and function after transplantation in HLA-mismatched allogeneic recipients without the need of immunosuppression, suggesting that the tissue not only has the unique ability to survive ischemic injury, but also can effectively modulate alloimmune responses. Literature shows that PTH and GABA have inhibitory effects on T cell immune responses. It has been observed that mouse PTG can persist for 6 weeks after transplantation in fully mismatched recipients without immunosuppression. Whether PTG can provide alloimmune protection for co-transplanted islets has not been reported. A PTG or CD34+ co-transplant is examined and modulation of the immune response with protective effects for the islet grafts is determined. If PTG provides immune protection, the active fraction (CD34+ or CD34−) and factors (e.g., PTH, GABA, CXCL12) is investigated.

Example 20

Human PTG-Derived Serotonin and Leptin Effects on Survival and Differentiation of SCIPC and eBC Grafts In Vitro Under Nutrient Deprivation and Hypoxic Conditions Recent literature has demonstrated the PTG's crucial role in regulating metabolism and to this effect, it was recently elucidated that the PTG effects paracrine levels of leptin and serotonin. Both of these factors are critical endocrine signaling molecules for normal islet physiology that have been shown in multiple mouse and human models to prevent apoptosis and improve insulin secretion. Using an in vitro PI and GFP model, the ability of serotonin and leptin to improve viability and maintain beta cell differentiation under hypoxic and nutrient deprived conditions is examined.

Example 21

PTG Derived CD34+ Cells and their Benefit to Viability and Function Compared to Adult Hematopoietic, Umbilical Cord Blood, Human Embryonic Stem Cell, and Placenta-Derived CD34+ Cells Without being bound to theory, it is hypothesized that the PTG derived CD34+ population will be potent in protecting islets during transplantation due to the additive effect of 1) endothelial cell lineage CD34+ cells and 2) the unique factors secreted by the PTG CD34+ cells that support the islet graft (such as, without limitation, GABA, PTH, PTHrP, etc.). Other CD34+ rich populations are tested using a co-transplantation luciferase model with eBC's in order to define the cells and or factors needed to support the islet graft fully.

As disclosed herein, CD34+ cells derived from other sources are also able to support the islet graft as efficaciously as PTG derived CD34+ cells. In particular, experimental data described at Examples 26 and 27 has demonstrated the ability to differentiate CD34+ CD45− cells from the same human embryonic stem cell (hESC) line as used for SCIPC and eBC differentiation and from an induced pluripotent stem cell (iPSC) line. The factors hESC and iPSC CD34+ CD45− cells secrete and cell surface markers these cells expressed are identified in order to further hone or refine the exact CD34+ fraction needed to support the islet graft. Re-aggregating SCIPC or eBC with CD34+ cells in culture prior to transplantation is demonstrated to more closely re-approximate mature human islet morphology and provide improved engraftment and viability during stem cell islet transplantation compared to eBC or SCIPC alone.

Example 22

Differentiation of Stem Cell Derived CD34+ Cells (scCD34+)

Figure 17A:
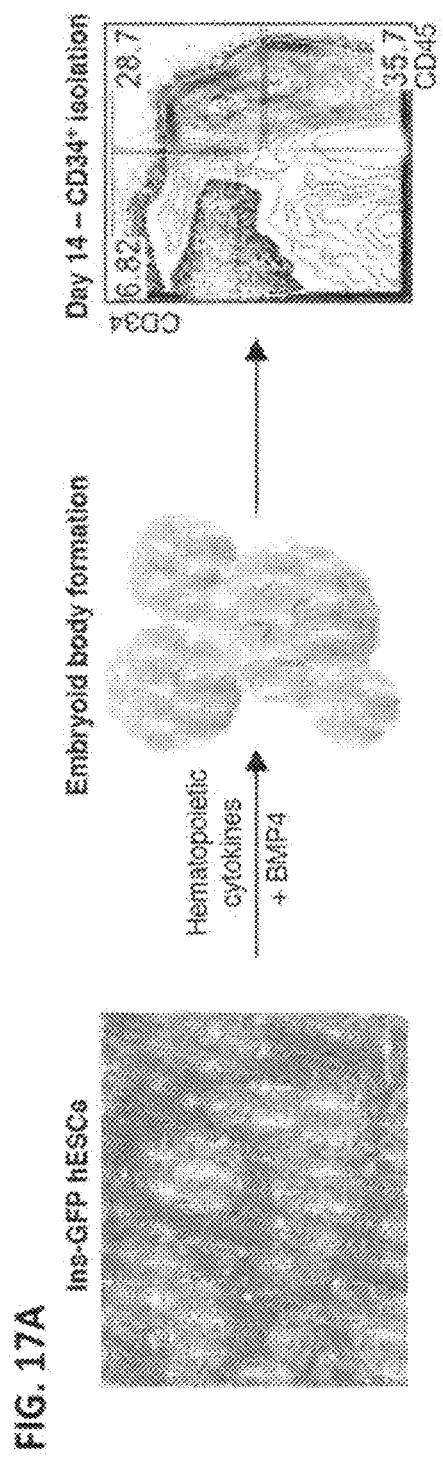
FIGS. 17A-17B pictorially illustrate a non-limiting example of the differentiation of CD34$^+$ cells from human pluripotent stem cells (hPSCs).
Figure 17B:
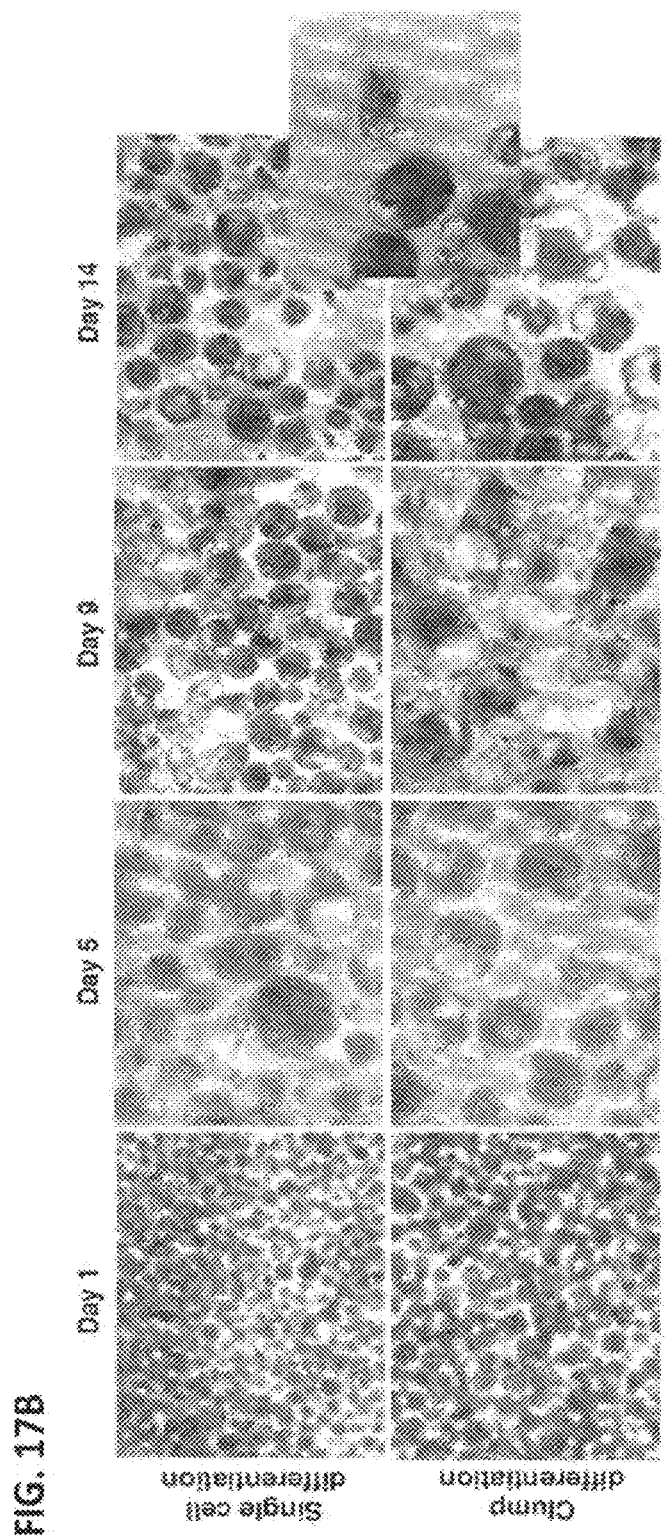

This Example describes a non-limiting example of the differentiation of CD34+ cells from human pluripotent stem cells (hPSCs) in accordance with some embodiments of the disclosure. Human pluripotent stem cells (hPSCs) were maintained on mouse embryonic fibroblast (GlobalStem) feeders in DMEM/F12+20% KnockOut-Serum Replacement (Invitrogen), 1 mM L-glutamine, 1 mM NEAA, 0.1 mM β-mercaptoethanol, and 10 ng/mL bFGF. Media was changed daily, and cells were passaged 1:4 onto fresh feeders every 5-7 days using standard clump passaging with collagenase IV or by single cell trypsinization using TrypLE (Gibco). For CD34+ differentiation, hPSC colonies were scraped into nonadherent rotating 10 cm or 6 well plates and allowed to form 3-dimensional structures called embryoid bodies (EB). The CD34+ EB differentiation media was KO-DMEM (Gibco), 20% FBS (Gemini BioSciences), 1 mM L-glutamine, 1 mM NEAA, penicillin/streptomycin, 0.1 mM β-mercaptoethanol, 200 μg/mL h-transferrin, and 50 μg/mL ascorbic acid. After 24 hrs, media was changed by allowing EBs to settle by gravity and replaced with EB media supplemented with growth factors: 50 ng/mL BMP4, 200 ng/mL SCF, 200 ng/mL FLT3, 50 ng/mL G-CSF, 20 ng/mL IL-6, 10 ng/mL IL-3 (all Peprotech). Media was changed on day 1, day 5, and day 10. EBs were dissociated on Day 14 by digesting with collagenase B (Roche) for 2 hrs, followed by treatment with enzyme-free dissociation buffer (Gibco), and filtered through a 70 μm filter. Dissociated EBs were frozen in 10% DMSO, 40% FBS freezing solution. As illustrated in FIG. 17A, pluripotent stem cells (e.g., Ins-GFP hESCs) were differentiated into CD34+ cells using a 14 day embryoid body-based differentiation protocol in the presence of SCF, FLT3-Ligand, IL3, IL6, TPO and BMP4. FIG. 17B illustrates the morphological progression of the pluripotent stem cells during differentiation, where the stem cells were differentiated as single cells or as clump.

Figure 18:
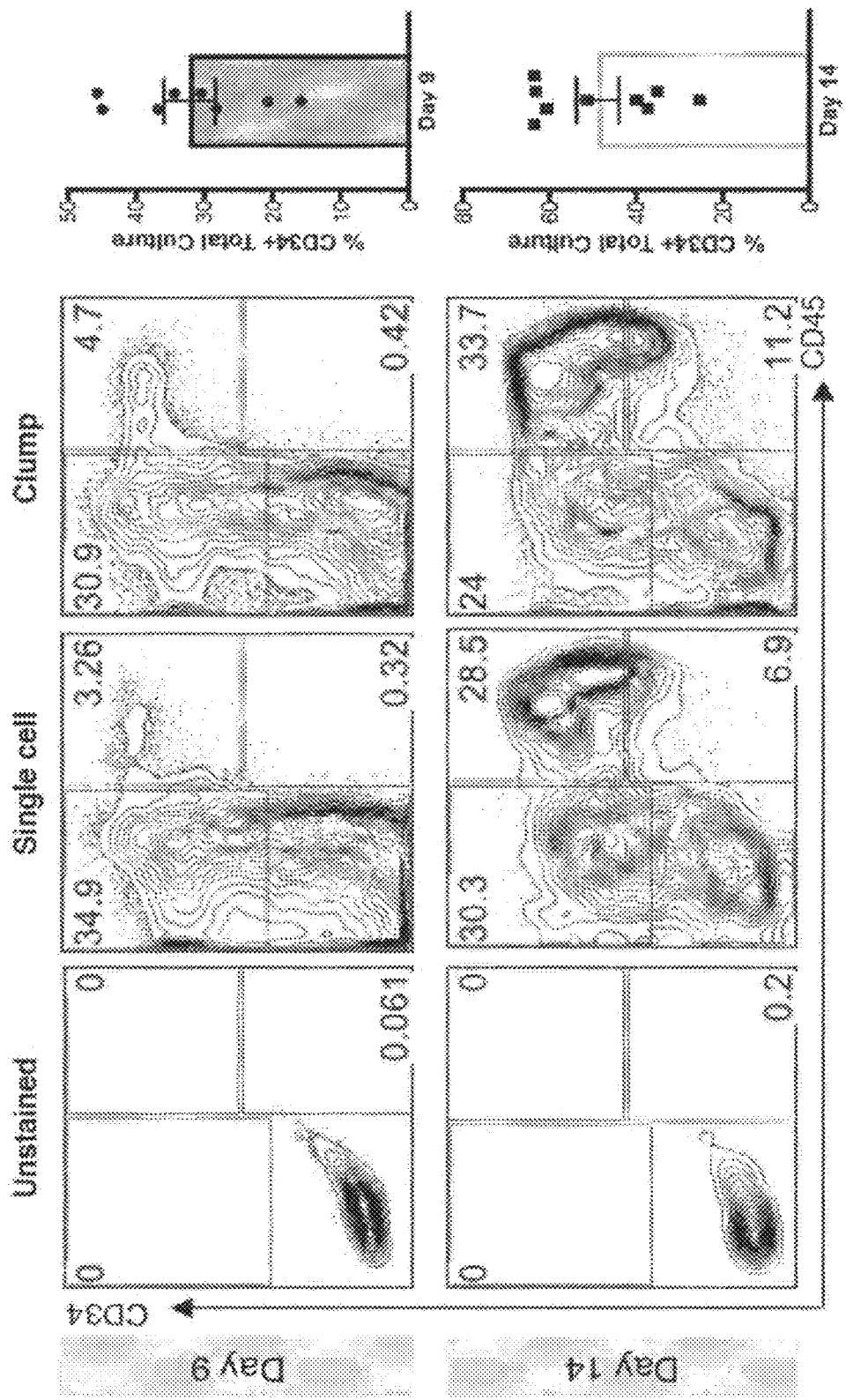
FIG. 18 graphically illustrates a robust differentiation of CD34$^+$ cells from human pluripotent stem cells (hPSCs) in accordance with some embodiments of the disclosure. In these experiments, CD34$^+$ cells from embryoid body differentiation from FIGS. 17A-17B were analyzed on Day 9 and Day 14 of differentiation.

As shown in FIG. 18, a robust differentiation of CD34+ cells from human pluripotent stem cells (hPSCs) was observed. In these experiments, CD34+ cells from embryoid body differentiation from Example 22 were analyzed on Day 9 and Day 14 of differentiation.

Example 23

Differentiation of scCD34+ Cells

Figure 19A:
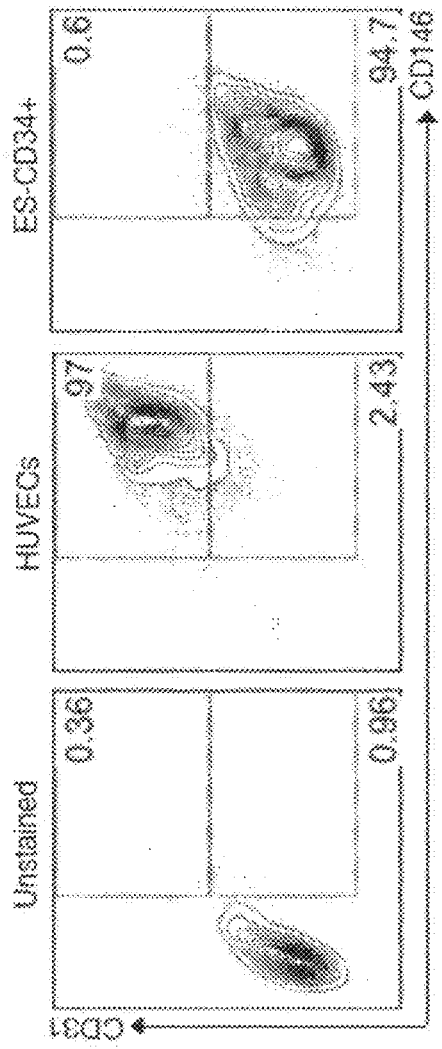
FIGS. 19A-19B summarize the results from in vitro experiments performed to characterize CD34+ cells which were derived from human pluripotent stem cells (hPSCs) in accordance with some embodiments of the disclosure. Flow cytometric analysis of vascular progenitor markers of parathyroid gland-derived CD34$^+$ cells, human umbilical vein endothelial cells (HUVECs), and scCD34$^+$ cells on DAY 7 and Day 10 after plating.
Figure 19B:
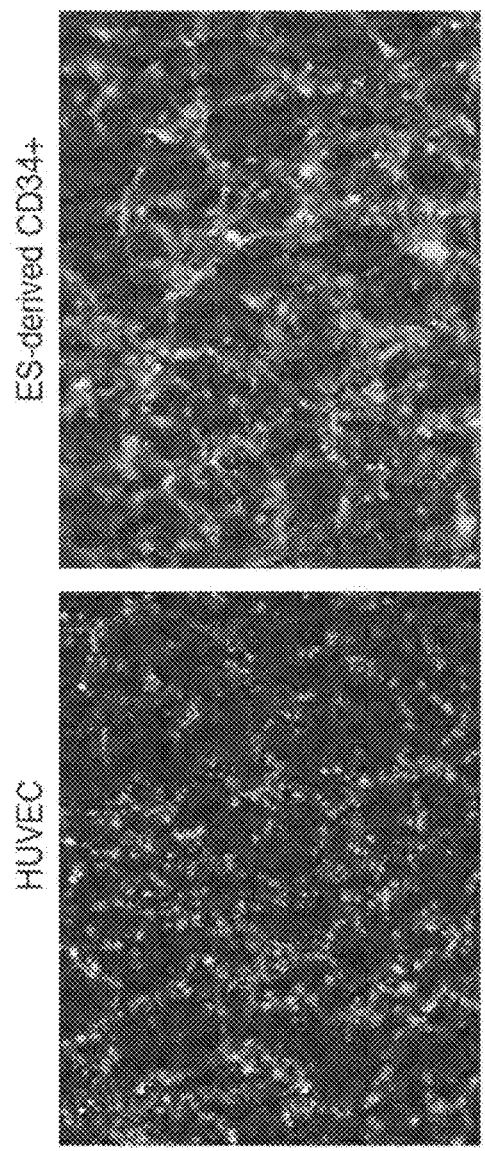
Figure 20B:
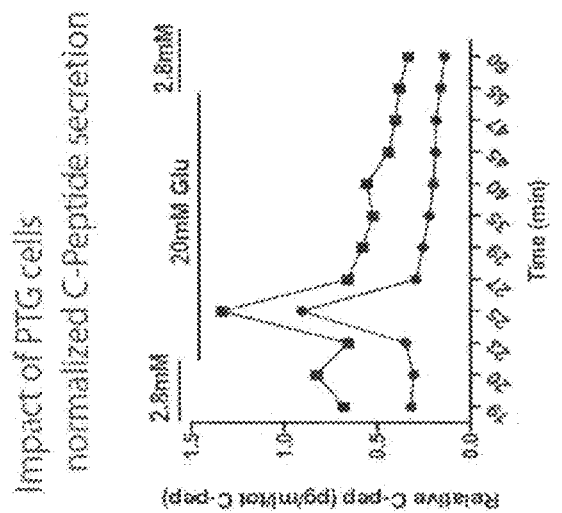
Figure 20C:
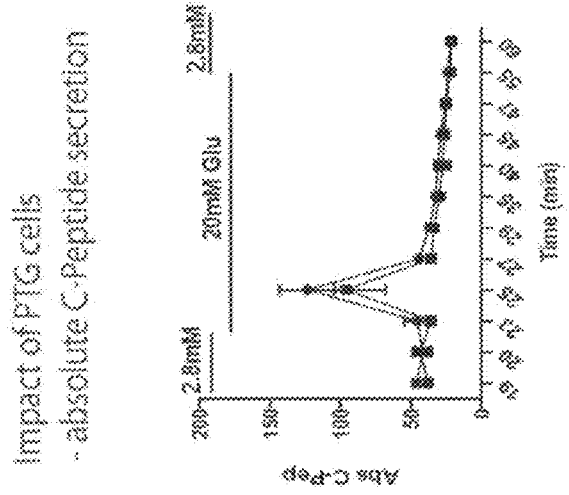
Figure 20D:
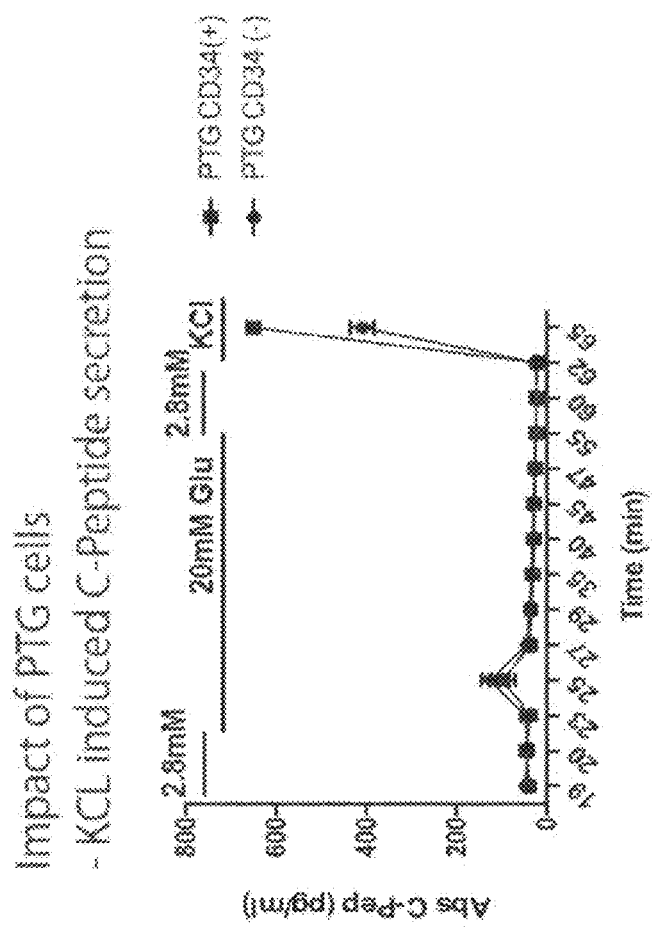

This Example describes the results from in vitro experiments performed to characterize CD34+ cells derived from human pluripotent stem cells (hPSCs) in accordance with some embodiments of the disclosure. In these experiments, flow cytometric analysis of vascular progenitor markers of parathyroid gland-derived CD34$^+$ cells, human umbilical vein endothelial cells (HUVECs), and scCD34$^+$ cells on DAY 7 and Day 10 after plating. As shown in FIG. 19A, bright-field images of HUVECs and scCD34$^+$ demonstrate that scCD34$^+$ cells have adherent morphology. As shown in FIG. 19B, in vitro angiogenesis assay reveal that HUVECs and scCD34+ cells form tube-like networks after 4 hours in culture. It was observed that scCD34$^+$ cells were adherent and expressed the immunophenotypic markers CD34$^+$, CD146$^+$, and CD31$^-$ after 7-10 days of in vitro culture, similarly to human parathyroid gland-derived CD34$^+$ cell, which also expressed the immunophenotypic markers CD34$^+$, CD146$^+$. Furthermore, in an in vitro angiogenesis assay, scCD34$^+$ cells form tube-like network in 4 hours, similar to human umbilical vein endothelial cells (HUVECs), demonstrating robust in vitro angiogenic potential.

Example 24

Formation of Vascular Beta Clusters (vBCs)

This Example describes the results from glucose-stimulated insulin secretion test (GSIS) on vascular beta clusters (vBCs) prepared in accordance with some embodiments of the disclosure. Human pluripotent stem cells (hPSCs) were maintained and propagated on mouse embryonic fibroblasts (MEFs) in hPSC media (DMEM F-12 supplemented with 1× Glutamax, 1× MEME-NEAA, 1× Beta-mercaptoethanol, KSR and FGF-2). Subsequently, confluent hPSC cultures were dissociated into single-cell suspension and seeded in suspension plates in hPSC media supplemented with Activin A (10 ng/ml, R&D Systems) and HeregulinB (10 ng/ml, Peprotech). The plates were incubated on an orbital shaker to induce 3D sphere formation. Spheres formed in this manner were subsequently cultured for 20 days using the following media:

Day 1: RPMI (Gibco) containing 0.2% FBS, 1:5,000 ITS (Gibco), 100 ng/ml activin A, 50 ng/ml WNT3a (R&D Systems).

Day 2: RPMI containing 0.2% FBS, 1:2,000 ITS, 100 ng/ml activin A.

Day 3: RPMI containing 0.2% FBS, 1:1,000 ITS, 2.5 µm TGFbi IV (CalBioChem), 25 ng/ml KGF (R&D Systems).

Day 4-5: RPMI containing 0.4% FBS, 1:1,000 ITS, 25 ng/ml KGF.

Day 6-7: DMEM (Gibco) with 25 mM glucose containing 1:100 B27 (Gibco), 3 nM TTNBP (Sigma).

Day 8: DMEM with 25 mM glucose containing 1:100 B27, 3 nM TTNBP, 50 ng/ml EGF (R&D Systems).

Day 9-11: DMEM with 25 mM glucose containing 1:100 B27, 50 ng/ml EGF, 50 ng/ml KGF.

Day 12-20: DMEM with 25 mM glucose containing 1:100 B27, 1:100 Glutamax (Gibco), 1:100 NEAA (Gibco), 10 µm ALKi II (Axxora), 500 nM LDN-193189 (Stemgent), 1 µm Xxi (Millipore), 1 µm T3 (Sigma-Aldrich), 0.5 mM Vitamin C, 1 mM N-acetyl Cysteine (Sigma-Aldrich), 10 µm zinc sulfate (Sigma-Aldrich) and 10 µg/ml of Heparin sulfate.

After 20 days of differentiation, spheres were dissociated in single cell suspension using Accumax and sorted by flow cytometry to select for insulin producing hPSC-derived beta cells. Sorted hPSC-derived beta cells were mixed with PTG-derived CD34+ cells or hPSC-derived CD34+ cells at different ratios, and re-aggregated in Aggrewell plates (StemCell Technologies) at 1000 cells/cluster in CMRL containing 1:100 B27, 1:100 Glutamax (Gibco), 1:100 NEAA (Gibco), 10 µm ALKi II (Axxora), 0.5 mM Vitamin C, 1 µm T3 (Sigma-Aldrich), 1 mM N-acetyl Cysteine (Sigma-Aldrich), 10 µm zinc sulfate (Sigma-Aldrich), 10 µg/ml of Heparin sulfate.

After 72 hours the re-aggregated vascular Beta clusters (vBCs) were transferred into suspension plates and used for transplantation or in vitro studies within 1-3 days.

Example 25

Formation of Vascular Beta Clusters (vBCs)

This Example describes the results from glucose-stimulated insulin secretion test (GSIS) on vascular beta clusters (vBCs) prepared in accordance with some embodiments of the disclosure. As shown in FIGS. 20A-20D, it was observed that vBCs dynamically responded to alternating low and high glucose as shown by glucose stimulated insulin secretion test (GSIS) in a perifusion system. In particular, a rapid first-phase response was observed similar to human islets, and a modest second-phase response is also observed in vBCs co-clustered with CD34$^+$ but not with CD34$^-$ cells.

Example 26

Improved Survival of Stem Cell-Derived Insulin-Producing Cell (SCIPC) In Vitro

This Example demonstrates that CD34$^+$ and CD34$^-$ cell derived from parathyroid gland are able to improve survival of stem cell-derived insulin-producing cell (SCIPC).

Figure 21:
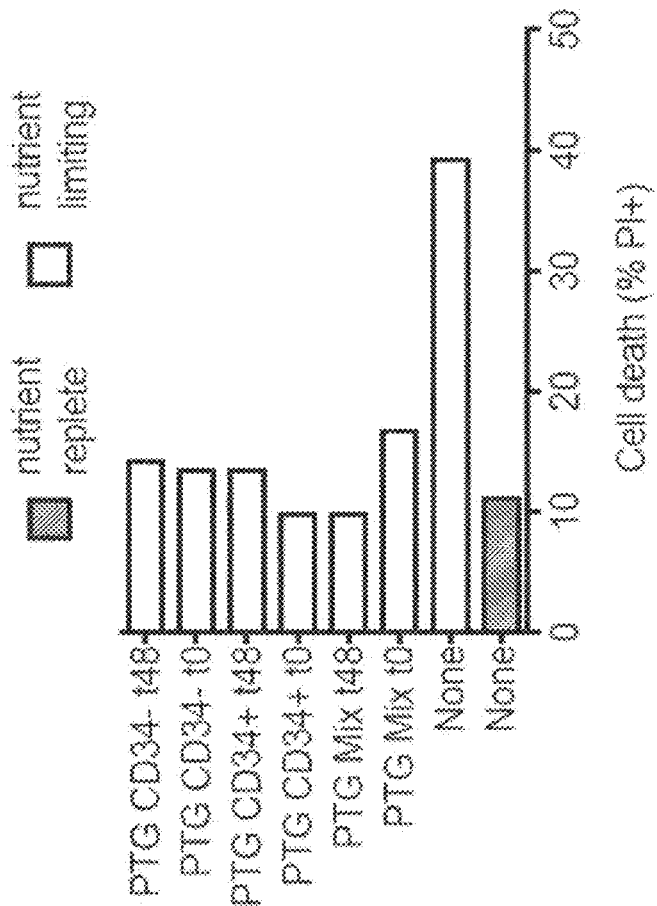
FIG. 21 graphically summarizes experimental data demonstrating that CD34$^+$ cells derived from PTG were utilized soon after being procured or 48 hours later. Following incubation in nutrient-deprived media for 24 hours, the medium was collected and centrifuged at 1500 rpm for 5 min. SCPIC were cultured with or without nutrient-deprived conditioned media at 37° C. for 24 hours. Control group showed about 40% cell death after 24 hours, however, CD34$^-$ and CD34$^+$-conditioned group improved SCIPC survival in nutrient-deprived media.

Experimental data shown in FIG. 21 indicates that PTG-derived CD34$^+$ and CD34$^-$ cells were utilized soon after being procured or 48 hours later. In this experiment, following incubation in nutrient-deprived media for 24 hours, the medium was collected and centrifuged at 1500 rpm for 5 min. SCPIC were cultured with or without nutrient-deprived conditioned media at 37° C. for 24 hours. As illustrated in FIG. 21, control group showed about 40% cell death after 24 hours, however, CD34− and CD34+-conditioned group improved SCIPC survival in nutrient-deprived media.

Figure 22:
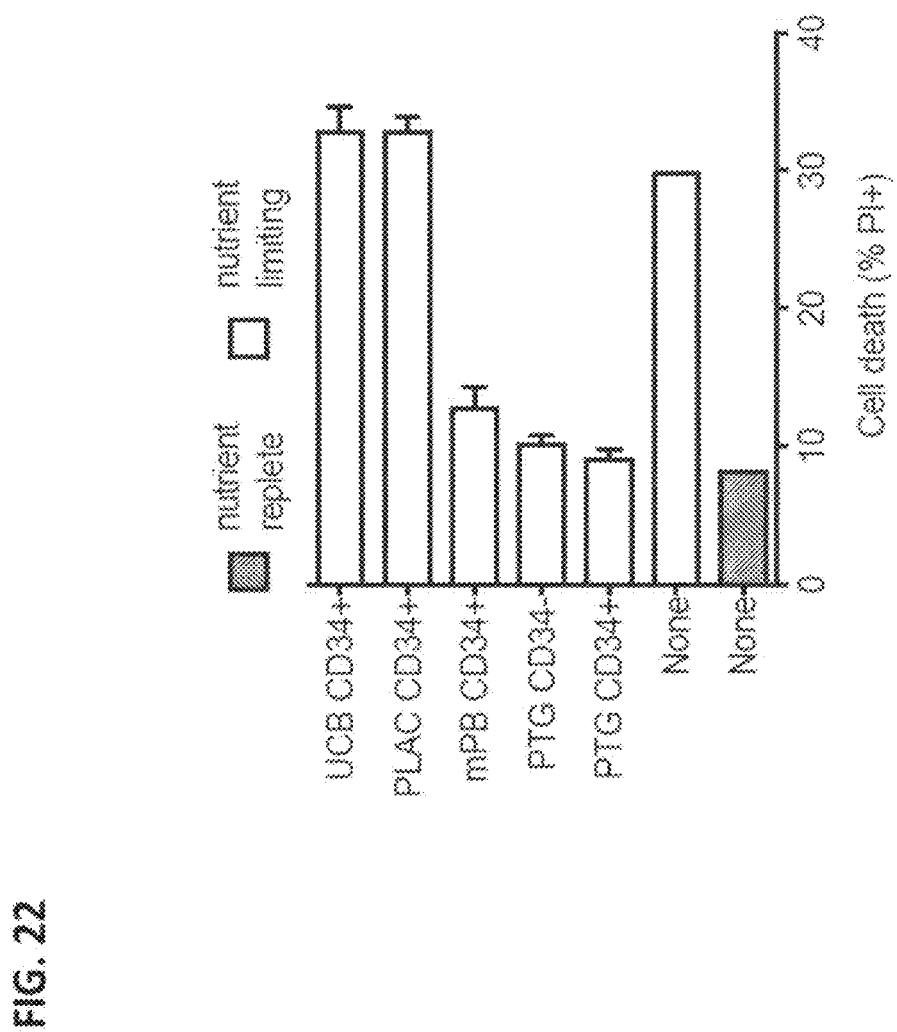
FIG. 22 graphically summarizes experimental data demonstrating that PTG-derived CD34$^-$ and CD34$^+$ cells significantly improve survival of stem cell-derived insulin-producing cell (SCIPC) in nutrient-deprived media.

In another experiment, PTG-derived CD34+ and CD34−, mPB, Placenta, and umbilical cord blood (UCB) cells were cultured in nutrient-deprived media. Following incubation for 24 hours, the conditioned medium was collected and centrifuged at 1500 rpm for 5 min, then SCPIC were cultured in the conditioned media for 24 hours in nutrient-deprived media at 37° C. As shown in FIG. 22, control group showed about 30% cell death after 24 hours, however, CD34$^-$ and CD34$^+$-conditioned group significantly improved SCIPC survival in nutrient-deprived media.

Figure 23:
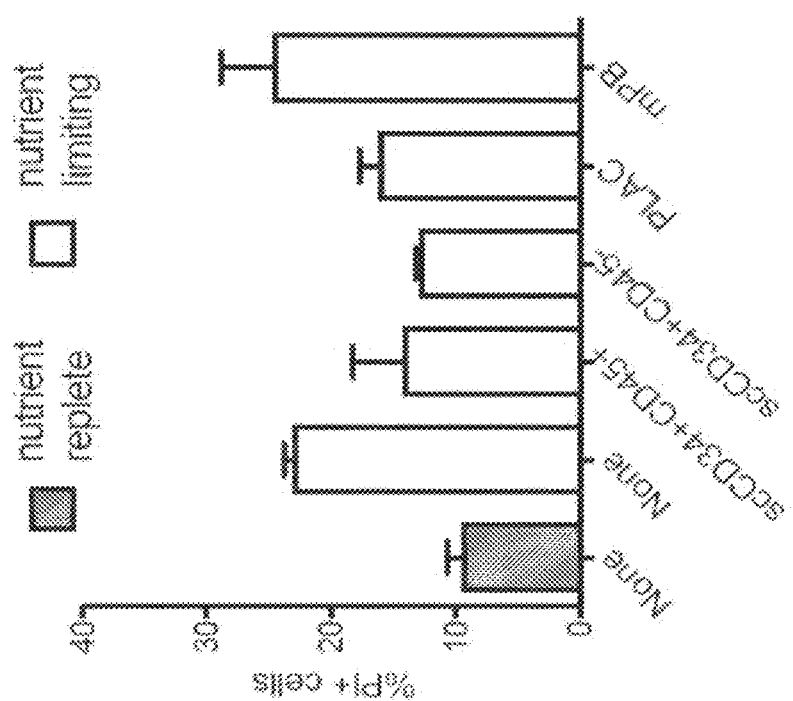
FIG. 23 graphically summarizes experimental data demonstrating that stem cell-derived CD34$^-$ and CD34$^+$ cells are also able to improve survival of stem cell-derived insulin-producing cell (SCIPC) in nutrient-deprived media.

In a similar fashion, experiments shown in FIG. 23 indicate that CD34$^+$ and CD34$^-$ cells derived from embryonic stem cells were also able to improve survival of stem cell-derived insulin-producing cell (SCIPC). In these experiments, ES-derived CD34$^+$CD45$^+$ cells, ES-derived CD34$^+$CD45$^-$ cells, mobilized peripheral blood (mPB), and placenta cells were cultured in nutrient-deprived media. Following incubation for 24 hours, the conditioned medium was collected and centrifuged at 1500 rpm for 5 min, then SCPIC were cultured in the conditioned media for 24 hours in nutrient-deprived conditioned media at 37° C. Control group showed about 25% cell death after 24 hours, however, CD34$^-$ and CD34$^+$-conditioned group significantly improved SCIPC survival in nutrient-deprived media.

Example 27

Characterization of Cytokines Released by ES-Derived CD34+ Cells

This Example demonstrates that ES-derived CD34+ CD45+ cells release proangiogenic factors such as vascular endothelial growth factor (VEGF), platelet-derived growth factor (PDGF), and epidermal growth factor (EGF).

Stem cell-derived CD34+ CD45−, CD34−CD45−, mobilized peripheral blood (mPB), and term placenta cells were maintained in culture for 24 hours. Human cytokines released in the supernatant were determined by using Luminex technology. A total of 65 cytokines and chemokines were analyzed. As shown in FIGS. 24A-24C, vascular endothelial growth factor-A (VEGF-A) secretion was comparable in all samples analyzed: ES-derived CD34+CD45+, ES-derived CD34+CD45−, mPB, and Placenta. However, ES-derived CD34+CD45− showed significantly higher secretion of PDGF-AA and EGF molecules.

Example 28

Co-Clustering of Enhanced Beta Cluster (eBC) with PTG-derived CD34+ Cells Provides Graft Protection in Subcutaneous Route This Example describes the results of in vivo mouse experiments performed to demonstrate that co-clustering of enhanced beta cluster (eBC) with PTG-derived CD34+ cells provides graft protection in subcutaneous (SQ) administration.

Figure 25A:
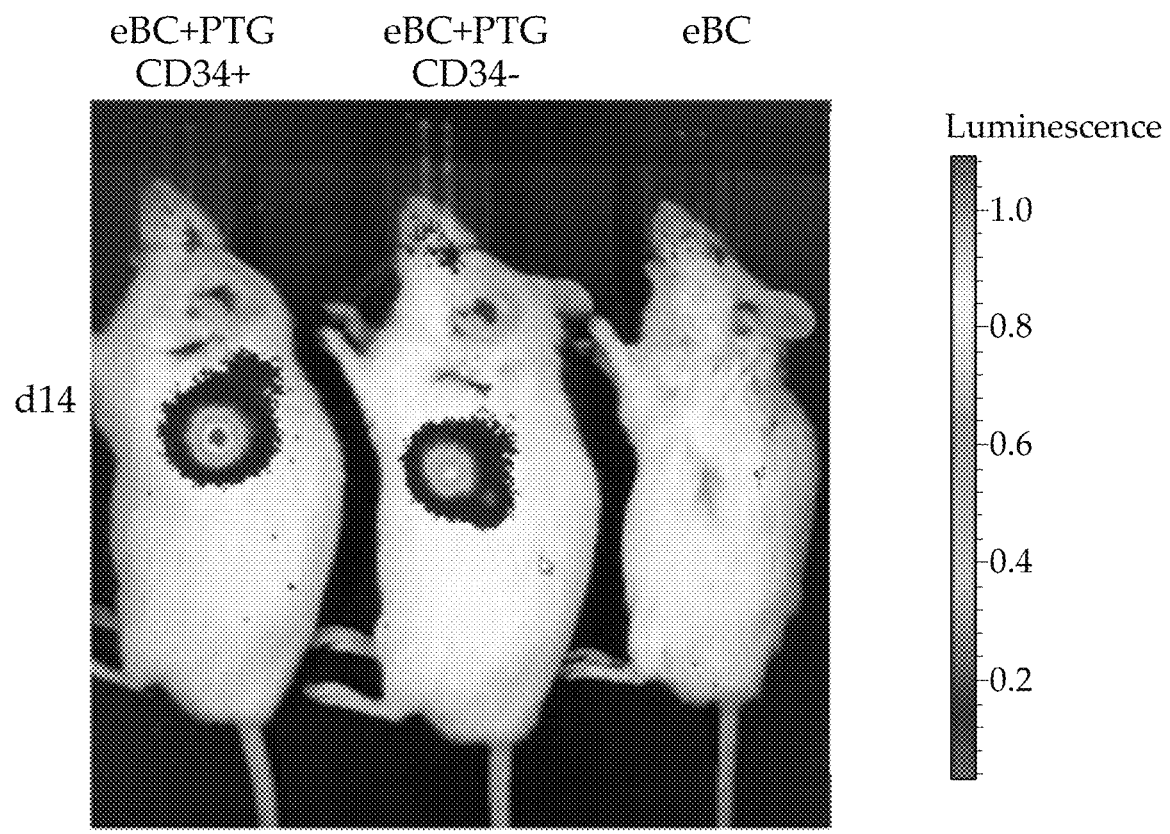
FIGS. 25A-25B summarize experimental results demonstrating that co-clustering of eBC with PTG-derived CD34$^+$ provides immediate and lasting graft protection in subcutaneous administration.
Figure 25B:
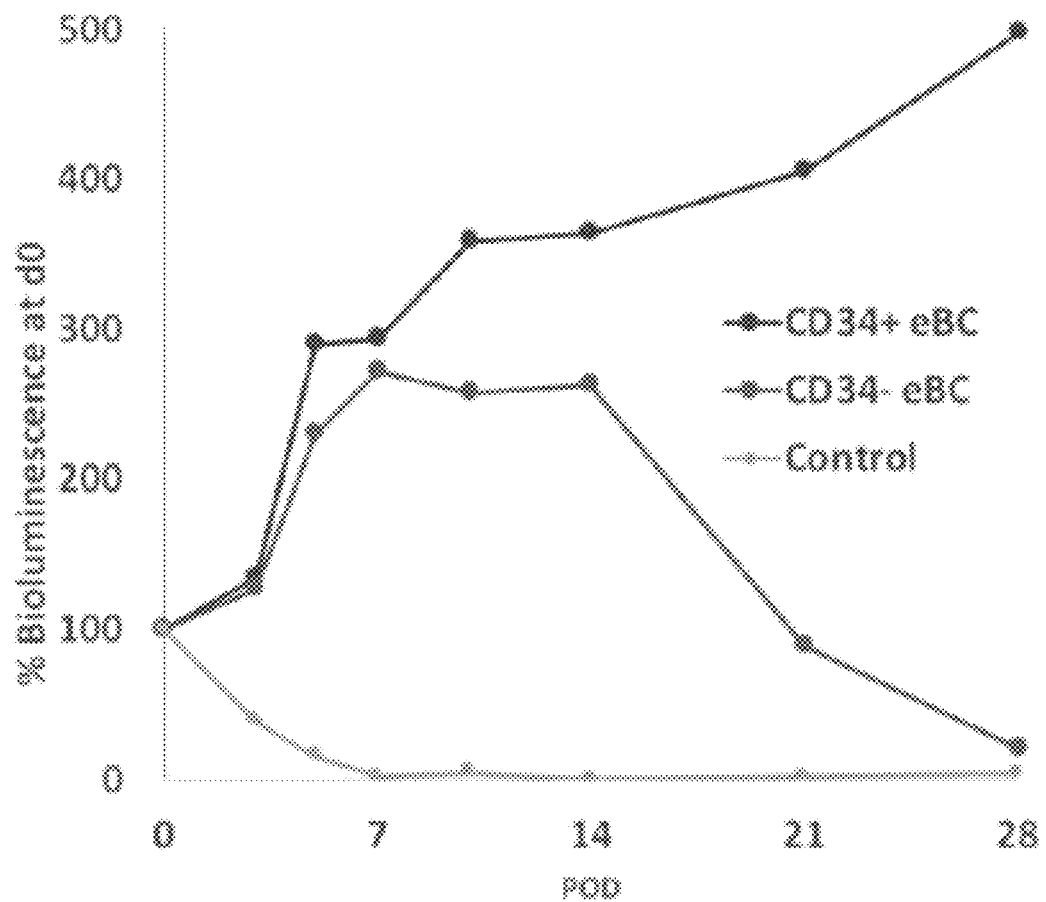

In these experiments, the co-clustered eBC were transplanted in the subcutaneous tissue of NSG immunodeficient mice to assess graft viability. Co-transplantation was performed as described in Example 5 above, where there was no need to co-transplant any other cells besides eBC as the helper cells (PTG-derived CD34+, CD34−) were already co-clustered with the eBC's. In these experiments, 5000 PTG-derived CD34+ cells, 5000 PTG-derived CD34− cells, and 500 IEQ eBC−luc+ cells were used. The readout was bioluminescence emitted from the transplanted luciferase-eBC, which was used as a surrogate for graft viability. A graft is determined to be alive when it emits bioluminescent signal following injection of a luciferin substrate into the bloodstream which is then taken up by the graft. Bioluminescence level at Day 0 was recorded as 100% and then monitored serially to determine whether the bioluminescence signal decreases or increases from time of transplant. As shown in FIGS. 25A-25B, the level of luciferase bioluminescence at post-operative Day 28 compared to post-operative Day 0 luciferase bioluminescence in the eBC control was below 5%, indicating over 95% graft loss. In contrast, in mice engrafted with a combination of eBC and PTG-derived CD34−, the level of luciferase bioluminescence initially elevated up to 200% but, after 14 days, started to go back to a level similar to that in the control by 28 days. This results indicated that the graft was able to maintain for 14 days by the presence of PTG derived CD34− but lacked sustainable protection. Remarkably, it was observed that (eBC+PTG-derived CD34+) continued to emit >400% bioluminescent luciferase signal past 28 days (n=2 in each experimental group).

Example 29

Co-Transplantation and Co-Clustering of ES-Derived CD34+ Confers Complete Protection of Enhanced Beta Cluster (eBC) and SCIPC Graft in SQ and IM This Example describes the results of in vivo mouse experiments performed to demonstrate that co-transplantation and co-clustering of ES-derived CD34+ cells confer complete protection of eBC and SCIPC grafts in subcutaneous and intramuscular transplantations.

Figure 26B:
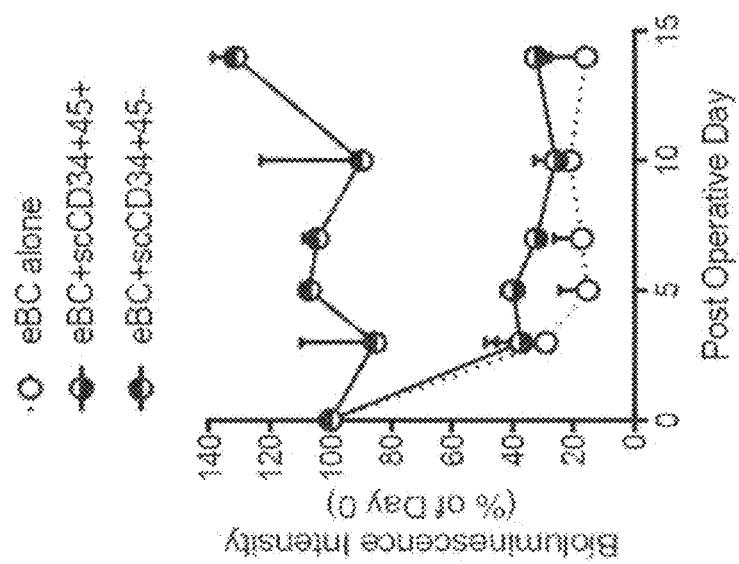
FIGS. 26A-26B pictorially summarize experimental results demonstrating that ES-derived CD34$^+$45$^-$ cells are capable of supporting eBC engraftment during co-transplantation.
Figure 26A:
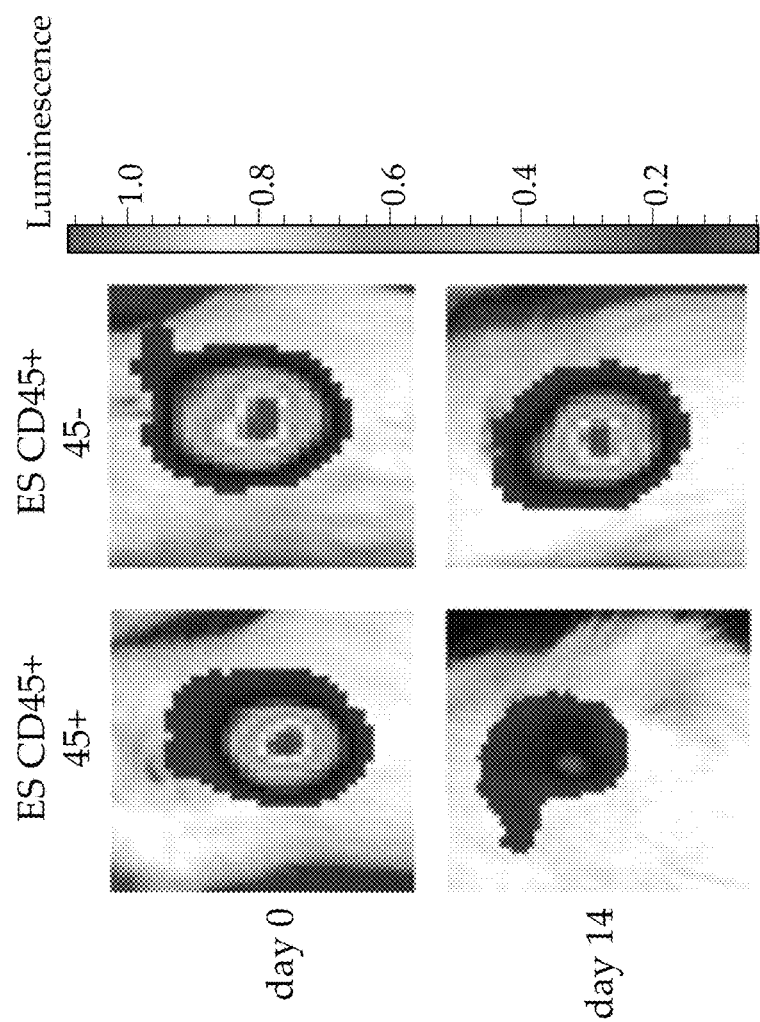

FIGS. 26A-26B pictorially summarize experimental results demonstrating that ES-derived CD34+45− cells are capable of supporting eBC engraftment during co-transplantation. In these experiments, 15,000 ES-derived CD34+45+ cells and 15,000 ES-derived CD34+45− cells were used (n=5 mice in each group). In these experiments, co-transplantation was performed as described in Example 5 above, where the eBC were transplanted with either ES-derived CD34+45+ cells or ES-derived CD34+45− cells as indicated. In the event that the helper cells (ES-derived CD34+, CD34−) were already co-clustered with the eBC, then only co-clustered eBC cells were transplanted. The readout was bioluminescence emitted from the transplanted luciferase-eBC, which was used as a surrogate for graft viability. A graft is determined to be alive when it emits bioluminescent signal following injection of a luciferin substrate into the bloodstream which is then taken up by the graft. Bioluminescence level at Day 0 was recorded as 100% and then monitored serially to determine whether the bioluminescence signal decreases or increases from time of transplant.

Figure 27A:
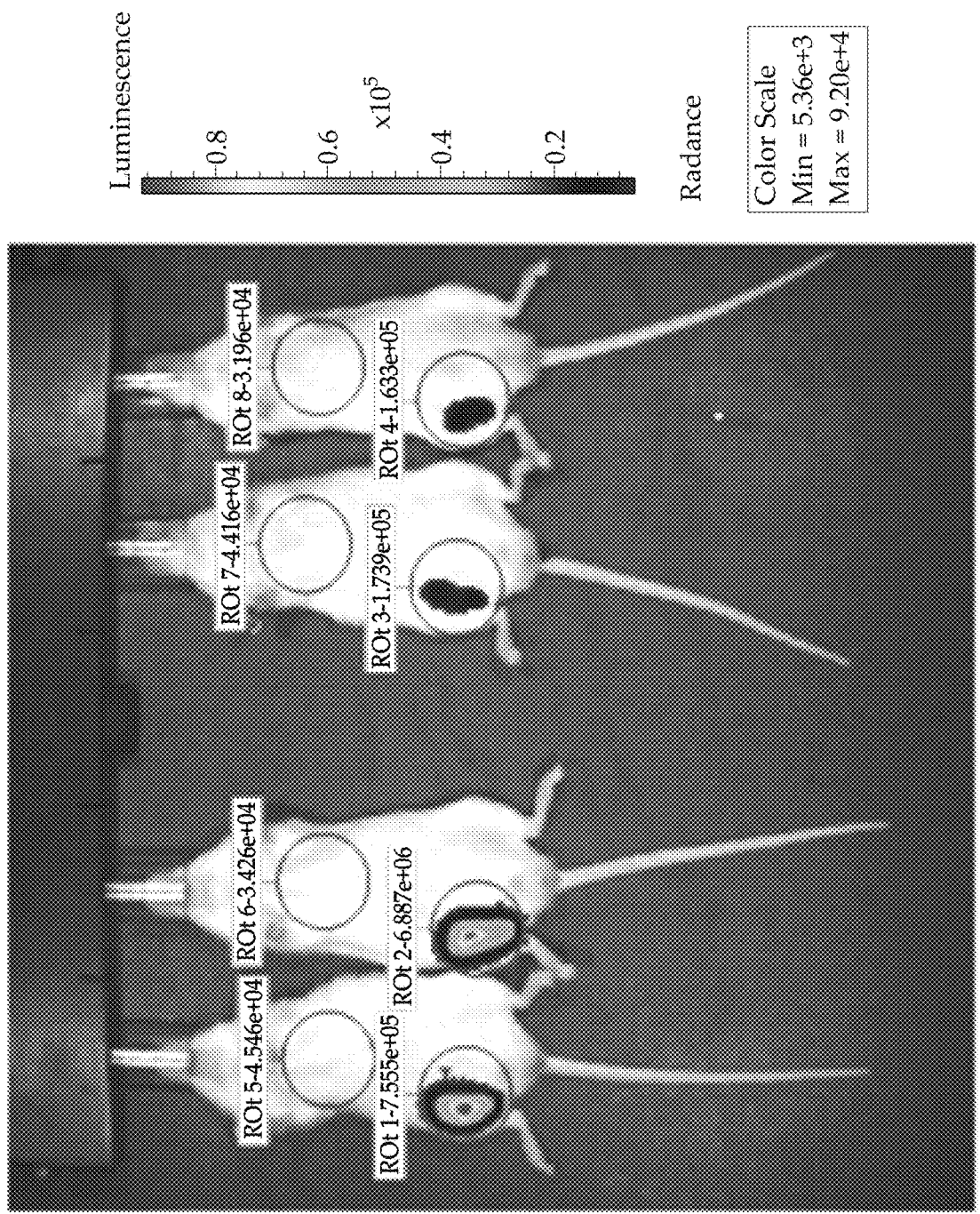
FIGS. 27A-27B summarize experimental results demonstrating that ES-derived CD34$^+$45$^-$ cells, when co-clustered with eBC, are capable of dramatically improving viability in intramuscular administration.
Figure 27B:
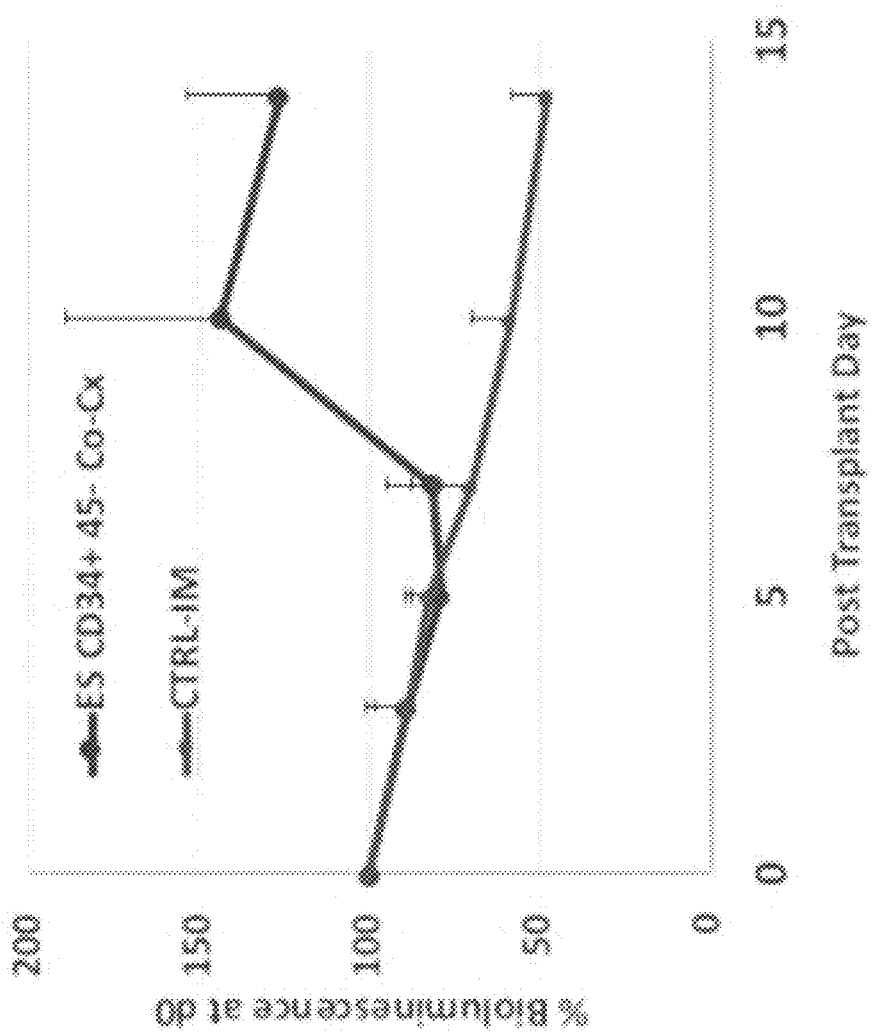

FIGS. 27A-27B pictorially summarize experimental results demonstrating that ES-derived CD34+45− cells, when co-clustered with eBC, are capable of dramatically improving viability in intramuscular administration. In these experiments, 5000 ES-derived CD34+ cells were co-clustered with 500 IEQ eBC-luc+ (n=2 in each group). In eBC-luc+ control in IM mice, the bioluminescent signal after 14 days dropped >50% compared to Day 0 signal, indicating >50% graft loss in the IM site. This was significantly superior to the SQ as site for transplantation but still showed significant graft loss (e.g., =50% IM versus <5% in SQ after 14 days). In contrast, eBC co-clustered with ES-derived CD34+ cells continued to have >125% signal after 21 days, indicating sustained graft protection.

Figure 28B:
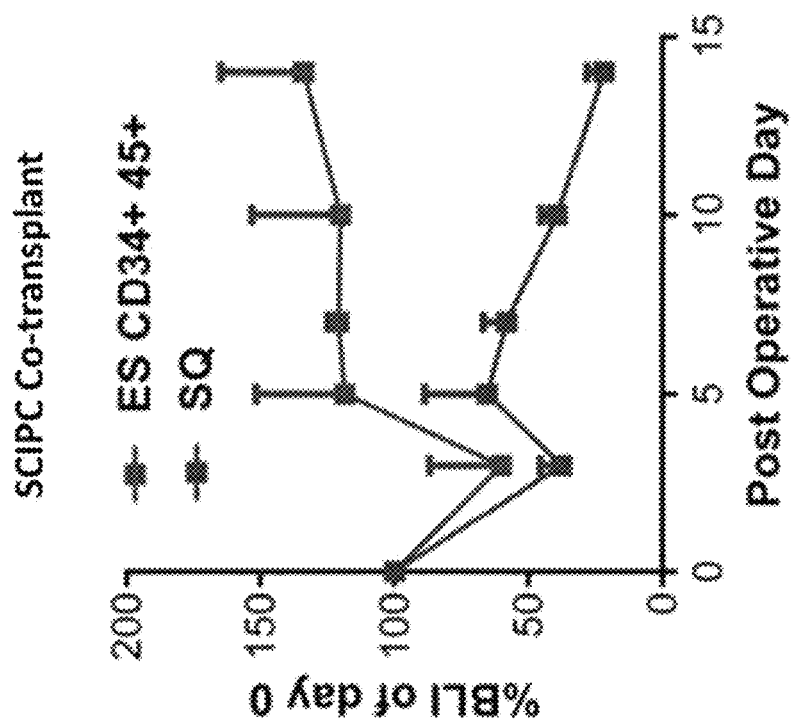
FIGS. 28A-28B pictorially summarize experimental results demonstrating that ES-derived CD34$^+$45$^+$ cells are capable of protecting SCIPC engraftment in subcutaneous site.
Figure 28A:
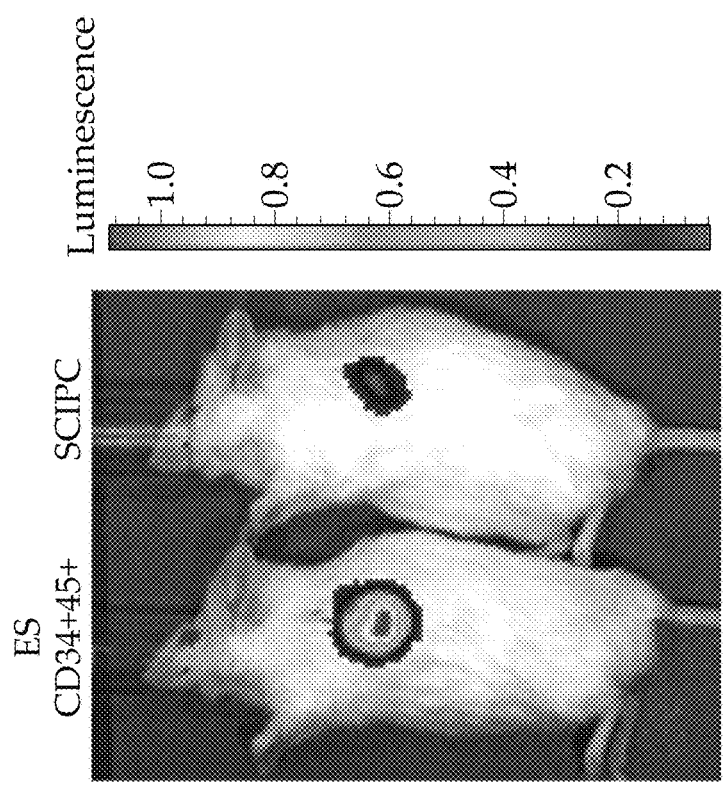

FIGS. 28A-28B pictorially summarize experimental results demonstrating that ES-derived CD34+45+ cells are capable of protecting SCIPC engraftment in subcutaneous site in accordance with some embodiments of the disclosure. An experimental protocol for the formation of vascular stem cell-derived insulin producing cells (vSCIPC) is described in Example 30 below. In the experiments presented in FIGS. 28A-28B, 1000 IEQ SCIPC clusters and 15,000 ES-derived CD34+45+ cells were used. As seen in prior experiments, the bioluminescent signal in the SCIPC alone group diminished over 75% after 14 days indicating significant graft loss. This result was in stark comparison to SCIPC co-transplanted with ES-derived CD34+45+ which showed sustained luciferase signal to 125% after 14 days compared to post-operative Day 0 luciferase signal, indicating complete graft protection (n=5 mice in each group.)

Figure 29B:
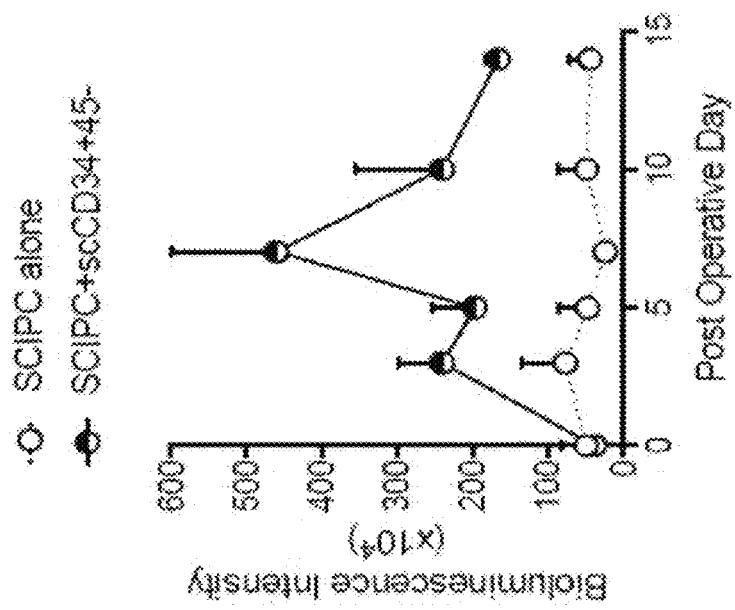
FIGS. 29A-29B pictorially summarize experimental results demonstrating that ES-derived CD34$^+$45$^-$ cells are capable of protecting SCIPC engraftment in subcutaneous site.
Figure 29A:
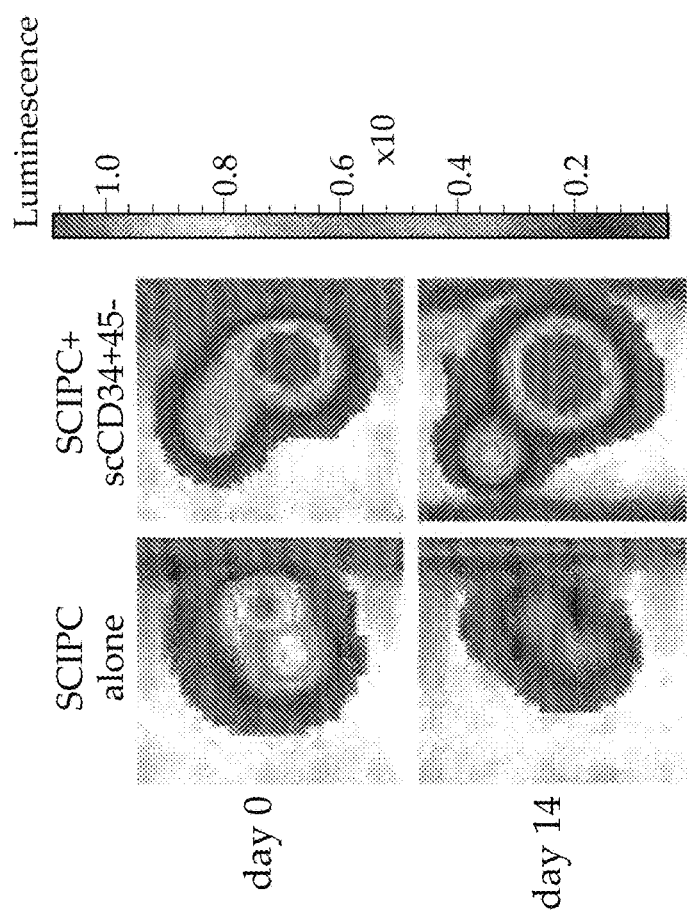

FIGS. 29A-29B pictorially summarize experimental results demonstrating that ES-derived CD34+45− cells are capable of protecting SCIPC engraftment in subcutaneous site. In these experiments, 1000 IEQ SCIPC clusters and 15,000 ES-derived CD34+45− cells were used. As seen in prior SCIPC experiments in the SQ site, the bioluminescent signal in the SCIPC alone group diminished over 50% after 14 days indicating significant graft loss. This result was in stark comparison to SCIPC co-transplanted with ES derived CD34+45− which showed sustained luciferase signal to 125% after 14 days compared to post-operative Day 0 luciferase signal, indicating complete graft protection (n=3 mice in each group).

Figure 30B:
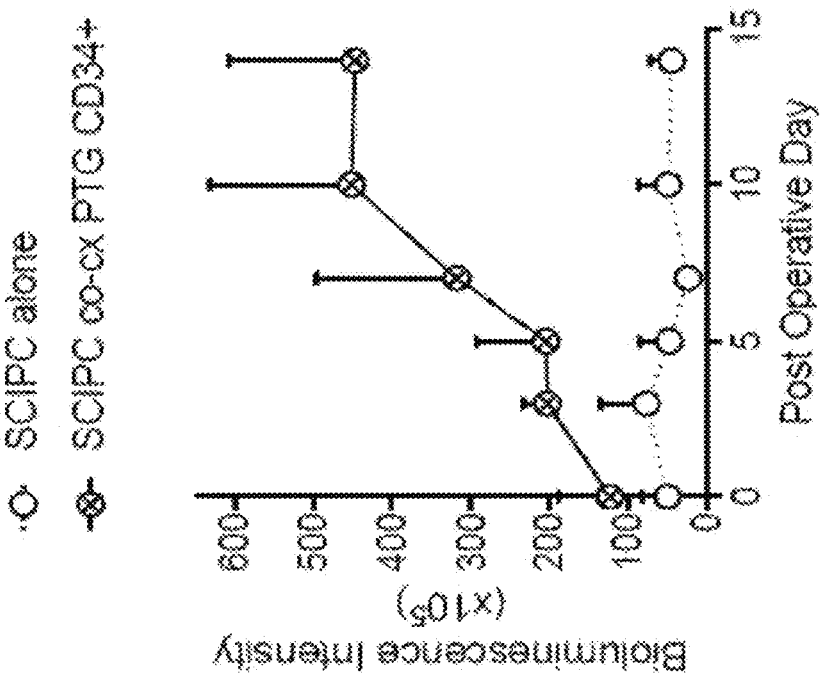
FIGS. 30A-30B pictorially summarize experimental results demonstrating that PTG-derived CD34$^+$ cells, when co-clustered with SCIPC, are capable of dramatically improving viability in subcutaneous site in accordance with some embodiments of the disclosure.
Figure 30A:
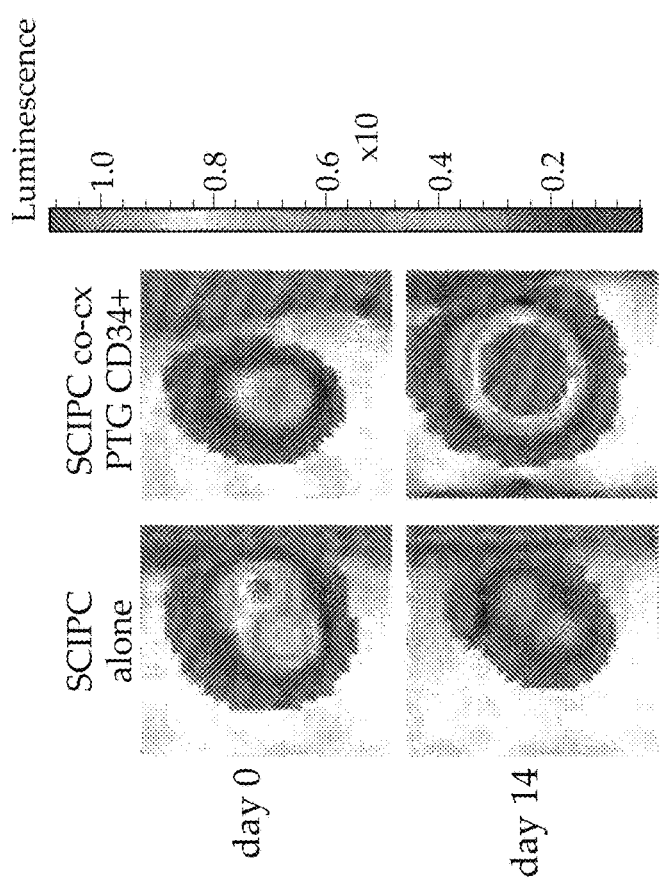

FIGS. 30A-30B pictorially summarize experimental results demonstrating that PTG-derived CD34$^+$ cells, when co-clustered with SCIPC, are capable of dramatically improving viability in subcutaneous site in accordance with some embodiments of the disclosure. In these experiments, 5000 PTG-derived CD34+ were co-clustered with 100 IEQ SCIPC-luc+ cells (N=3 in each group). It was observed that, in subcutaneous transplanted SCIPC-luc+ control mice, the bioluminescent signal after 14 days dropped >60% compared to Day 0 signal, indicating that more than 50% graft loss in the SQ site. In comparison, PTG-derived CD34+ cells, when co-clustered with SCIPC and transplanted in the subcutaneous site showed luciferase bioluminescent signal of nearly 400% that of post-operative Day 0 signal, indicating complete protection of SCIPC graft in the SQ site.

Example 30

Formation of Vascular Stem Cell-Derived Insulin Producing Cells (vSCIPCs)

This Example describes the preparation of vascular stem cell-derived insulin producing cells (vSCIPC) in accordance with some embodiments of the disclosure. Human pluripotent stem cells (hPSCs) were maintained and propagated on mouse embryonic fibroblasts (MEFs) in hPSC media. Confluent hPSC cultures were dissociated into single-cell suspension and seeded in suspension plates in hPSC media supplemented with Activin A (10 ng/ml, R&D Systems) and HeregulinB (10 ng/ml, Peprotech). The plates were incubated on an orbital shaker to induce 3D sphere formation. Spheres were cultured for 15 days using the following media:

Day 1: RPMI (Gibco) containing 0.2% FBS, 1:5,000 ITS (Gibco), 100 ng/ml activin A, 50 ng/ml WNT3a (R&D Systems);

Day 2: RPMI containing 0.2% FBS, 1:2,000 ITS, 100 ng/ml activin A;

Day 3: RPMI containing 0.2% FBS, 1:1,000 ITS, 2.5 µM TGFbi IV (CalBioChem), 25 ng/ml KGF (R&D Systems);

Days 4-5: RPMI containing 0.4% FBS, 1:1,000 ITS, 25 ng/ml KGF;

Days 6-7: DMEM (Gibco) with 25 mM glucose containing 1:100 B27 (Gibco), 3 nM TTNBP (Sigma);

Day 8: DMEM with 25 mM glucose containing 1:100 B27, 3 nM TTNBP, 50 ng/ml EGF (R&D Systems);

Days 9-11: DMEM with 25 mM glucose containing 1:100 B27, 50 ng/ml EGF, 50 ng/ml KGF;

Days 12-15: DMEM with 25 mM glucose containing 1:100 B27, 1:100 Glutamax (Gibco), 1:100 NEAA (Gibco), 10 µm ALKi II (Axxora), 500 nM LDN-193189 (Stemgent), 1 µm Xxi (Millipore), 1 µM T3 (Sigma-Aldrich), 0.5 mM Vitamin C, 1 mM N-acetyl Cysteine (Sigma-Aldrich), 10 µM zinc sulfate (Sigma-Aldrich) and 10 µg/ml of Heparin sulfate.

After 15 days of differentiation, spheres were dissociated in single cell suspension using Accumax. Dissociated cells were mixed with PTG-derived CD34+ cells or hPSC-derived CD34+ cells at different ratios, and 3D spheres were reformed by orbital shaking. Spheres were maintained in D12-15 media for five additional days, in the presence of Penicillin/Streptomycin, and used for transplantation after a total of 20 days of differentiation.

1000 IEQ of mature human islets and ⅛ of a PTG was co-transplanted in the IM site, enabling diabetes reversal in ⅘ mice at 100 days compared to ⅕ mice in IM alone. Consecutive histology sections were prepared from tissue collected at 100 days post-transplant and were stained with H+E (FIG. 31A, left) and insulin immunofluorescence acquired on a confocal microscope (FIG. 31A, right). Corresponding single islet is indicated by arrow. The images show unprecedented high-density engraftment of human islets in the muscle tissue. This level of density was previously thought to be impossible to achieve (Sci Rep. 2018 Apr. 25; 8(1):6508. doi: 10.1038/s41598-018-23862-w). Previous efforts to overcome islet cell death after transplant by transplanting higher islet equivalents found that more islet die with high-density transplants from over-crowding that exacerbate ischemic injury and inability of neoangiogenic induced by the islet graft to support high density survival. This demonstration of the feasibility of achieving high-density engraftment of human pancreatic islets (FIG. 31A) and stem cell derived islets (FIG. 6C) will open the field of beta cell replacement therapy to consider transplanting beta cell in more confined space such as SQ and IM for monitoring graft function, immune responses against grafts and localized immune modulation in the graft bed.

It has been shown in previous studies that prolonged culture (>24-48 hrs) of isolated human pancreatic islets leads to loss of islet-resident vascular endothelial cells that may reduce the efficacy of islet revascularization after transplant. We show here that human pancreatic islets transplanted in the subcutaneous tissue alone of immunodeficient mice indeed lose all human vascular endothelial cells (indicated by absence of green human von Willebrand Factor (vWF) staining) after 5 days (FIG. 32A). In contrast, PTG co-transplanted islets show maintenance of human-derived vascular endothelial cells (indicated by green staining from human vWF) as well as robust mouse CD31 vessel ingrowth (indicated by red CD31 staining) (FIG. 32B). These results suggest that parathyroid gland co-transplantation support the survival of human pancreatic islet-resident vascular endothelial cells after transplantation in the mouse subcutaneous tissue.

Figure 33:
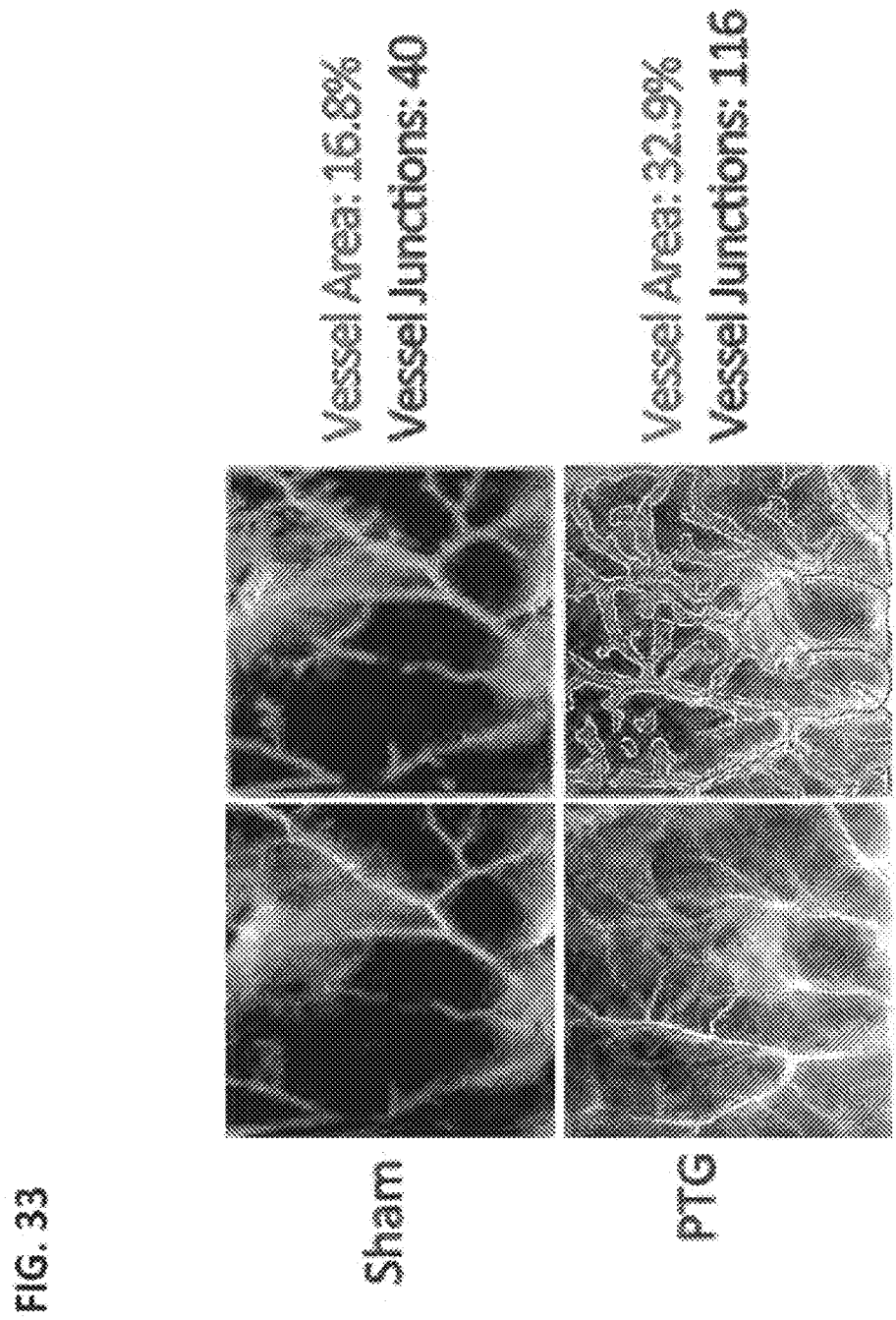
FIG. 33 pictorially summarizes the results from experiments performed to illustrate the angiogenic ability of parathyroid gland (PTG) Angiogenic ability of parathyroid gland (PTG). In vivo angiogenesis in the subcutaneous sites 5 days after sham operation or PTG transplant. Photos of the blood vessels on skin-flaps were converted to black and white images (left) and the vessel area (marked red in the right images) percentage and number of vessel junctions (marked by blue dots in the right images) were quantified with the aid of the AngioTool Software (NIH).

PTG's ability to induce neoangiogenesis is demonstrated in an in vivo angiogenesis assay showing dramatic increase of vessel area percentages and numbers of vessel junctions as early as day 5 in the subcutaneous space that received the PTG transplant (FIG. 33).

The neoangiogenic potential of purified PTG CD34+ and CD34− cells were compared using the in vivo skin flap assay. The sham and parathyroid CD34− group showed higher vessel area percentage and number of vessel junctions on day 5 (FIG. 34A) than on day 14 (FIG. 34B) after surgery. In contrast, the parathyroid CD34+ group showed sustained high vessel areas and vessel junctions at both time points. This result suggests that general inflammatory response from the procedure leads to transient increase in vascular perfusion of the transplant site whereas parathyroid CD34+ induced early and sustained increase in angiogenesis. Furthermore, histological analysis of the skin tissue collected on day 14 show characteristic dermal vessel visualized using antibodies to mouse endothelial marker CD31 in sham and parathyroid CD34-transplant groups (FIG. 34C). The parathyroid CD34+ transplanted tissue showed both human endothelial cells visualized with anti-human Von Willebrand Factor antibody and mouse vessels. The co-localization of human and mouse endothelial cells indicates chimeric vessel formation suggesting that the parathyroid CD34+ cells can turn into vascular endothelial cells themselves as well as promoting ingrowth and anastomosis with host blood vessels.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

We claim:

1. A method for treating diabetes mellitus in an individual in need thereof, comprising administering to the individual a transplant comprising:
   (a) an insulin-producing cell, and
   (b) a cell selected from (i) a cell derived from a parathyroid gland (PTG) and (ii) a CD34+ cell, wherein the cell produces one or more factors selected from a proangiogenic factor, a PTG hormone, and a combination thereof,
   thereby treating the diabetes mellitus.

2. The method of claim 1, wherein the insulin-producing cell is differentiated from a stem cell.

3. The method of claim 1, wherein the insulin-producing cell is a stem cell-derived insulin-producing cell (SCIPC) or a stem cell-derived enhanced beta cluster (eBC).

4. The method of claim 1, wherein the insulin-producing cell is a pancreatic islet beta cell.

5. The method of claim 1, wherein the one or more factors is selected from vascular endothelial growth factor VEGF), platelet-derived growth factor (PDGF), angiopoietin, gamma-aminobutyric acid GABA), parathormone (PTH), PTH-related peptide (PTHrP), and a combination thereof.

6. The method of claim 1, wherein the transplant is administered to an extrahepatic site.

7. The method of claim 6, wherein the extrahepatic site is subcutaneous or intramuscular.

8. The method of claim 1, wherein the transplant is administered using a catheter, a cannula, a syringe, or an implantable device.

9. The method of claim 1, wherein the diabetes mellitus is type 1 diabetes, type 2 diabetes, or surgical diabetes.

10. The method of claim 1, wherein the cell is a cell derived from PTG.

11. The method of claim 1, wherein the cell is a CD34+ cell.

12. A method for treating diabetes mellitus in an individual in need thereof, comprising administering to the individual a transplant comprising:
    (a) an insulin-producing cell,
    (b) a cell that produces one or more PTG hormones; and
    (c) a cell that produces one or more proangiogenic factors,
    thereby treating the diabetes mellitus.

13. The method of claim 12, wherein the insulin-producing cell is differentiated from a stem cell.

14. The method of claim 12, wherein the insulin-producing cell is a SCIPC or a stem cell-derived eBC.

15. The method of claim 12, wherein the insulin-producing cell is a pancreatic islet beta cell.

16. The method of claim 12, wherein the cell that produces one or more PTG hormones is derived from PTG.

17. The method of claim 12, wherein the one or more PTG hormones is selected from GABA, PTH, PTHrP, and a combination thereof.

18. The method of claim 12, wherein the one or more PTG hormones comprises PTH.

19. The method of claim 12, wherein the cell that produces one or more proangiogenic factors is a CD34+ cell.

20. The method of claim 12, wherein the one or more proangiogenic factors is selected from VEGF, PDGF, angiopoietin, and a combination thereof.

21. The method of claim 12, wherein the transplant is administered to an extrahepatic site.

22. The method of claim 12, wherein the extrahepatic site is subcutaneous or intramuscular.

23. The method of claim 12, wherein the transplant is administered using a catheter, a cannula, a syringe, or an implantable device.

24. The method of claim 12, wherein the diabetes mellitus is type 1 diabetes, type 2 diabetes, or surgical diabetes.

* * * * *